US008586555B2

(12) United States Patent
Fearon et al.

(10) Patent No.: US 8,586,555 B2
(45) Date of Patent: Nov. 19, 2013

(54) IMMUNOMODULATORY COMPOSITIONS, FORMULATIONS, AND METHODS FOR USE THEREOF

(75) Inventors: Karen L. Fearon, Lafayette, CA (US); Dino Dina, Oakland, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 338 days.

(21) Appl. No.: 12/396,348

(22) Filed: Mar. 2, 2009

(65) Prior Publication Data

US 2010/0291218 A1    Nov. 18, 2010

Related U.S. Application Data

(63) Continuation of application No. 10/214,799, filed on Aug. 7, 2002, now abandoned.

(60) Provisional application No. 60/310,743, filed on Aug. 7, 2001, provisional application No. 60/335,263, filed on Oct. 25, 2001.

(51) Int. Cl.
*A61K 48/00* (2006.01)
*A61K 45/00* (2006.01)
*A61K 47/00* (2006.01)
*C07H 21/02* (2006.01)
*C07H 21/04* (2006.01)

(52) U.S. Cl.
USPC ............... 514/44 R; 536/23.1; 424/278.1

(58) Field of Classification Search
None
See application file for complete search history.

(56) References Cited

U.S. PATENT DOCUMENTS

| | | | |
|---|---|---|---|
| 4,458,066 A | 7/1984 | Caruthers et al. | |
| 4,489,055 A | 12/1984 | Couvreur et al. | |
| 4,650,675 A | 3/1987 | Borel et al. | |
| 4,849,513 A | 7/1989 | Smith et al. | |
| 4,910,300 A | 3/1990 | Urdea et al. | |
| 4,948,882 A | 8/1990 | Ruth | |
| 5,015,733 A | 5/1991 | Smith et al. | |
| 5,093,232 A | 3/1992 | Urdea et al. | |
| 5,118,800 A | 6/1992 | Smith et al. | |
| 5,118,802 A | 6/1992 | Smith et al. | |
| 5,124,246 A | 6/1992 | Urdea et al. | |
| 5,391,723 A | 2/1995 | Priest | |
| 5,453,496 A | 9/1995 | Caruthers et al. | |
| 5,484,596 A | 1/1996 | Hanna, Jr. et al. | |
| 5,593,875 A * | 1/1997 | Wurm et al. ............... | 435/455 |
| 5,663,153 A | 9/1997 | Hutcherson et al. | |
| 5,723,335 A | 3/1998 | Hutcherson et al. | |
| 5,849,719 A | 12/1998 | Carson et al. | |
| 6,174,872 B1 | 1/2001 | Carson et al. | |
| 6,194,388 B1 | 2/2001 | Krieg et al. | |
| 6,207,646 B1 * | 3/2001 | Krieg et al. ............... | 514/44 R |
| 6,214,806 B1 | 4/2001 | Krieg et al. | |
| 6,225,292 B1 | 5/2001 | Raz et al. | |
| 6,239,116 B1 | 5/2001 | Krieg et al. | |
| 6,406,705 B1 | 6/2002 | Davis et al. | |
| 6,426,334 B1 | 7/2002 | Agrawal et al. | |
| 6,476,000 B1 | 11/2002 | Agrawal | |
| 6,534,062 B2 | 3/2003 | Raz et al. | |
| 6,589,940 B1 * | 7/2003 | Raz et al. ............... | 514/44 R |
| 6,613,751 B2 | 9/2003 | Raz et al. | |
| 7,255,868 B2 | 8/2007 | Fearon et al. | |
| 2001/0046967 A1 | 11/2001 | Van Nest | |
| 2002/0028784 A1 | 3/2002 | Nest | |
| 2002/0055477 A1 | 5/2002 | Nest et al. | |
| 2002/0098199 A1 | 7/2002 | Van Nest et al. | |
| 2002/0107212 A1 | 8/2002 | Nest et al. | |
| 2003/0022852 A1 | 1/2003 | Nest et al. | |
| 2003/0049266 A1 | 3/2003 | Fearon et al. | |
| 2003/0050268 A1 | 3/2003 | Krieg et al. | |
| 2003/0059773 A1 | 3/2003 | Van Nest et al. | |
| 2003/0133988 A1 | 7/2003 | Fearon et al. | |
| 2003/0175731 A1 | 9/2003 | Fearon et al. | |
| 2003/0199466 A1 | 10/2003 | Fearon et al. | |
| 2003/0225016 A1 | 12/2003 | Fearon et al. | |
| 2004/0132677 A1 | 7/2004 | Fearon et al. | |
| 2007/0049550 A1 | 3/2007 | Fearon et al. | |
| 2008/0181909 A1 | 7/2008 | Fearon et al. | |

FOREIGN PATENT DOCUMENTS

| | | |
|---|---|---|
| EP | 0 468 520 | 1/1992 |
| WO | WO-96/02555 | 2/1996 |
| WO | WO-97/28259 | 8/1997 |
| WO | WO-98/16247 | 4/1998 |
| WO | WO-98/18810 | 5/1998 |
| WO | WO-98/37919 | 9/1998 |
| WO | WO-98/40100 | 9/1998 |
| WO | WO-98/52581 | 11/1998 |
| WO | WO-98/52962 | 11/1998 |
| WO | WO-98/55495 | 12/1998 |
| WO | WO-98/55609 | 12/1998 |

(Continued)

OTHER PUBLICATIONS

Sonehara et al (1996 Journal Interferon and Cytokine Research 16: pp. 799-803).*
Agrawal, Sudhir et al. (1986). "Efficient Methods for Attaching Non-Radioactive Labels to the 5' Ends of Synthetic Oligodeoxyribonucleotides," *Nucleic Acids Res.* 14(15):6227-6245.
Ahmeida, et al. (1993). "Immunopotentiation Local and Systemic Humoral Immune Responses by ISCOMs, Liposomes and FCA: Role in Protection Against Influenza A in Mice," *Vaccine* 11(13):1302-1309.
Asanuma, et al. (1995). "Cross-Protection Against Influenza Virus Infection in Mice Vaccinated by Combined Nasal-Subcutaneous Administration," *Vaccine* 13(1):3-5.
Atherton et al. (1981). "Synthesis of a 21-Residue Fragment of Human Proinsulin by the Polyamide Solid Phase Method," *Hoppe Seylers Z. Physiol. Chem.* 362:833-839.

(Continued)

*Primary Examiner* — Nita M Minnifield
*Assistant Examiner* — Nina Archie
(74) *Attorney, Agent, or Firm* — Morrison & Foerster LLP

(57) ABSTRACT

The invention provides new compositions and methods for immunomodulation of individuals. Immunomodulation is accomplished by administration of immunomodulatory polynucleotide/microcarrier (IMO/MC) complexes comprising 3-6mer immunomodulatory oligonucleotides. The IMO/MC complexes may be covalently or non-covalently bound. Also provided are immunomodulatory compositions comprising a 3-6mer IMO encapsulated in an MC.

37 Claims, No Drawings

(56) References Cited

FOREIGN PATENT DOCUMENTS

| | | |
|---|---|---|
| WO | WO-99/11275 | 3/1999 |
| WO | WO-99/33488 | 7/1999 |
| WO | WO-99/33868 | 7/1999 |
| WO | WO-99/51259 | 10/1999 |
| WO | WO-99/56755 | 11/1999 |
| WO | WO-99/62923 | 12/1999 |
| WO | WO-00/06588 | 2/2000 |
| WO | WO-00/16804 | 3/2000 |
| WO | WO-00/21556 | 4/2000 |
| WO | WO-00/50006 | 8/2000 |
| WO | WO-00/54803 | 9/2000 |
| WO | WO-00/61161 | 10/2000 |
| WO | WO-00/62787 | 10/2000 |
| WO | WO-00/67023 | 11/2000 |
| WO | WO-01/12223 | 2/2001 |
| WO | WO-01/12804 | 2/2001 |
| WO | WO-01/15726 | 3/2001 |
| WO | WO-01/22972 | 4/2001 |
| WO | WO-01/22990 | 4/2001 |
| WO | WO-01/35991 | 5/2001 |
| WO | WO-01/45750 | 6/2001 |
| WO | WO-01/51500 | 7/2001 |
| WO | WO-01/54720 | 8/2001 |
| WO | WO-01/55341 | 8/2001 |
| WO | WO-01/55370 | 8/2001 |
| WO | WO-01/62207 | 8/2001 |
| WO | WO-01/68103 | 9/2001 |
| WO | WO-01/68143 | 9/2001 |
| WO | WO-01/68144 | 9/2001 |
| WO | WO0168143 * | 9/2001 |
| WO | WO-01/72123 | 10/2001 |
| WO | WO-03/014316 | 2/2003 |

OTHER PUBLICATIONS

Ballas, et al. (1996). "Induction of NK activity in murine and human cells by CpG motifs in oligodeoxynulcleotides and bacterial DNA," *J. Immunol.* 157:1840-1845.

Beaucage, S. L. (1993). "Chapter 3: Oligodeoxyribonucleotide Synthesis," in *Protocols for Oligonucleotides and Analogs, Synthesis and Properties*, Sudhir Agrawal, ed., Humana Press, Totowa, NJ, vol. 20, pp. 33-61.

Benoit, et al. (1987). "Peptides. Strategies for Antibody Production and Radioimmunoassays," in *Neuromethods*, Alan A. Boulton et al., eds., Humana Press, Clifton, NJ: pp. 43-72.

Bischoff, et al. (1987). "Introduction of 5'-Terminal Functional Groups into Synthetic Oligonucleotides for Selective Immobilization," *Analytical Biochemistry* 164:336-344.

Blanks et al. (1988). "An Oligodeoxynucleotide Affinity Column for the Isolation of Sequence Specific DNA Binding Proteins," *Nucleic Acids Res.* 16:10283-10299.

Boujrad et al. (1993) "Inhibition of Hormone-Stimulated Steroidogenesis in Cultured Leydig Tumor Cells by a Cholesterol-Linked Phosphorothioate Oligodeoxynucleotide Antisense to Diazepam-Binding Inhibitor," *Proc. Natl. Acad. Sci. USA* 90:5728-5731.

Branda et al. (1993). "Immune Stimulation by an Antisense Oligomer Complementary to the rev Gene of Hiv-1," *Biochem. Pharmacol.* 45(10):2037-2043.

Branda et al. (1996). "Amplification of Antibody Production by Phosphorothioate Oligodeoxynucleotides," *J. Lab. Clin. Med.* 128:329-338.

Braun, R.P. et al. (1988). "Immunogenic Duplex Nucleic Acids are Nuclease Resistant," *J. Immunol.* 141(6):2084-2089.

Brazolot-Millan et al. (1998). "CpG DNA Can Induce Strong Th1 Humoral and Cell-mediated Immune Responses Against Hepatitis B Surface Antigen in Young Mice," *Proc. Natl. Acad. Sci. USA* 95:15553-15558.

Breiteneder et al. (1989). "The Gene Coding for the Major Birch Pollen Allergen Betvl, is highly homologous to a Pea Disease Resistance Response Gene," *EMBO J.* 8(7):1935-1938.

Broide et al. (1998). "Immunostimulatory DNA Sequences Inhibit IL-5, Eosinophilic Inflammation, and Airway Hyperresponsiveness in Mice," *J. Immunol.* 161:7054-7062.

Broide, D. et al. (1999). "DNA-Based Immunization for Asthma," *Int. Arch. Allergy Immunol.* 118:453-456.

Carson, D.A. et al.. (1997). "Oligonucleotide Adjuvants for T helper 1 (Th1)-specific Vaccination," *J. Exp. Med.* 186(10):1621-1622.

Chace et al. (1997). "Bacterial DNA-Induced NK Cell IFN-§ Production is Dependent on Macrophage Secretion of IL-12," *Clin. Immunol. and Immunopathol.* 84:185-193.

Chaturvedi et al. (1996). "Stabilization of Triple-stranded Oligonucleotide Complexes: Use of Probes Containing Alternating Phosphodiester and Stereo-uniformed Cationic Phosphoramidate Linkages," *Nucleic Acids Res.* 24:2318-2323.

Chen et al. (1999). "Enhanced Protection Against a Lethal Influenza Virus Challenge by Immunization With Both Hemagglutinin- and Neuraminidase-expressing DNAs," *Vaccine* 17:653-659.

Chu et al. (1997). "CpG Oligodeoxynucleotides Act as Adjuvant that Switch on T Helper 1 (Th1) Immunity," *J. Exp. Med.* 186:1623-1631.

Chua et al. (1988). "Sequence Analysis of cDNA Coding for a Major House Dust Mite Allergen, Der p 1," *J. Exp. Med.* 167:175-182.

Chua et al. (1990). "Expression of Dermatophagoides Pteronyssinus Allergen, Der p II, in *Escherichia coli* and the Binding Studies with Human IgE," *Int. Arch. Allergy Appl. Immunol.* 91:124-129.

Connolly. (1985). "Chemical Synthesis of Oligonucleotides Containing a Free Sulphydryl Group and Subsequent Attachment of Thiol Specific Probes," *Nucleic Acids Res.* 13:4485-4502.

Connolly. (1987). "The Synthesis of Oligonucleotides Containing a Primary Amino Group at the 5'-Terminus," *Nucleic Acids Res.* 15:3131-3139.

Corey et al. (1987). "Generation of a Hybrid Sequence-Specific Single-Stranded Deoxyribonuclease," *Science* 238:1401-1403.

Cowdery et al. (1996). "Bacterial DNA-Induced NK Cell to Produce IFN-K In Vivo and Increases the Toxicity of Lipopolysaccharides," *J. Immunol.* 156:4570-4575.

De Martino et al. (1999). "Low IgG3 and high IgG4 subclass levels in children with advanced human immunodeficiency virus-type 1 infection and elevated IgE levels," *Ann. Allergy Asthma Immunol.* 83:160-164.

Elkins et al. (1999). "Bacterial DNA Containing CpG Motifs Stimulates Lymphocyte-Dependent Protection of Mice Against Lethal Infection with Intracellular Bacteria," *J. Immunol.* 162:2291-2298.

Elsayed et al. (1991). "The Structural Requiements of Epitopes With IgE Binding Capacity Demonstrated by Three Major Allergens From Fish, Egg and Tree Pollen," *Scand. J. Clin. Lab. Invest.* 51(Suppl. 204)17-31.

Fornadley, J. (1998). "Allergy Immunotherapy," *Otolaryngol. Clin. North Am.* 31(1):111-127.

Geoghegan, K.F. et al. (1992). "Site-Directed Conjugation of Nonpeptide Groups to Peptides and Proteins via Periodate Oxidation of a 2-Amino Alcohol. Application to Modification at N-Terminal Serine," *Bioconjug. Chem.* 3:138-146.

Godard, et al. (1995). "Antisense Effects of Cholesterol-Oligodeoxynucleotide Conjugates Associated with Poly(Alkylcyanoacrylate) Nanoparticles," *Eur. J. Biochem.* 232:404-410.

Govorkova, E.A. et al. (1997). "Cross-Protection of Mice Immunized with Different Influenza A (H2) Strains and Challenged with Viruses of the Same HA Subtype," *Acta Virol.* 41:251-257.

Grabarek, Z. et al. (1990). "Zero-Length Crosslinking Procedure with the Use of Active Esters," *Anal. Biochem.* 185:131-135.

Gramzinski et al. (1998) "Immune Response to a Hepatitis B DNA Vaccine in Aotus Monkeys: A Comparison of Vacine Formulation, Route, and Method of Administration," *Molecular Medicine* 4:109-118.

Granoff et al. (1993). "Effect of Immunity to the Carrier Protein on Antibody Responses to *Haemophilus Influenzae* Type b Conjugate Vaccines," *Vaccine* 11(Suppl.1):S46-S51.

Gursel et al. (2000). "Immunoadjuvant Action of PLASMID DNA in Liposomes," *Vaccine* 17:1376-1383.

Hames, B.D. et al., eds. (1987). *Transcription and Translation A Practical Approach*, IRL Press: pp. vii-xiv (Table of Contents).

(56) References Cited

OTHER PUBLICATIONS

Haralambidis et al. (1990). "The Synthesis of Polyamide—Oligonucleotide Conjugate Molecules," *Nucleic Acids Res.* 18(3):493-499.
Haralambidis et al. (1990). "The Preparation of Polyamide-Oligonucleotide Probes Containing Multiple Non-radioactive Labels," *Nucleic Acids Res.* 18(3):501-505.
Horner et al. (1998). "Immunostimulatory DNA is a Potent Mucosal Adjuvant," *Cell Immunol.* 190:77-82.
International Search Report mailed Jun. 27, 2003 for PCT Application No. PCT/US02/25123, one page.
Jager et al. (1988). "Oligonucleotide N-Alkylphosphoramidates: Synthesis and Binding to Polynucleotides," *Biochem.* 27:7247-7246.
Jakob et al. (1998). "Activation of Cutaneous Dendritic Cells by CpG-Containing Oligodeoxynucleotides: A Role for Dendritic Cells in the Augmentation of Th1 Responses by Immunostimulatory DNA," *J. Immunol.* 161:3042-3049.
Kandimalla et al. (2001). "Effect of Chemical Modifications of Cytosine and Guanine in a CpG-Motif of Oligonucleotides: Structure-Immunostimulatory Activity Relationships," *Bioorg. Med. Chem.* 9:807-813.
Kataoka et al. (1992). "Antitumor Activity of Synthetic Oligonucleotides with Sequences from cDNA Encoding Proteins of *Mycobacterium bovis* BCG," *Jpn. J. Cancer Res.* 83:244-247.
Kessler, C. (1992). "Nonradioactive Labeling Methods for Nucleic Acids," Chapter 2 in *Nonisotopic DNA Probe Techniques*, Larry J. Kricka, ed., Academic Press, Inc.: pp. 29-92.
Kikuta et al. (1990) "Cross-protection against influenza B type virus infection by intranasal inoculation of the HA vaccines combined with cholera toxin B subunit," *Vaccine* 8:595-599.
Kimura et al. (1994) "Binding of Oligoguanylate to Scavenger Receptors is Required for Oligonucleotides to Augment NK CalII Activity and Induce IFN,"*J. Biochem.* 116:991-994.
Kline et al. (1997). "Immune Redirection by CpG Oligonucleotides: Coversion of a Th2 Response to a Th1 response in a Murine Model of Asthma," *J. Invest. Med.* 45(3):282A (abstract).
Klinman et al. (1996). "CpG motifs present in bacterial DNA rapidly induce lymphocytes to secrete interleukin 6, interleukin 12, and interferon K," *Proc. Natl. Acad. Sci. USA* 93:2879-2883.
Klinman et al. (1997). "Contribution of CpG Motifs to the Immunogenicity of DNA Vaccines," *J. Immunol.* 158:3635-3639.
Kodihalli et al. (1997). "Cross-Protection Among Lethal H5N2 Influenza Viruses Induced by DNA Vaccine to the Hemagglutinin," *J. Virol.* 71(5):3391-3396.
Kovarik et al. (1999). "CpG Oligodeoxynucleotides can Circumvent the Th2 Polarization of Neonatal Responses to Vaccines but May Fail to Fully Redirect Th2 Responses Established by Neonatal Priming," *J. Immunol.* 162:1611-1617.
Kremsky et al. (1987). "Immobilization of DNA via Oligonucleotides Containing an Aldehyde or Carboxylic Acid Group at the 5' Terminus," *Nucleic Acids Res.* 15(7):2891-2909.
Krieg, A.M. et al. (1989). "A Role for Endogenous Retroviral Sequences in the Regulation of Lymphocyte Activation," *J. Immunol.* 143(8):2448-2451.
Krieg, A.M. et al. (1995). "CpG motifs in bacterial DNA trigger direct B-cell activation," *Nature* 374:546-549.
Krieg, A.M. (1996). "Lymphocyte Activation by CpG Dinucleotide Motifs in Prokaryotic DNA," *Trends Microbiol.* 4(2):73-76.
Krieg A.M. et al. (1996) "Oligodeoxynucleotide Modifications Determine the Magnitude of B Cell Stimulation by CpG Motifs," *Antisense & Nucleic Acid Drug Development* 6:133-139.
Krieg, A.M. (1998). "Leukocyte Stimulation by Oligodeoxynucleotides," Chapter 24 in *Applied Antisense Oligonucleotide Technology*, C.A. Stein and Arthur M. Krieg, eds., Wiley-Liss, Inc.: pp. 431-448.
Krieg A.M. et al. (1998a). "The Role of CpG Dinucleotides in DNA Vaccines," *Trends Microbiol.* 6:23-27.
Krieg A.M. et al. (1998b). "CpG DNA Induces Sustained IL-12 Expression In Vivo and Resistance to Listeria Monocytogenes Challenge," *J. Immunol.* 161:2428-2434.

Krieg A.M. et al. (1998c). "Sequence Motifs in Adenoviral DNA Block Immune Activation by Stimulatory CpG Motifs," *Proc. Natl. Acad. Sci. USA* 95:12631-12636.
Krieg, A.M. (1999). "CpG DNA: a novel immunomodulator," *Trends Microbiol.* 7(2):64-65.
Kullmann, W. (1987). *Enzymatic Peptide Synthesis*, CRC Press, Inc. Boca Raton, FL: (Table of Contents).
Latimer et al. (1995). "Specificity of Monoclonal Antibodies Produced Against Phosphorothioate and Ribo Modified DNAs," *Mol. Immunol.* 32(14/15):1057-1064.
Lea et al. (1996). "Cloning and Sequencing of cDNA's Encoding the Human Sperm Protein Sp17," *Biochem. Biophys. Acta* 1307:263-266.
Leclerc et al. (1997). "The Preferential Induction of a Th1 Immune Response by DNA-Based Immunization is Mediated by the Immunostimulatory Effect of Plasmid DNA," *Cell. Immunol.* 179:97-106.
Liang et al. (1996). "Activation of Human B Cells by Phosphorothioate Oligodeoxynucleotides," *The J. Clin. Invest* 98(5):1119-1129.
Lipford et al. (1997). "CpG-Containing Synthetic Oligonucleotides Promote B and Cytotoxic T Cell Responses to Protein Antigen: A New Class of Vaccine Adjuvants," *Eur. J. Immunol.* 27:2340-2344.
Lipford et al. (1997). "Immunostimulatory DNA: Sequence-dependent Production of Potentially Harmful or Useful Cytokines," *Eur. J. Immunol.* 27:3420-3426.
Liu et al. (1998). "Immunostimulatory CpG Oligodeoxynucleotides Enhance the Immune Response to Vaccine Strategies Involving Granulocyte-Macrophage Colony-Stimulating Factor," *Blood* 92(10):3730-3736.
Ludewig et al. (2001). "In Vivo Antigen Loading and Activation of Dendritic Cells via a Liposomal Peptide Vaccine Mediates Protective Antiviral and Anti-Tumour Immunity," *Vaccine* 19:23-32.
MacFarlane et al. (1997). "Unmethylated CpG-Containing Oligodeoxynucleotides Inhibit Apoptosis in WEHI 231 B Lymphocytes Induced by Several Agents: Evidence for Blockade of Apoptosis at a Distal Signalling Step," *Immunology* 91:586-593.
Malley. (1989). "The Immune Response of Offspring Mice from Mothers Immunized During Pregnancy with Protein Antigens," *J. Reprod. Immunol.* 16:173-186.
Manzel, L. et al. (1999). "Lack of Immune Stimulation by Immobilized CpG-Oligodeoxynucleotide," *Antisense Nucl. Acid Drug Dev.* 9:459-464.
Martin-Orozco et al. (1999). "Enhancement of antigen-presenting cell surface molecules involved in cognate interactions by immunostimulatory DNA sequences," *J. Immunol.* 11(7):1111-1118.
Matteucci, M. (1997). Oligonucleotide analogues: an overview *Oligonucleotides as Therapeutic Agents*, D.J. Chadwick and G. Cardew, eds., John Wiley and Sons, New York, NY:CIBA Foundation Symposium, pp. 5-18.
Mbawuike et al. (1994). "Influenza A Subtype Cross-Protection After Immunization of Outbred Mice with a Purified Chimeric NS1/HA2 Influenza Virus Protein," *Vaccine* 12(14):1340-1348.
McCluskie et al. (1998). "Cutting Edge: CpG DNA is a Potent Enhancer of Systemic and Mucosal Immune Responses Against Hepatitis B Surface Antigen with Intranasal Administration to Mice," *J. Immunol.* 161(9):4463-4466.
Miller, P.S. et al. (1971). "Synthesis and Properties of Adenine and Thymidine Nucleoside Alkyl Phosphotriesters, the Neutral Analogs of Dinucleoside Monophosphates," J. Am. Chem. Soc. 93(24):6657-6665.
Mishell, B.B. et al., eds. (1980). *Selected Methods in Cellular Immunology*. W.H. Freeman and Co.: San Francisco., pp. vii-xiv. (Table of Contents).
Mitragotri et al. (1995). "Ultrasound-Mediated Transdermal Protein Delivery," *Science* 269:850-853.
Mojcik et al. (1993). "Administration of a Phosphorothioate Oligonucleotide Antisense to Murine Endogenous Retroviral MCF env Causes Immune Effects in Vivo in a Sequence-Specific Manner," *Clin. Immuno. and Immunopathol.* 67(2):130-136.
Moldoveanu et al. (1998). "CpG DNA, a Novel Immune Enhancer for Systemic and Mucosal Immunization with Influenza Virus," *Vaccine* 16(11/12): 1216-1224.

(56) References Cited

OTHER PUBLICATIONS

Nelson, P.S. et al. (1989) "Bifunctional Oligonucleotide Probes Synthesized Using a Novel CPG Support are Able to Detect Single Base Pair Mutations," *Nucleic Acids Res.* 17(18):7187-7194.
Nelson et al. (1997). "N3'→P5' oligodeoxyribonucleotide phosphoramidates: A new method of synthesis based on a phosphoramidite amino-exchange reaction," *J. Org. Chem.* 62:7278-7287.
O'Hagen, D.T. (2001). "Recent Developments in Vaccine Delivery Systems," *Current Drug Targets—Infectious Disorders* 1(3):273-286.
O'Shannessy et al. (1985). "Specific Conjugation Reactions of the Oligosaccharide Moieties of Immunoglobulins," *J. Applied Biochem.* 7:347-355.
Pertmer et al. (1996). "Influenza Virus Nucleoprotein-Specific Immunoglobulin G Subclass and Cytokine Responses Elicited by DNA Vaccination are Dependent on the Route of Vector DNA Delivery," *J. Virol.* 70(9):6119-6125.
Peyrottes et al. (1996). "Oligodeoxynucleoside Phosphoramidates (P-NH$_2$): Synthesis and Thermal Stability of Duplexes with DNA and RNA Targets," *Nucleic Acids Res.* 24(10):1841-1848.
Pisetsky, D.S. et al. (1994). "Stimulation of Murine Lymphocyte Proliferation by a Phosphorothioate Oligonucleotide with Antisense Activity for Herpes Simplex Virus," *Life Sci.* 54(2):101-107.
Pisetsky et al. (1995). "Immunological properties of bacterial DNA," *Ann. N.Y. Acad. Sci.* 772:152-163.
Pisetsky (1996). "Immune Activation by Bacterial DNA: A New Genetic Code," *Immunity* 5:303-310.
Pisetsky (1996). "The Immunologic Properties of DNA," *J. Immunol.* 156:421-423.
Rafnar et al. (1991). "Cloning of Amb a 1 (Antigen E), the Major Allergen Family of Short Ragweed Pollen," *J. Biol. Chem.* 266(2):1229-1236.
Raz et al. (1994). "Intradermal gene immunization: The possible role of DNA uptake in the induction of cellular immunity to viruses," *Proc. Natl. Acad. Sci. USA* 91:9519-9523.
Raz et al. (1996). "Preferential induction of a Th$_1$ immune response and inhibition of specific IgE antibody formation by plasmid DNA immunization," *Proc. Natl. Acad. Sci. USA* 93:5141-5145.
Redford et al. (1998). "Cyclosporin A Enhances IL-12 Production by CpG Motifs in Bacterial DNA and Synthetic Oligodeoxynucleotides," *J. Immunol.* 161:3930-3935.
Rogers et al. (1993). "Recombinant Fel d 1: Expression, Purification, IgE Binding and Reaction with Cat-Allergic Human T Cells," *Mol. Immunol.* 30(6):559-568.
Roget et al. (1989). "Synthesis and Use of Labelled Nucleoside Phosphoramidite Building Blocks Bearing a Reporter Group: Biotinyl, Dinitrophenyl, Pyrenyl and Dansyl," *Nucleic Acids Res.* 17(19):7643-7651.
Romagnani, S. (2000). "T-Cell Subsets (Th1 versus Th2)," *Ann. Allergy Asthma Immunol.* 85(1):9-18.
Roman et al. (1997) ."Immunostimulatory DNA sequences function as T helper-1-promoting adjuvants" *Nature Medicine* 3(8):849-854.
Sato et al. (1996). "Immunostimulatory DNA Sequences Necessary for Effective Intradermal Gene Immunization," *Science* 273:352-354.
Schacht, E. et al. (1996). "Biomedical Applications of Degradable Polyphosphazenes," *Biotechnol. Bioeng.* 52(11):102-107.
Scherle et al. (1986). "Functional Analysis of Influenza-Specific Helper T Cell Clones In Vivo," *J. Exp. Med.* 164:1114-1128.
Scherle et al. (1988). "Differential Ability of B Cells Specific for External vs. Internal Influenza Virus Proteins to Respond to Help from Influenza Virus-Specific T-cell clones in vivo," *Proc. Natl. Acad. Sci. USA* 85:4446-4450.
Schultz et al. (1996). "Oligo-2'-fluoro-2'-deoxynucleotide N3'-P5' Phosphoramidates: Synthesis and Properties," *Nucleic Acids Res.* 24(15):2966-2973.
Schwartz et al. (1997). "CpG Motifs in Bacterial DNA Cause Inflammation in the Lower Respiratory Tract," *J. Clin. Invest.* 100:68-73.

Shimada et al. (1986). "In Vivo Augmentation of Natural Killer Cell Activity with a Deoxyribonucleic Acid Fraction of BCG," *Jpn. J. Cancer Res.* 77:808-816.
Sinah, N.D. et al. (1991). "Oligonucleotides with Reporter Groups Attached to the 5'-Terminus," Chapter 8 in *Oligonucleotide Analogues: A Practical Approach*, F. Eckstein, ed., IRL Press: pp. 185-210.
Singh et al. (1999). "Advances in Vaccine Adjuvants," *Nat. Biotech.* 17:1075-1081.
Sonehara et al. (1996). "Hexamer Palindromic Oligonucleotides with 5'-CG'3' Motif(s) Induce Production of Interferon," *J. Interferon and Cytokine Res.* 16:799-803.
Sparwasser et al. (1997). "Macrophages Sense Pathogens via DNA Motifs: Induction of Tumor Necrosis Factor-Alpha-Mediated Shock," *Eur. J. Immunol.* 27:1671-1679.
Spiegelberg et al. (1998). "Inhibition of IgE formation and allergic inflammation by allergen gene immunization and by CpG motif immunostimulatory oligodeoxynucleotides," *Allergy* 53:93-97.
Spiegelberg et al. (1999). "Inhibition of allergic inflammation in the lung by plasmid DNA allergen immunization," *Pediatr. Pulmonol.* Suppl.18:118-121.
Stacey et al. (1996). "Macrophages Ingest and Are Activated by Bacterial DNA," *J. Immunol.* 157:2116-2122.
Staros et al. (1986). "Enhancement by N-Hydroxysulfosucciniminde of Water-Soluble Carbodiimide-Mediated Coupling Reactions," *Analytical Biochemistry* 156:220-222.
Stein, C.A. et al. (1997). "Non-Antisense Effects of Oligodeoxynucleotides," Chapter 11 in *Antisense Technology*, C. Lichtenstein and W. Nellen, eds., IRL Press: pp. 241-264.
Stirchak et al. (1989). "Uncharged Stereoregular Nucleic Acid Analogs: 2. Morpholino Nucleoside Oligomers with Carbamate Internucleoside Linkages," *Nucleic Acids Res.* 17(15):6129-6141.
Supplementary European Search Report mailed Apr. 4, 2006 for European Patent Application No. 02761284.5, 4 pages.
Tamura et al. (1992). "Superior Cross-Protective Effect of Nasal Vaccination to Subcutaneous Inoculation with Influenza Hemagglutinin Vaccine," *Eur. J. Immunol.* 22:477-481.
Tamura et al. (1994). "Formulation of Inactivated Influenza Vaccines for Providing Effective Cross-Protection by Intranasal Vaccination in Mice," *Vaccine* 12(4):310-316.
Tokunaga et al. (1992)."Synthetic oligonucleotides with particular base sequences from the cDNA encoding proteins of *Mycobacterium bovis* BCG induce interferons and activate natural killer cells" *Microbiol. Immunol.* 36:55-66.
Tung et al. (1991). "Preparation of Oligonucleotide-Peptide Conjugates," *Bioconjug. Chem.* 2:464-465.
U.S. Appl. No. 12/243,915, filed Oct. 1, 2008, for Fearon et al.
Verthelyi, D. et al. (2001). "Human Peripheral Blood Cells Differentially Recognize and Respond to Two Distinct CpG Motifs," *J. Immunol.* 166(4):2372-2377.
Warner et al. (1984). "Construction and Evaluation of an Instrument for the Automated Synthesis of Oligodeoxyribonucleosides," *DNA* 3(5):401-411.
Weeratna et al. (1998). "Reduction of Antigen Expression from DNA Vaccines by Coadministered Oligodeoxymucleotides," *Antisense & Nucleic Acid Drug Development* 8:351-356.
Weeratna, R.D. et al. (2000). "CpG DNA Induces Stronger Immune Responses With Less Toxicity Than Other Adjuvants," *Vaccine* 18:1755-1762.
Weiner et al. (1997). "Immunostimulatory Oligodeoxynucleotides Containing the CpG Motif are Effective as Immune Adjuvants in Tumor Antigen Immunization," *Proc. Natl. Acad. Sci. USA* 94:10833-10837.
Widhe et al. (1998). "IgG Subclasses in Lyme Borreliosis: A Study of Specific IgG Subclass Distribution in a Interferon-K-Predominated Disease," *Scand. J. Immunol* 47: 575-581.
Wooldridge et al. (1997). "Immunostimulatory Oligodeoxynucleotides Containing CpG Motifs Enhance the Efficacy of Monoclonal Antibody Therapy of Lymphoma," *Blood* 89:2994-2998.
Yamamoto, S. et al. (1992). "Unique Palindromic Sequences in Synthetic Oligonucleotides are Required to Induce IFN [correction of

(56) References Cited

OTHER PUBLICATIONS

INF] and Augment IFN-Mediated [correction of INF] Natural Killer Activity," *J. Immunol.* 148(12):4072-4076.

Yamamoto, T. et al. (1994). "Ability of Oligonucleotides with Certain Palindromes to Induce Interferon Production and Augment Natural Killer Cell Activity is Associated with Their Base Length," *Antisense Research and Development* 4:119-122.

Yamamoto, T. et al. (1994). "Synthetic Oligonucleotides with Certain Palindromes Stimulate Interferon Production of Human Peripheral Blood Lymphocytes In Vitro," *Jpn. J. Cancer Res.* 85:775-779.

Yanagawa et al. (1988). "Analysis of Superhelical Structures of Nucleic Acid-Lipid Conjugates by Image Processing," *Nucleic Acids Ser. Symposium Series* 19:189-192.

Yi et al. (1996). "IFN-Gamma Promotes IL-6 and IgM Secretion in Response to CpG Motifs in Bacterial DNA and Oligodeoxynucleotides," *J. Immunol.* 156(2):558-564.

Yi et al. (1998). "CpG DNA Rescue from Anti-IgM-Induced WEHI-231 B Lymphoma Apoptosis via Modulation of IkB Alpha and IkB Beta and Sustained Activation of Nuclear Factor-*k*B/c-Rel," *J. Immunol.* 160(3):1240-1245.

Yi et al. (1998). "CpG Motifs in Bacterial DNA Activate Leukocytes Through the pH-Dependent Generation of Reactive Oxygen Species," *J. Immunol.* 160(2):4755-4761.

Yi et al. (1998). "CpG Oligodeoxyribonucleotides Rescue Mature Spleen B Cells from Spontaneous Apoptosis and Promote Cell Cycle Entry," *J. Immunol.* 160:5898-5906.

Yi et al. (1998). "Cutting Edge: Rapid Induction of Mitogen-Activated Protein Kinases by Immune Stimulatory CpG DNA," *J. Immunol.* 161:4493-4497.

Zhao et al. (1996). "Effect of Different Chemically Modified Oligodeoxynucleotides on Immune Stimulation," *Biochem. Pharmacol.* 51:173-182.

Zimmerman et al. (1998). "Cutting edge: CpG oligodeoxynucleotides trigger protective and curative TH1 responses in lethal murine leishmaniasis," 160:3627-3630.

Zon, G. (1993)."Chapter 8: Oligonucleoside phosphorothioates," *Protocols for Oligonucleotides and Analogs, Synthesis and Properties*, Agrawal, S. (ed.), Humana Press, pp. 165-189.

Zuckermann et al. (1987). "Efficient Methods for Attachment of Thiol Specific Probes to the 3'-Ends of Synthetic Oligodeoxyribonucleotides," *Nucleic Acids Res.* 15(214):5305-5321.

\* cited by examiner

```
                        SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Synthetic construct

<400> SEQUENCE: 1
tgactgtgaa ccttagagat ga                                           22

<210> SEQ ID NO 2
<211> LENGTH: 22
<212> TYPE: DNA
<213> ORGANISM: Artificial Sequence
<220> FEATURE:
<223> OTHER INFORMATION: Synthetic construct

<400> SEQUENCE: 2
tgactgtgaa cgttcgagat ga                                           22
```

IMMUNOMODULATORY COMPOSITIONS, FORMULATIONS, AND METHODS FOR USE THEREOF

REFERENCE TO RELATED APPLICATIONS

This application is a continuation application of U.S. patent application Ser. No. 10/214,799, filed Aug. 7, 2002, which claims priority under 35 U.S.C. §119(e) to U.S. Provisional Patent Applications Nos. 60/310,743, filed Aug. 7, 2001, and 60/335,263, filed Oct. 25, 2001, each of which are incorporated by reference in their entirety.

TECHNICAL FIELD

The present invention relates to immunomodulatory compositions comprising an immunomodulatory oligonucleotide (IMO) and methods of use thereof. In particular, the invention relates to immunomodulatory compositions comprising an IMO bound to a microparticle, where the IMO is three to six nucleotides in length. It also relates to the administration of the IMO/microcarrier complex to modulate at least one aspect of an immune response.

BACKGROUND ART

The type of immune response generated to infection or other antigenic challenge can generally be distinguished by the subset of T helper (Th) cells involved in the response. The Th1 subset is responsible for classical cell-mediated functions such as delayed-type hypersensitivity and activation of cytotoxic T lymphocytes (CTLs), whereas the Th2 subset functions more effectively as a helper for B-cell activation. The type of immune response to an antigen is generally influenced by the cytokines produced by the cells responding to the antigen. Differences in the cytokines secreted by Th1 and Th2 cells are believed to reflect different biological functions of these two subsets. See, for example, Romagnani (2000) *Ann. Allergy Asthma Immunol.* 85:9-18.

The Th1 subset may be particularly suited to respond to viral infections, intracellular pathogens, and tumor cells because it secretes IL-2 and IFN-γ, which activate CTLs. The Th2 subset may be more suited to respond to free-living bacteria and helminthic parasites and may mediate allergic reactions, since IL-4 and IL-5 are known to induce IgE production and eosinophil activation, respectively. In general, Th1 and Th2 cells secrete distinct patterns of cytokines and so one type of response can moderate the activity of the other type of response. A shift in the Th1/Th2 balance can result in an allergic response, for example, or, alternatively, in an increased CTL response.

For many infectious diseases, such as tuberculosis and malaria, Th2-type responses are of little protective value against infection. Proposed vaccines using small peptides derived from the target antigen and other currently used antigenic agents that avoid use of potentially infective intact viral particles, do not always elicit the immune response necessary to achieve a therapeutic effect. The lack of a therapeutically effective human immunodeficiency virus (HIV) vaccine is an unfortunate example of this failure. Protein-based vaccines typically induce Th2-type immune responses, characterized by high titers of neutralizing antibodies but without significant cell-mediated immunity.

Moreover, some types of antibody responses are inappropriate in certain indications, most notably in allergy where an IgE antibody response can result in anaphylactic shock. Generally, allergic responses also involve Th2-type immune responses. Allergic responses, including those of allergic asthma, are characterized by an early phase response, which occurs within seconds to minutes of allergen exposure and is characterized by cellular degranulation, and a late phase response, which occurs 4 to 24 hours later and is characterized by infiltration of eosinophils into the site of allergen exposure. Specifically, during the early phase of the allergic response, allergen cross-links IgE antibodies on basophils and mast cells, which in turn triggers degranulation and the subsequent release of histamine and other mediators of inflammation from mast cells and basophils. During the late phase response, eosinophils infiltrate into the site of allergen exposure (where tissue damage and dysfunction result).

Antigen immunotherapy for allergic disorders involves the subcutaneous injection of small, but gradually increasing amounts, of antigen. Such immunization treatments present the risk of inducing IgE-mediated anaphylaxis and do not efficiently address the cytokine-mediated events of the allergic late phase response. Thus far, this approach has yielded only limited success.

Administration of certain DNA sequences, generally known as immunostimulatory sequences or "ISS," induces an immune response with a Th1-type bias as indicated by secretion of Th1-associated cytokines. Administration of an immunostimulatory polynucleotide with an antigen results in a Th1-type immune response to the administered antigen. Roman et al. (1997) *Nature Med.* 3:849-854. For example, mice injected intradermally with *Escherichia coli* (*E. coli*) β-galactosidase (β-Gal) in saline or in the adjuvant alum responded by producing specific IgG1 and IgE antibodies, and CD4$^+$ cells that secreted IL-4 and IL-5, but not IFN-γ, demonstrating that the T cells were predominantly of the Th2 subset. However, mice injected intradermally (or with a tyne skin scratch applicator) with plasmid DNA (in saline) encoding β-Gal and containing an ISS responded by producing IgG2a antibodies and CD4$^+$ cells that secreted IFN-γ, but not IL-4 and IL-5, demonstrating that the T cells were predominantly of the Th1 subset. Moreover, specific IgE production by the plasmid DNA-injected mice was reduced 66-75%. Raz et al. (1996) *Proc. Natl. Acad. Sci. USA* 93:5141-5145. In general, the response to naked DNA immunization is characterized by production of IL-2, TNFα and IFN-γ by antigen-stimulated CD4$^+$ T cells, which is indicative of a Th1-type response. This is particularly important in treatment of allergy and asthma as shown by the decreased IgE production. The ability of immunostimulatory polynucleotides to stimulate a Th1-type immune response has been demonstrated with bacterial antigens, viral antigens and with allergens (see, for example, WO 98/55495).

Polynucleotides containing an unmethylated CpG dinucleotide have been found to have immunostimulatory activity. ISS oligonucleotides have been described as containing a core hexameric sequence of 5'-Purine, Purine, Cytosine, Guanine, Pyrimidine, Pyrimidine-3' (5'-RRCGYY-3'). While a number of disclosures refer to ISS oligonucleotides of six bases or longer (e.g. International Patent Application Nos. WO 97/28259, WO 98/16247 and WO 99/11275), other reports state that the ISS must be at least eight to ten nucleotides in length to have an immunostimulatory effect (see, e.g., Krieg et al. (1995) *Nature* 374:546-49 and International Patent Application No. 01/51500). International Patent Application No. WO 96/02555 indicates that the most effective ISS oligonucleotides contain either 5'-GACGTT-3' or 5'-GACGTC-3' within a larger oligonucleotide. More recently, International Patent Application No. WO 98/52962 has described three hexameric oligonucleotides, 5'-GACGTT-3',5'-GAGCTT-3', and 5'-TCCGGA-3', which are stated to have immunostimulatory effects. Liang et al. (*J. Clin. Invest.* 98:1119-29, 1996) disclose that the motif (TCG)$_n$, where n≥3, is a minimal stimulatory element for human cells.

An ISS-containing 27 base oligonucleotide bound to microparticles (SEPHAROSE® beads) has previously been shown to be as effective at in vitro immunostimulation as the same oligonucleotide in solution (Liang et al., ibid). Different results have been reported for ISS-containing oligonucleotides bound to gold, latex and magnetic particles; complexes with these materials were not active in stimulating proliferation of 7TD1 cells, which proliferate in response to ISS-containing oligonucleotides (Manzel et al. (1999) *Antisense Nucl. Acid Drug Dev.* 9:459-464).

Other references describing ISS include: Krieg et al. (1989) *J. Immunol.* 143:2448-2451; Tokunaga et al. (1992) *Microbiol. Immunol.* 36:55-66; Kataoka et al. (1992) *Jpn. J. Cancer Res.* 83:244-247; Yamamoto et al. (1992) *J. Immunol.* 148:4072-4076; Mojcik et al. (1993) *Clin. Immuno. and Immunopathol.* 67:130-136; Branda et al. (1993) *Biochem. Pharmacol.* 45:2037-2043; Pisetsky et al. (1994) *Life Sci.* 54(2):101-107; Yamamoto et al. (1994a) *Antisense Research and Development.* 4:119-122; Yamamoto et al. (1994b) *Jpn. J. Cancer Res.* 85:775-779; Raz et al. (1994) *Proc. Natl. Acad. Sci. USA* 91:9519-9523; Kimura et al. (1994) *J. Biochem.* (Tokyo) 116:991-994; Pisetsky et al. (1995) *Ann. N.Y. Acad. Sci.* 772:152-163; Pisetsky (1996a) *J. Immunol.* 156: 421-423; Pisetsky (1996b) *Immunity* 5:303-310; Zhao et al. (1996) *Biochem. Pharmacol.* 51:173-182; Yi et al. (1996) *J. Immunol.* 156:558-564; Krieg (1996) *Trends Microbiol.* 4(2): 73-76; Krieg et al. (1996) *Antisense Nucleic Acid Drug Dev.* 6:133-139; Klinman et al. (1996) *Proc. Natl. Acad. Sci. USA.* 93:2879-2883; Raz et al. (1996); Sato et al. (1996) *Science* 273:352-354; Stacey et al. (1996) *J. Immunol.* 157:2116-2122; Ballas et al. (1996) *J. Immunol.* 157:1840-1845; Branda et al. (1996) *J. Lab. Clin. Med.* 128:329-338; Sonehara et al. (1996) *J. Interferon and Cytokine Res.* 16:799-803; Klinman et al. (1997) *J. Immunol.* 158:3635-3639; Sparwasser et al. (1997) *Eur. J. Immunol.* 27:1671-1679; Roman et al. (1997); Carson et al. (1997) *J. Exp. Med.* 186:1621-1622; Chace et al. (1997) *Clin. Immunol. and Immunopathol.* 84:185-193; Chu et al. (1997) *J. Exp. Med.* 186:1623-1631; Lipford et al. (1997a) *Eur. J. Immunol.* 27:2340-2344; Lipford et al. (1997b) *Eur. J. Immunol.* 27:3420-3426; Weiner et al. (1997) *Proc. Natl. Acad. Sci. USA* 94:10833-10837; Macfarlane et al. (1997) *Immunology* 91:586-593; Schwartz et al. (1997) *J. Clin. Invest.* 100:68-73; Stein et al. (1997) *Antisense Technology*, Ch. 11 pp. 241-264, C. Lichtenstein and W. Nellen, Eds., IRL Press; Wooldridge et al. (1997) *Blood* 89:2994-2998; Leclerc et al. (1997) *Cell. Immunol.* 179:97-106; Kline et al. (1997) *J. Invest. Med.* 45(3):282A; Yi et al. (1998a) *J. Immunol.* 160:1240-1245; Yi et al. (1998b) *J. Immunol.* 160:4755-4761; Yi et al. (1998c) *J. Immunol.* 160: 5898-5906; Yi et al. (1998d) *J. Immunol.* 161:4493-4497; Krieg (1998) *Applied Antisense Oligonucleotide Technology* Ch. 24, pp. 431-448, C. A. Stein and A. M. Krieg, Eds., Wiley-Liss, Inc.; Krieg et al. (1998a) *Trends Microbiol.* 6:23-27; Krieg et al. (1998b) *J. Immunol.* 161:2428-2434; Krieg et al. (1998c) *Proc. Natl. Acad. Sci. USA* 95:12631-12636; Spiegelberg et al. (1998) *Allergy* 53(455):93-97; Horner et al. (1998) *Cell Immunol.* 190:77-82; Jakob et al. (1998) *J. Immunol.* 161:3042-3049; Redford et al. (1998) *J. Immunol.* 161: 3930-3935; Weeratna et al. (1998) *Antisense & Nucleic Acid Drug Development* 8:351-356; McCluskie et al. (1998) *J. Immunol.* 161(9):4463-4466; Gramzinski et al. (1998) *Mol. Med.* 4:109-118; Liu et al. (1998) *Blood* 92:3730-3736; Moldoveanu et al. (1998) *Vaccine* 16: 1216-1224; Brazolot Milan et al. (1998) *Proc. Natl. Acad. Sci. USA* 95:15553-15558; Briode et al. (1998) *J. Immunol.* 161:7054-7062; Briode et al. (1999) *Int. Arch. Allergy Immunol.* 118:453-456; Kovarik et al. (1999) *J. Immunol.* 162:1611-1617; Spiegelberg et al. (1999) *Pediatr. Pulmonol. Suppl.* 18:118-121; Martin-Orozco et al. (1999) *Int. Immunol.* 11:1111-1118; EP 468,520; WO 96/02555; WO 97/28259; WO 98/16247; WO 98/18810; WO 98/37919; WO 98/40100; WO 98/52581; WO 98/55495; WO 98/55609 and WO 99/11275. See also Elkins et al. (1999) *J. Immunol.* 162:2291-2298, WO 98/52962, WO 99/33488, WO 99/33868, WO 99/51259 and WO 99/62923. See also Zimmermann et al. (1998) *J. Immunol.* 160:3627-3630; Krieg (1999) *Trends Microbiol.* 7:64-65; U.S. Pat. Nos. 5,663,153, 5,723,335, 5,849,719 and 6,174,872. See also WO 99/56755, WO 00/06588, WO 00/16804; WO 00/21556; WO 00/67023 and WO 01/12223. See also WO 00/54803; WO 00/61161; WO 01/15726; WO 01/22972, WO 01/22990; WO 01/35991; WO 01/51500; WO 01/54720; U.S. Pat. Nos. 6,194,388, 6,207,646, 6,214,806, 6,239,116 and Verthelyi et al. (2001) *J. Immunol.* 166:2372-2377.

Additionally, Godard et al. (1995) *Eur. J. Biochem.* 232: 404-410, discloses cholesterol-modified antisense oligonucleotides bound to poly(isohexylcyanoacrylate) nanoparticles.

All patents, patent applications, and publications cited herein are hereby incorporated by reference in their entirety.

DISCLOSURE OF THE INVENTION

The invention relates to new compositions and methods for modulating immune responses in individuals, especially human individuals.

In one aspect, the invention relates to compositions which comprise immunomodulatory oligonucleotide/microcarrier (IMO/MC) complexes and encapsulates. An IMO/MC complex or encapsulate comprises a trimer, quatramer, pentamer, or hexamer (3-6mer) immunomodulatory oligonucleotide (IMO) having a sequence according to the formula 5'-$X_1$CG$X_2$-3', where $X_1$ is zero to four nucleotides, $X_2$ is zero to four nucleotides and excludes the sequences 5'-GACGTT-3',5'-TCCGGA-3', and 5'-GAGCTT-3'. Preferably, the IMO is a 3-6mer having a sequence according to the formula 5'-$X_1$TCG$X_2$-3' or 5'-$X_1$UCG$X_2$-3', where $X_1$ is zero to two nucleotides and $X_2$ is zero to three nucleotides, linked to an insoluble microcarrier (MC) which may be either biodegradable or nonbiodegradable. More preferably, the IMO/MC complexes and encapsulates of the invention comprise IMOs having the sequence 5'-$X_1$TCG$X_2$-3' or 5'-$X_1$UCG$X_2$-3', where $X_1$ is zero or one nucleotide, and $X_2$ is zero to three nucleotides and the IMO is no longer than six nucleotides. In certain embodiments, the complex or encapsulate does not comprise a oligonucleotide greater than six nucleotides in length. The IMO may be covalently or non-covalently linked to the microcarrier in the complex, and the IMO may be modified to facilitate complex formation. Microcarriers used in IMO/MC complexes are typically solid phase microcarriers, although liquid phase microcarriers (e.g., an oil in water emulsion comprising a polymer or oil, preferably a biodegradable polymer or oil) are also contemplated. Microcarriers are generally less than about 150, 120 or 100 μm in size, more commonly less than about 50-60 μm in size, and may be about 10 nm to about 10 μm or about 25 nm to 5 μm in size. In certain embodiments, the compositions of the invention comprise an IMO/MC complex or encapsulate and a pharmaceutically acceptable excipient. In certain embodiments, the compositions of the invention comprise an antigen-free IMO/MC complex or encapsulate, i.e., an IMO/MC complex or encapsulate not linked to an antigen (either directly or indirectly).

In another aspect, the invention relates to methods of modulating an immune response in an individual, comprising administering to an individual an IMO/MC complex or encapsulate in an amount sufficient to modulate an immune response in said individual. Immunomodulation according to the methods of the invention may be practiced on individuals including those suffering from a disorder associated with a Th2-type immune response (e.g., allergies or allergy-induced asthma), individuals receiving vaccines such as therapeutic vaccines (e.g., vaccines comprising an allergy epitope, a mycobacterial epitope, or a tumor associated epitope) or prophylactic vaccines, individuals with cancer, individuals having an infectious disease and individuals at risk of exposure to an infectious agent.

In a further aspect, the invention relates to methods of increasing interferon-gamma (IFN-γ) in an individual, comprising administering an effective amount of an IMO/MC complex or encapsulate to the individual. Administration of an IMO/MC complex or encapsulate in accordance with the invention increases IFN-γ in the individual. Suitable subjects for these methods include those individuals having idiopathic pulmonary fibrosis (IPF), scleroderma, cutaneous radiation-induced fibrosis, hepatic fibrosis including schistosomiasis-induced hepatic fibrosis, renal fibrosis as well as other conditions which may be improved by administration of IFN-γ.

In another aspect, the invention relates to methods of increasing IFN-α in an individual, comprising administering an effective amount of an IMO/MC complex or encapsulate to the individual. Administration of an IMO/MC complex or encapsulate in accordance with the invention increases IFN-α levels in the individual. Suitable subjects for these methods include those individuals having disorders which respond to the administration of IFN-α, including viral infections and cancer.

In another aspect, the invention relates to methods of ameliorating one or more symptoms of an infectious disease, comprising administering an effective amount of an IMO/MC complex or encapsulate to an individual having an infectious disease. Administration of an IMO/MC complex or encapsulate in accordance with the invention ameliorates one or more symptoms of the infectious disease. The infectious diseases which may be treated in accordance with the invention include infectious diseases caused by a cellular pathogen (e.g., a mycobacterial disease, malaria, leishmaniasis, toxoplasmosis, schistosomiasis or clonorchiasis), and may include or exclude viral diseases.

The invention further relates to kits for carrying out the methods of the invention. The kits of the invention comprise a container comprising an IMO/MC complex or encapsulate and may also contain instructions for use of the IMO/MC complex or encapsulate in immunomodulation of an individual, for example when the individual suffers from a disorder associated with a Th2-type immune response (e.g., allergies or allergy-induced asthma), is receiving vaccines such as therapeutic vaccines (e.g., vaccines comprising an allergy epitope, a mycobacterial epitope, or a tumor associated epitope) or prophylactic vaccines, suffers from cancer, suffers from an infectious disease or is at risk of exposure to an infectious agent.

MODES OF PRACTICING THE INVENTION

We have discovered new compositions and methods for modulating immune responses in individuals, especially human individuals. The compositions of the invention comprise an immunomodulatory oligonucleotide (IMO) complexed with or encapsulated in an insoluble microcarrier (MC). Contrary to teachings in the art which state that an immomodulatory oligonucleotide must be at least eight nucleotides in length to be effective, we have found that IMOs from three to six bases in length modulate immune cells, including human cells, when combined with microcarriers. IMOs of the instant invention are 3-6mers and have a sequence according to the formula 5'-$X_1CGX_2$-3', where $X_1$ is zero to four nucleotides, $X_2$ is zero to four nucleotides, excluding the sequences 5'-GACGTT-3',5'-TCCGGA-3', and 5'-GAGCTT-3'. Preferably, the IMO is a 3-6mer having a sequence according to the formula 5'-$X_1TCGX_2$-3' or 5'-$X_1UCGX_2$-3', where $X_1$ is zero to two nucleotides and $X_2$ is zero to three nucleotides, linked to an insoluble microcarrier (MC). More preferably, the IMO/MC complexes or encapsulates of the invention comprise IMOs having the sequence 5'-$X_1TCGX_2$-3' or 5'-$X_1UCGX_2$-3', where $X_1$ is zero or one nucleotide, and $X_2$ is zero to three nucleotides and the IMO is no longer than six nucleotides. In other preferred embodiments, the IMO/MC complexes or encapsulates comprise an IMO having the sequence 5'-$X_1TCGX_2$-3' or 5'-$X_1UCGX_2$-3', where $X_1$ is zero or one nucleotide and $X_2$ is two to three nucleotides and the IMO is no longer than six nucleotides.

The IMO/MC complexes or encapsulates may include or exclude an antigen. In some embodiments, the invention provides compositions comprising antigen-free IMO/MC complexes or encapsulates, i.e., IMO/MC complexes or encapsulates neither linked to (directly or indirectly) nor mixed with an antigen. In other embodiments, the invention provides compositions comprising IMO/MC complexes or encapsulates mixed with one or more antigens. In other embodiments, the invention provides compositions comprising IMO/MC complexes or encapsulates linked to antigen.

The immunomodulatory oligonucleotide/microcarrier (IMO/MC) complexes of the invention may be covalently or non-covalently linked, and comprise a microcarrier (e.g., a water-insoluble carrier of less than about 150 μm size) that is insoluble in water. Microcarriers may be biodegradable or nonbiodegradable, and are generally solid phase (e.g., polylactic acid beads), although liquid phase microcarriers (e.g., an oil in water emulsion comprising a biodegradable polymer or oil, preferably a biodegradable polymer or oil) are also useful. The IMO may be modified to allow or augment binding to the MC (e.g., by incorporation of a free sulfhydryl for covalent crosslinking or addition of a hydrophobic moiety such as cholesterol for hydrophobic bonding).

The invention provides new compositions comprising an IMO covalently linked to a microcarrier to form a covalent IMO/MC complex. Linkage between the IMO and MC may be direct (e.g., via a disulfide bond between sulfhydryls on the IMO and MC) or the constituents may be linked by a crosslinking moiety of one or more atoms separating the bonds to the IMO and MC.

Also provided are compositions comprising an IMO non-covalently linked to a microcarrier to provide a non-covalent IMO/MC complex. Non-covalent IMO/MC complexes generally comprise an IMO that has been modified to allow binding to the microcarrier (e.g., by addition of a cholesterol moiety to the IMO to allow hydrophobic binding to oil or lipid based microcarrier), although the properties of the native IMO may be used to bind to the microcarrier (e.g., electrostatic binding to a cationic microcarrier such as cationic poly (lactic acid, glycolic acid) copolymer).

The invention also provides methods for modulating an immune response in an individual by administering an IMO/MC complex or encapsulate to the individual.

Further provided are kits for practicing the methods of the invention. The kits comprise a package or container comprising IMO/MC complex or encapsulate and may also contain instructions for administering an IMO/MC complex or encapsulate for immunomodulation in a subject.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *The Immunoassay Handbook* (D. Wild, ed., Stockton Press NY, 1994); *Bioconjugate Techniques* (Greg T. Hermanson, ed., Academic Press, 1996); and *Methods of Immunological Analysis* (R. Masseyeff, W. H. Albert, and N. A. Staines, eds., Weinheim: VCH Verlags gesellschaft mbH, 1993).

DEFINITIONS

As used herein, the singular form "a", "an", and "the" includes plural references unless indicated otherwise. For example, "an" IMO includes one or more IMO.

As used herein, the term "oligonucleotide" includes single-stranded DNA (ssDNA), double-stranded DNA (dsDNA), single-stranded RNA (ssRNA) and double-stranded RNA (dsRNA), modified oligonucleotides and oligonucleosides or combinations thereof. The oligonucleotide can be linearly or circularly configured. Oligonucleotides are polymers of nucleosides joined, generally, through phosphodiester linkages, although alternate linkages, such as phosphorothioate esters may also be used in oligonucleotides, exclusively or in combination with phosphodiester bonds. A nucleoside consists of a purine (adenine or guanine or derivative thereof, such as inosine) or pyrimidine (thymine, cytosine or uracil, or derivative thereof) base bonded to a sugar. The four nucleoside units (or bases) in DNA are called deoxyadenosine, deoxyguanosine, deoxythymidine, and deoxycytidine. Additionally, deoxyinosine and deoxyuridine may be incorporated into DNA. A nucleotide is a phosphate ester of a nucleoside.

The terms "immunomodulatory oligonucleotide" and "IMO", as used herein, are interchangeable and refer to an oligonucleotide having a sequence that, when bound to a microcarrier, effects a measurable immune response as measured in vitro, in vivo and/or ex vivo (i.e., is active when complexed with or encapsulated in a microcarrier). Examples of measurable immune responses include, but are not limited to, antigen-specific antibody production, secretion of cytokines, activation or expansion of lymphocyte populations such as NK cells, CD4+ T lymphocytes, CD8+ T lymphocytes, B lymphocytes, and the like. Preferably, the IMO sequences preferentially activate a Th1-type response. An IMO is a 3-6mer oligonucleotide having the sequence 5'-$X_1$CG$X_2$-3', where $X_1$ is zero to four nucleotides, $X_2$ is zero to four nucleotides and excludes the sequences 5'-GACGTT-3',5'-TCCGGA-3', and 5'-GAGCTT-3'.

The phrase "cytosine of the core trimer of the IMO" refers to the cytosine of the core trimer 5'-TCG-3' or 5'-UCG-3' of those IMOs fitting the sequence formula 5'-$X_1$TCG$X_2$-3' and 5'-$X_1$UCG$X_2$-3', where $X_1$ is zero to two nucleotides and $X_2$ is zero to four nucleotides. As is apparent from this structural formula, the "cytosine of the core trimer" of the IMO 5'-TCGTCG-3' is located at position two (e.g., the penultimate base at the 5' end).

The term "microcarrier" refers to a particulate composition which is insoluble in water and which has a size of less than about 150, 120, 100 μm or less than about 50-60 μm, preferably less than about 10, 5, 2.5, 2 or 1.5 μm. Microcarriers include "nanocarriers", which are microcarriers that have a size of less than about 1 μm, preferably less than about 500 nm. Solid phase microcarriers may be particles formed from biocompatible naturally occurring polymers, synthetic polymers or synthetic copolymers, which may include or exclude microcarriers formed from agarose or cross-linked agarose, as well as other materials known in the art. Microcarriers for use in the instant invention may be biodegradable or nonbiodegradable. Biodegradable solid phase microcarriers may be formed from polymers which are degradable (e.g., poly(lactic acid), poly(glycolic acid) and copolymers thereof) or erodible (e.g., poly(ortho) esters such as 3,9-diethylidene-2,4,8,10-tetraoxaspiro[5.5]undecane (DETOSU), polymethylidene malonate, or poly(anhydrides), such as poly (anhydrides) of sebacic acid) under mammalian physiological conditions. Nonbiodegradable microcarriers may be formed from materials which are non-erodible and/or non-degradable under mammalian physiological conditions, such as organic polymers including polystyrene, polypropylene, polyacrylamide, latex, and dextran, inorganic materials including inorganic crystalline materials such as silica, hydroxyapatite, alum, and calcium phosphate, as well as ceramics, gold, and ferromagnetic and paramagnetic materials. Microcarriers may also be liquid phase (e.g., oil or lipid based), such as liposomes, ISCOMs (immune-stimulating complexes, which are stable complexes of cholesterol, phospholipid, and adjuvant-active saponin) without antigen, or droplets or micelles found in oil in water or water in oil emulsions, provided the liquid phase microcarriers are biodegradable. Biodegradable liquid phase microcarriers typically incorporate a biodegradable oil, a number of which are known in the art, including squalene and vegetable oils. Microcarriers are typically spherical in shape, but microcarriers which deviate from spherical shape are also acceptable (e.g., ellipsoid, rod-shaped, etc.). Due to their insoluble nature (with respect to water), microcarriers are filterable from water and water-based (aqueous) solutions.

The "size" of a microcarrier is generally the "design size" or intended size of the particles stated by the manufacturer. Size may be a directly measured dimension, such as average or maximum diameter, or may be determined by an indirect assay such as a filtration screening assay. Direct measurement of microcarrier size is typically carried out by microscopy, generally light microscopy or scanning electron microscopy (SEM), in comparison with particles of known size or by reference to a micrometer. As minor variations in size arise during the manufacturing process, microcarriers are considered to be of a stated size if measurements show the microcarriers are ±about 5-10% of the stated measurement. Size characteristics may also be determined by dynamic light scattering or obscuration techniques. Alternately, microcarrier size may be determined by filtration screening assays. A microcarrier is less than a stated size if at least 97% of the particles pass through a "screen-type" filter (i.e., a filter in which retained particles are on the surface of the filter, such as polycarbonate or polyethersulfone filters, as opposed to a "depth filter" in which retained particles lodge within the filter) of the stated size. A microcarrier is larger than a stated size if at least about 97% of the microcarrier particles are retained by a screen-type filter of the stated size. Thus, at least about 97% microcarriers of about 10 µm to about 10 nm in size pass through a 10 µm pore screen filter and are retained by a 10 nm screen filter.

As above discussion indicates, reference to a size or size range for a microcarrier implicitly includes approximate variations and approximations of the stated size and/or size range. This is reflected by use of the term "about" when referring to a size and/or size range, and reference to a size or size range without reference to "about" does not mean that the size and/or size range is exact.

A microcarrier is considered "biodegradable" if it is degradable or erodible under normal mammalian physiological conditions. Generally, a microcarrier is considered biodegradable if it is degraded (i.e., loses at least 5% of its mass and/or average polymer length) after a 72 hour incubation at 37° C. in normal human serum. Accordingly, and conversely, a microcarrier is considered "nonbiodegradable" if it is not degraded or eroded under normal mammalian physiological conditions. Generally, a microcarrier is considered nonbiodegradable if it not degraded (i.e., loses less than 5% of its mass and/or average polymer length) after at 72 hour incubation at 37° C. in normal human serum.

The term "immunomodulatory oligonucleotide/microcarrier complex" or "IMO/MC complex" refers to a complex of an IMO and a microcarrier of the invention, wherein the IMO is not encapsulated in the MC. The components of the complex may be covalently or non-covalently linked. Non-covalent linkages may be mediated by any non-covalent bonding force, including by hydrophobic interaction, ionic (electrostatic) bonding, hydrogen bonds and/or van der Waals attractions. In the case of hydrophobic linkages, the linkage is generally via a hydrophobic moiety (e.g., cholesterol) covalently linked to the IMO. Preferably, the IMO/MC complex is insoluble in pure water.

The term "immunomodulatory" or "modulating an immune response" as used herein includes immunostimulatory as well as immunosuppressive effects. Immunomodulation is primarily a qualitative alteration in an overall immune response, although quantitative changes may also occur in conjunction with immunomodulation. An example of an immune response that is immunomodulated according to the present invention is one that is shifted towards a "Th1-type" immune response, as opposed to a "Th2-type" immune response. Th1-type responses are typically considered cellular immune system (e.g., cytotoxic lymphocytes) responses, while Th2-type responses are generally "humoral", or antibody-based. Th1-type immune responses are normally characterized by "delayed-type hypersensitivity" reactions to an antigen, and can be detected at the biochemical level by increased levels of Th1-associated cytokines such as IFN-γ, IL-2, IL-12, and TNF-β, as well as IFN-α and IL-6, although IL-6 may also be associated with Th2-type responses as well. Th1-type immune responses are generally associated with the production of cytotoxic lymphocytes (CTLs). Th2-type immune responses are generally associated with higher levels of antibody production, including IgE production, an absence of or minimal CTL production, as well as expression of Th2-associated cytokines such as IL-4. Accordingly, immunomodulation in accordance with the invention may be recognized by, for example, an increase in IFN-γ and/or a decrease in IgE production in an individual treated in accordance with the methods of the invention as compared to the absence of treatment.

The term "conjugate" refers to a complex in which an IMO, an MC and/or an IMO/MC complex are linked to an antigen (via either the IMO or the MC or both). Such conjugate linkages include covalent and/or non-covalent linkages. The linkage may be direct (e.g., a bond between one or more atoms of the IMO and one or more atoms of the antigen) or via a linker arm containing moieties which bind to conjugate partners (e.g., the IMO and antigen or the MC and the antigen), thereby linking the conjugate partners (e.g., such as by use of biotin and avidin to enable high affinity bonding between the IMO and the antigen or by use of a crosslinking agent that incorporates a spacer arm).

The term "antigen" means a substance that is recognized and bound specifically by an antibody or by a T cell antigen receptor. Antigens can include peptides, proteins, glycoproteins, polysaccharides, complex carbohydrates, sugars, gangliosides, lipids and phospholipids; portions thereof and combinations thereof. The antigens can be those found in nature or can be synthetic. Antigens suitable for administration with the IMO/MC complexes or encapsulates of the invention include any molecule capable of eliciting a B cell or T cell antigen-specific response. Preferably, antigens elicit an antibody response specific for the antigen. Haptens are included within the scope of "antigen." A hapten is a low molecular weight compound that is not immunogenic by itself but is rendered immunogenic when conjugated with an immunogenic molecule containing antigenic determinants. Small molecules may need to be haptenized in order to be rendered antigenic. Preferably, antigens of the present invention include peptides, lipids (e.g. sterols, fatty acids, and phospholipids), polysaccharides such as those used in *Hemophilus influenza* vaccines, gangliosides and glycoproteins.

"Adjuvant" refers to a substance which, when added to an immunogenic agent such as antigen, nonspecifically enhances or potentiates an immune response to the agent in the recipient host upon exposure to the mixture.

The term "peptide" refers to polypeptides that are of sufficient length and composition to effect a biological response, e.g. antibody production or cytokine activity whether or not the peptide is a hapten. Typically, the peptides are at least six amino acid residues in length. The term "peptide" further includes modified amino acids (whether or not naturally or non-naturally occurring), such modifications including, but not limited to, phosphorylation, glycosylation, pegylation, lipidization and methylation.

"Antigenic peptides" can include purified native peptides, synthetic peptides, recombinant peptides, crude peptide extracts, or peptides in a partially purified or unpurified active state (such as peptides that are a part of attenuated or inactivated viruses, cells, or micro-organisms), or fragments of such peptides. An "antigenic peptide" or "antigen polypeptide" accordingly means all or a portion of a polypeptide which exhibits one or more antigenic properties. Thus, for example, an "Amb a 1 antigenic polypeptide" or "Amb a 1 polypeptide antigen" is an amino acid sequence from Amb a 1, whether the entire sequence, a portion of the sequence, and/or a modification of the sequence, which exhibits an antigenic property (i.e., binds specifically to an antibody or a T cell receptor).

A "delivery molecule" or "delivery vehicle" is a chemical moiety which facilitates, permits, and/or enhances delivery of an IMO/MC complex or encapsulate to a particular site and/or with respect to particular timing. A delivery vehicle may or may not additionally stimulate an immune response.

An "allergic response to antigen" means an immune response generally characterized by the generation of eosinophils and/or antigen-specific IgE and their resultant effects. As is well-known in the art, IgE binds to IgE receptors on mast cells and basophils. Upon later exposure to the antigen recognized by the IgE, the antigen cross-links the IgE on the mast cells and basophils causing degranulation of these cells, including, but not limited, to histamine release. It is understood and intended that the terms "allergic response to antigen", "allergy", and "allergic condition" are equally appropriate for application of some of the methods of the invention. Further, it is understood and intended that the methods of the invention include those that are equally appropriate for prevention of an allergic response as well as treating a pre-existing allergic condition.

As used herein, the term "allergen" means an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic (e.g., IgE) immune response upon exposure to the molecule. A number of isolated allergens are known in the art. These include, but are not limited to, those provided in Table 1 herein.

The term "desensitization" refers to the process of the administration of increasing doses of an allergen to which the subject has demonstrated sensitivity. Examples of allergen doses used for desensitization are known in the art, see, for example, Fornadley (1998) *Otolaryngol. Clin. North Am.* 31:111-127.

"Antigen-specific immunotherapy" refers to any form of immunotherapy which involves antigen and generates an antigen-specific modulation of the immune response. In the allergy context, antigen-specific immunotherapy includes, but is not limited to, desensitization therapy.

An "individual" is a vertebrate, preferably a mammal, more preferably a human. Mammals include, but are not limited to, humans, primates, farm animals, sport animals, rodents and pets. Vertebrates also include, but are not limited to, birds (i.e., avian individuals) and reptiles (i.e., reptilian individuals).

An individual is considered "at risk" for a particular disorder if the individual has an increased likelihood of acquiring the disorder. With regards to infectious diseases, an individual is at risk if he is exposed to the pathogen which causes the disease (e.g., by close association with an infectious individual) or is at high risk of being exposed to the pathogen which causes the disease (e.g., by travelling or residing in a locale in which the pathogen is prevalent, such as an area in which malaria is endemic). An individual is at risk of a non-infectious disease (e.g., cancer, asthma, allergies) when the individual's heredity or environment increases the individual's risk of acquiring the disorder to at least twice that of the general population. Examples of individuals at risk for non-infectious disorders include women with BRCA1 mutations (breast cancer), individuals with FPC mutations (colon cancer), individuals having at least one first degree relative with lung cancer, and individuals having at least one first degree relative with allergies (allergies).

An "effective amount" or a "sufficient amount" of a substance is that amount sufficient to effect beneficial or desired results, including clinical results, and, as such, an "effective amount" depends upon the context in which it is being applied. In the context of administering a composition that modulates an immune response to an antigen, an effective amount of an IMO/MC complex or encapsulate is an amount sufficient to achieve such a modulation as compared to the immune response obtained when the antigen is administered alone. An effective amount can be administered in one or more administrations.

The term "co-administration" as used herein refers to the administration of at least two different substances sufficiently close in time to modulate an immune response. Preferably, co-administration refers to simultaneous administration of at least two different substances.

"Stimulation" of an immune response, such as Th1 response, means an increase in the response, which can arise from eliciting and/or enhancement of a response.

An "IgE associated disorder" is a physiological condition which is characterized, in part, by elevated IgE levels, which may or may not be persistent. IgE associated disorders include, but are not limited to, allergy and allergic reactions, allergy-related disorders (described below), asthma, rhinitis, conjunctivitis, urticaria, shock, *Hymenoptera* sting allergies, drug allergies, and parasite infections. The term also includes related manifestations of these disorders. Generally, IgE in such disorders is antigen-specific.

An "allergy-related disorder" means a disorder resulting from the effects of an antigen-specific IgE immune response. Such effects can include, but are not limited to, hypotension and shock. Anaphylaxis is an example of an allergy-related disorder during which histamine released into the circulation causes vasodilation as well as increased permeability of the capillaries with resultant marked loss of plasma from the circulation. Anaphylaxis can occur systemically, with the associated effects experienced over the entire body, and it can occur locally, with the reaction limited to a specific target tissue or organ.

The term "viral disease", as used herein, refers to a disease which has a virus as its etiologic agent. Examples of viral diseases include hepatitis B, hepatitis C, influenza, acquired immunodeficiency syndrome (AIDS), and herpes zoster.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or the time course of the progression is slowed or lengthened, as compared to not treating the disorder. Especially in the allergy context, as is well understood by those skilled in the art, palliation may occur upon modulation of the immune response against an allergen(s). Further, palliation does not necessarily occur by administration of one dose, but often occurs upon administration of a series of doses. Thus, an amount sufficient to palliate a response or disorder may be administered in one or more administrations.

An "antibody titer", or "amount of antibody", which is "elicited" by an IMO/MC complex or encapsulate refers to the amount of a given antibody measured at a time point after administration of IMO/MC complex or encapsulate.

A "Th1-associated antibody" is an antibody whose production and/or increase is associated with a Th1 immune response. For example, IgG2a is a Th1-associated antibody in mouse. For purposes of this invention, measurement of a Th1-associated antibody can be measurement of one or more such antibodies. For example, in human, measurement of a Th1-associated antibody could entail measurement of IgG1 and/or IgG3.

A "Th2-associated antibody" is an antibody whose production and/or increase is associated with a Th2 immune response. For example, IgG1 is a Th2-associated antibody in mouse. For purposes of this invention, measurement of a Th2-associated antibody can be measurement of one or more such antibodies. For example, in human, measurement of a Th2-associated antibody could entail measurement of IgG2 and/or IgG4.

To "suppress" or "inhibit" a function or activity, such as cytokine production, antibody production, or histamine release, is to reduce the function or activity when compared to otherwise same conditions except for a condition or parameter of interest, or alternatively, as compared to another condition. For example, an IMO/MC complex or encapsulate administered with an antigen or including an antigen which suppresses histamine release or reduces histamine release as compared to, for example, histamine release induced by antigen alone.

As used herein, the term "comprising" and its cognates are used in their inclusive sense; that is, equivalent to the term "including" and its corresponding cognates.

The instant disclosure uses single letters to indicate bases of a nucleotide sequence, where A is adenine, G is guanine, C is cytosine, T is thymine, U is uracil, I is inosine, R is a purine, and Y is a pyrimidine.

Compositions of the Invention

The invention provides new compositions for modulating immune response in individuals. The new compositions are immunomodulatory oligonucleotide/microcarrier (IMO/MC) complexes or encapsulates which comprise an immunomodulatory oligonucleotide complexed to or encapsulated within a microcarrier. IMO/MC complexes may be covalent complexes, in which the IMO portion of the complex is covalently bonded to the MC, either directly or via a linker (i.e., indirectly), or they may be direct or indirect non-covalent complexes.

Immunomodulatory Oligonucleotides

In accordance with the present invention, the immunomodulatory oligonucleotide is a 3-6mer having the sequence 5'-$X_1$CG$X_2$-3', where $X_1$ is zero to four nucleotides, $X_2$ is zero to four nucleotides, excluding the sequences 5'-GACGTT-3', 5'-TCCGGA-3', and 5'-GAGCTT-3'. Preferably, the IMO is a 3-6mer, more preferably a 5mer or 6mer, comprising the sequence 5'-$X_1$TCG$X_2$-3' or 5'-$X_1$UCG$X_2$-3', where $X_1$ is zero to two nucleotides and $X_2$ is zero to three nucleotides. Other preferred IMOs have the sequence 5'-$X_1$TCG$X_2$-3' 5'-$X_1$UCG$X_2$-3', where $X_1$ is zero or one nucleotide and $X_2$ is two to three nucleotides and the IMO is no longer than six nucleotides. Accordingly, the invention provides for IMOs of three to six nucleotides in length comprising 5'-TCG-3' and/or 5'-CG-3'.

The IMO may be palindromic (i.e., be self-complementary), although a palindromic sequence is not required. The IMO affects a measurable immune response, as measured in vitro, in vivo and/or ex vivo, when complexed with or encapsulated in a microcarrier. In some embodiments, the IMO is not active, as measured in vitro, in vivo and/or ex vivo, when uncomplexed or unencapsulated.

In some embodiments, the IMO is a trimer (3mer) having the sequence 5'-TCG-3' or 5'-UCG-3'.

In some embodiments, the IMO is a quatramer (4mer) having a sequence according to the formula 5'-$X_1$TCG-3', 5'-TCG$X_2$-3', 5'-$X_1$UCG-3', or 5'-UCG$X_2$-3', where $X_1$ is A, C, G, T, U, or I and $X_2$ is A, C, G, T, U, or I.

In some embodiments, the IMO is a pentamer (5mer) having a sequence according to the formula 5'-$X_1$TCG$X_2$-3' or 5'-$X_1$UCG$X_2$-3' where $X_1$ is A, C, G, T, U, or I and $X_2$ is A, C, G, T, U, or I, or according to the formula 5'-TCG$X_3$-3' or 5'-UCG$X_3$-3' where $X_3$ is AA, AC, AG, AT, AU, AI, CA, CC, CG, CT, CU, CI, GA, GC, GG, GT, GU, GI, TA, TC, TG, TT, TU, TI, UA, UC, UG, UT, UU, UI, IA, IC, IG, IT, IU, or II.

In some embodiments, the IMO is a hexamer having a sequence according to the formula 5'-$X_1$TCG$X_2$-3' or 5'-$X_1$UCG$X_2$-3' where $X_1$ is A, C, G, T, U, or I and $X_2$ is AA, AC, AG, AT, AU, AI, CA, CC, CG, CT, CU, CI, GA, GC, GG, GT, GU, GI, TA, TC, TG, TT, TU, TI, UA, UC, UG, UT, UU, UI, IA, IC, IG, IT, IU, or II, or according to the formula 5'-TCG$X_3$-3' or 5'-UCG$X_2$-3' where $X_3$ is AAA, AAC, AAG, AAT, AAU, AAI, ACA, ACC, ACG, ACT, ACU, ACI, AGA, AGC, AGG, AGT, AGU, AGI, ATA, ATC, ATG, ATT, ATU, ATI, AUA, AUC, AUG, AUT, AUU, AUI, AIA, AIC, AIG, AIT, AIU, AII, CAA, CAC, CAG, CAT, CAU, CAI, CCA, CCC, CCG, CCT, CCU, CCI, CGA, CGC, CGG, CGT, CGU, CGI, CTA, CTC, CTG, CTT, CTU, CTI, CUA, CUC, CUG, CUT, CUU, CUI, GAA, GAC, GAG, GAT, GAU, GAI, GCA, GCC, GCG, GCT, GCU, GCI, GGA, GGC, GGG, GGT, GGU, GGI, GTA, GTC, GTG, GTT, GTU, GTI, GIA, GIC, GIG, GIT, GIU, GII, TAA, TAC, TAG, TAT, TAU, TAI, TCA, TCC, TCG, TCT, TCU, TCI, TGA, TGC, TGG, TGT, TGU, TGI, TTA, TTC, TTG, TTT, TTU, TTI, TUA, TUC, TUG, TUT, TUU, TUI, TIA, TIC, TIG, TIT, TIU, TII, UAA, UAC, UAG, UAT, UAU, UAI, UCA, UCC, UCG, UCT, UCU, UCI, UGA, UGC, UGG, UGT, UGU, UGI, UTA, UTC, UTG, UTT, UTU, UTI, UUA, UUC, UUG, UUT, UUU, UUI, UTA, UIC, UIG, UIT, UIU, UII, IAA, IAC, IAG, IAT, IAU, IAI, ICA, ICC, ICG, ICT, ICU, ICI, IGA, IGC, IGG, IGT, IGU, IGI, ITA, ITC, ITG, ITT, ITU, ITI, IIA, ITC, IIG, ITT, IIU, or III.

Additional embodiments include the hexamers 5'-TTTCGT-3' and 5'-AACGTT-3'.

It is preferred that cytosines present in the IMO are not methylated, although other modifications/additions are contemplated. However, in certain embodiments the IMO may contain one or more methylated cytosines. In such embodiments it is preferred that the cytosine of the core trimer sequence (i.e., $C_1$ of oligonucleotide sequences according to the formula 5'-$X_1$T$C_1$G$X_2$-3' or 5'-$X_1$U$C_1$G$X_2$-3' where $X_1$ is zero or one nucleotide and $X_2$ is zero to three nucleotides and the oligonucleotide is a three to six bases in length) of the IMO is not methylated at position C5. However, methylation at position N4 is contemplated in those IMOs comprising methylated cytosines.

An IMO may contain modifications. Modifications of IMOs include any known in the art, but are not limited to, modifications of the 3'OH or 5'OH group, modifications of the nucleotide base, modifications of the sugar component, and modifications of the phosphate group. Various such modifications are described below.

In certain embodiments, the cytosine of the core trimer is modified, preferably by addition of an electron-withdrawing group such as a halogen, preferably bromine, a nitrogen, or a hydroxyl at the C-5 and/or C-6 position of the cytosine (e.g., or by substitution with a modified cytosine such as azacytosine or cytosine arabinoside. Additionally, IMOs containing a uracil in the core trimer (i.e., IMOs having sequences of the formula 5'-$X_1U_1$CG$X_2$-3', where $U_1$ is the uracil in the core trimer, $X_1$ is zero to one nucleotides and $X_2$ is zero to three nucleotides and the IMO is three to six bases in length) may also or alternately comprise a modified uracil in the core trimer or at any other uracil in the IMO.

An IMO may be single stranded or double stranded DNA, as well as single or double-stranded RNA or other modified polynucleotides. An IMO may or may not include a palindromic region. An IMO may contain naturally-occurring or modified, non-naturally occurring bases, and may contain modified sugar, phosphate, and/or termini. Examples of base modifications include, but are not limited to, addition of an electron-withdrawing moiety to C-5 and/or C-6 of a cytosine in the IMO (e.g., 5-bromocytosine, 5-chlorocytosine, 5-fluorocytosine, 5-iodocytosine). See, for example, International Patent Application No. WO 99/62923.

The IMO can be synthesized using techniques and nucleic acid synthesis equipment which are well known in the art including, but not limited to, enzymatic methods, chemical methods, and the degradation of larger oligonucleotide sequences. See, for example, Ausubel et al. (1987); and Sambrook et al. (1989). When assembled enzymatically, the individual units can be ligated, for example, with a ligase such as T4 DNA or RNA ligase. U.S. Pat. No. 5,124,246. Oligonucleotide degradation can be accomplished through the exposure of an polynucleotide to a nuclease, as exemplified in U.S. Pat. No. 4,650,675.

The techniques for making oligonucleotides and modified oligonucleotides are known in the art. Naturally occurring DNA or RNA, containing phosphodiester linkages, is generally synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Once the desired oligonucleotide sequence has been synthesized, the oligonucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in Protocols for Oligonucleotides and Analogs, Synthesis and Properties (Agrawal, ed.) Humana Press, Totowa, N.J.; Warner et al. (1984) *DNA* 3:401 and U.S. Pat. No. 4,458,066.

The IMO may contain phosphate-modified oligonucleotides including, but not limited to, methyl phosphonate, phosphorothioate, phosphoramidate (bridging or non-bridging), phosphotriester, and phosphorodithioate. The modified phosphates may be at any, or even all, positions of the IMO and/or may be used in any combination. Synthesis of polynucleotides containing modified phosphate linkages or non-phosphate linkages is also know in the art. For a review, see Matteucci (1997) "Oligonucleotide Analogs: an Overview" in Oligonucleotides as Therapeutic Agents, (D. J. Chadwick and G. Cardew, ed.) John Wiley and Sons, New York, N.Y. The phosphorous derivative (or modified phosphate group) which can be attached to the sugar or sugar analog moiety in the oligonucleotides of the present invention can be a monophosphate, diphosphate, triphosphate, alkylphosphonate, phosphorothioate, phosphorodithioate or the like. The preparation of the above-noted phosphate analogs, and their incorporation into nucleotides, modified nucleotides and oligonucleotides, per se, is also known and need not be described here in detail. Peyrottes et al. (1996) *Nucleic Acids Res.* 24:1841-1848; Chaturvedi et al. (1996) *Nucleic Acids Res.* 24:2318-2323; and Schultz et al. (1996) *Nucleic Acids Res.* 24:2966-2973. For example, synthesis of phosphorothioate oligonucleotides is similar to that described above for naturally occurring oligonucleotides except that the oxidation step is replaced by a sulfurization step (Zon (1993) "Oligonucleoside Phosphorothioates" in Protocols for Oligonucleotides and Analogs, Synthesis and Properties (Agrawal, ed.) Humana Press, pp. 165-190). Similarly the synthesis of other phosphate analogs, such as phosphotriester (Miller et al. (1971) *JACS* 93:6657-6665), non-bridging phosphoramidates (Jager et al. (1988) *Biochem.* 27:7247-7246), N3' to P5' phosphoramidates (Nelson et al. (1997) *JOC* 62:7278-7287) and phosphorodithioates (U.S. Pat. No. 5,453,496) has also been described. Other non-phosphorous based modified oligonucleotides can also be used (Stirchak et al. (1989) *Nucleic Acids Res.* 17:6129-6141). Oligonucleotides with phosphorothioate backbones appear to be more resistant to degradation after injection into the host. Braun et al. (1988) *J. Immunol.* 141:2084-2089; and Latimer et al. (1995) *Mol. Immunol.* 32:1057-1064. Preferred IMOs comprise complete phosphorothioate, complete phosphodiester, or mixed phosphorothioate/phosphodiester backbones.

IMOs used in the invention can comprise ribonucleotides (containing ribose as the only or principal sugar component), deoxyribonucleotides (containing deoxyribose as the principal sugar component), or, as is known in the art, modified sugars or sugar analogs can be incorporated in the IMO. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. In the IMO, the sugar moiety is preferably the furanoside of ribose, deoxyribose, arabinose or 2'-0-alkylribose, and the sugar can be attached to the respective heterocyclic bases either in α or β anomeric configuration. Sugar modifications include, but are not limited to, 2'-alkoxy-RNA analogs, 2'-amino-RNA analogs and 2'-alkoxy- or amino-RNA/DNA chimeras. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. Sugar modifications may also be made and combined with any phosphate modification in the preparation of an IMO.

The heterocyclic bases, or nucleic acid bases, which are incorporated in the IMO can be the naturally-occurring principal purine and pyrimidine bases, (namely uracil, thymine, cytosine, inosine, adenine and guanine, as mentioned above), as well as naturally-occurring and synthetic modifications of said principal bases, such as inosine.

Those skilled in the art will recognize that a large number of "synthetic" non-natural nucleosides comprising various heterocyclic bases and various sugar moieties (and sugar analogs) are available in the art, and that as long as other criteria of the present invention are satisfied, the IMO can include one or several heterocyclic bases other than the principal five base components of naturally-occurring nucleic acids. Preferably, however, the heterocyclic base in the IMO includes, but is not limited to, uracil-5-yl, cytosin-5-yl, adenin-7-yl, adenin-8-yl, guanin-7-yl, guanin-8-yl, 4-aminopyrrolo[2,3-d]pyrimidin-5-yl, 2-amino-4-oxopyrolo[2,3-d]pyrimidin-5-yl, 2-amino-4-oxopyrrolo[2,3-d]pyrimidin-3-yl groups, where the purines are attached to the sugar moiety of the IMO via the 9-position, the pyrimidines via the 1-position, the pyrrolopyrimidines via the 7-position and the pyrazolopyrimidines via the 1-position.

The IMO may comprise at least one modified base as described, for example, in the commonly owned international application WO 99/62923. As used herein, the term "modified base" is synonymous with "base analog", for example, "modified cytosine" is synonymous with "cytosine analog."

Similarly, "modified" nucleosides or nucleotides are herein defined as being synonymous with nucleoside or nucleotide "analogs." Examples of base modifications include, but are not limited to, addition of an electron-withdrawing moiety to C-5 and/or C-6 of a cytosine of the IMO. Preferably, the electron-withdrawing moiety is a halogen. Modified cytosines can include, but are not limited to, azacytosine, 5-bromocytosine, 5-chlorocytosine, chlorinated cytosine, cyclocytosine, cytosine arabinoside, 5-fluorocytosine, fluoropyrimidine, 5,6-dihydrocytosine, 5-iodocytosine, 5-nitrocytosine, 5-hydroxycytosine and any other pyrimidine analog or modified pyrimidine, although some embodiments may exclude 5-bromocytosine. Preferred modified uracils are modified at C-5 and/or C-6, preferably with a halogen, and include, but are not limited to, 5-bromouracil, 5-chlorouracil, 5-fluorouracil, 5-iodouracil, and hydroxyuracil. Also see, Kandimalla et al., 2001, *Bioorg. Med. Chem.* 9:807-13. See, for example, International Patent Application No. WO 99/62923. Other examples of base modifications include the addition of one or more thiol groups to the base including, but not limited to, 6-thio-guanine, 4-thio-thymine and 4-thiouracil. Additionally, some IMOs may comprise modified bases such as 7-deazaguanosine in place of any guanosine residue, or a modified cytosine selected from N4-ethylcytosine or N4-methylcytosine or 5-hydroxycytosine in place of any cytosine residue, including the cytosine of the core trimer.

The preparation of base-modified nucleosides, and the synthesis of modified oligonucleotides using said base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also been described (including, but not limited to, e.g., U.S. Pat. Nos. 4,849,513, 5,015,733, 5,118,800, 5,118,802) and can be used similarly.

Methods for detecting immunomodulatory activity of an immunostimulatory sequence have been described in the art and may be readily identified using standard assays which indicate various aspects of the immune response, such as cytokine secretion, antibody production, NK cell activation and T cell proliferation. See, e.g., WO 97/28259; WO 98/16247; WO 99/11275; Krieg et al. (1995) *Nature* 374:546-549; Yamamoto et al. (1992a); Ballas et al. (1996); Klinman et al. (1997); Sato et al. (1996); Pisetsky (1996a); Shimada et al. (1986) *Jpn. J. Cancer Res.* 77:808-816; Cowdery et al. (1996) *J. Immunol.* 156:4570-4575; Roman et al. (1997); and Lipford et al. (1997a). Such methods are likewise applicable for assessing the immunostimulatory activity of an IMO and/or IMO/MC complex or encapsulate.

One property of an IMO is the "isolated immunomodulatory activity" associated with the nucleotide sequence of the IMO. As noted above, the present inventors have discovered that, surprisingly, IMO/MC complexes exhibit immunomodulatory activity even when the IMO has a sequence that, if presented as a polynucleotide alone, does not exhibit comparable immunomodulatory activity.

In some embodiments, an IMO of an IMO/MC complex or encapsulate does not have "isolated immunomodulatory activity," or has "inferior isolated immunomodulatory activity," (i.e., when compared to the IMO/MC complex or encapsulate), as described below.

The "isolated immunomodulatory activity" of an IMO is determined by measuring the immunomodulatory activity of an isolated polynucleotide having the primary sequence of the IMO, and having the same nucleic acid backbone (e.g., phosphorothioate, phosphodiester, chimeric). To determine the independent immunomodulatory activity of, for example, an IMO in the IMO/MC complex, a test polynucleotide having the same sequence (e.g., 5'-TCGTCG-3') and same backbone structure (e.g., phosphorothioate) is synthesized using routine methods, and its immunomodulatory activity (if any) is measured. Immunomodulatory activity can be determined using standard assays which indicate various aspects of the immune response, such as those described herein. For example, the human PBMC assay described herein is used. To account for donor variation, typically the assay is carried out in multiple donors. A polynucleotide does not have immunomodulatory activity (and the corresponding IMO does not have "isolated immunomodulatory activity") when the amount of IFN-γ secreted by PBMCs contacted with the polynucleotide is not significantly greater (e.g., less than about 2-fold greater) in the majority of donors than in the absence of the test compound or, (in some embodiments) in the presence of an inactive control compound (e.g., 5'-TGACTGTGAACCTTAGAGATGA-3' (SEQ ID NO:1)).

To compare the immunomodulatory activity of an IMO/MC complex or encapsulate and an isolated polynucleotide, immunomodulatory activity is measured, preferably, but not necessarily, using the human PBMC assay. Usually, the activity of two compounds is compared by assaying them in parallel under the same conditions (e.g., using the same cells), usually at a concentration of about 20 μg/ml. Generally, concentration is determined by measuring absorbance at 260 nm and using the conversion 0.5 $OD_{260}$/ml=20 μg/ml. This normalizes the amount of total nucleic acid in the test sample. Alternatively, concentration or weight can be measured by other methods known in the art.

An IMO of an IMO/MC complex or encapsulate is characterized as having "inferior immunomodulatory activity," when the test polynucleotide has less activity than the IMO/MC complex or encapsulate to which it is compared. Preferably the isolated immunomodulatory activity of the test polynucleotide is no more than about 50% of the activity of the IMO/MC complex or encapsulate, more preferably no more than about 20%, most preferably no more than about 10% of the activity of the IMO/MC complex or encapsulate, or in some embodiments, even less.

Microcarriers

Microcarriers useful in the invention are less than about 150, 120, or 100 μm in size, typically less than about 50-60 μm in size, preferably less than about 20 or 10 μm in size, and are insoluble in pure water. Microcarriers used in the invention are preferably biodegradable, although nonbiodegradable microcarriers are acceptable. Microcarriers are commonly solid phase, such as "beads" or other particles, although liquid phase microcarriers such as oil in water emulsions comprising a biodegradable polymers or oils are also contemplated. A wide variety of biodegradable and nonbiodgradable materials acceptable for use as microcarriers are known in the art.

Microcarriers for use in the compositions or methods of the invention are generally less than about 20 to 10 μm in size (e.g., have an average diameter of less than about 10 μm, or at least about 97% of the particles pass through a 10 μm screen filter), and include nanocarriers (i.e., carriers of less than about 1 μm size). Preferably, microcarriers are selected having sizes within an upper limit of about 9, 7, 5, 2, or 1 μm or 900, 800, 700, 600, 500, 400, 300, 250, 200, or 100 nm and an independently selected lower limit of about 4, 2, or 1 μm or about 800, 600, 500, 400, 300, 250, 200, 150, 100, 50, 25, or 10 nm, where the lower limit is less than the upper limit. In some embodiments, the microcarriers have a size of about 1.0-1.5 µm, about 1.0-2.0 µm or about 0.9-1.6 µm. In certain preferred embodiments, the microcarriers have a size of about 10 nm to about 5 µm, about 10 nm to about 10 µm, 10 nm to about 20 or about 25 nm to about 4.5 about 1 about 1.2 about 1.4 about 1.5 about 1.6 about 1.8 about 2.0 about 2.5 µm or about 4.5 µm. When the microcarriers are nanocarriers, preferred embodiments include nanocarriers of about 25 to about 300 nm, 50 to about 200 nm, about 50 nm, 100 nm, or about 200 nm.

Solid phase biodegradable microcarriers may be manufactured from biodegradable polymers including, but not limited to: biodegradable polyesters, such as poly(lactic acid), poly(glycolic acid), and copolymers (including block copolymers) thereof, as well as block copolymers of poly(lactic acid), polymethylidene malonate, and poly(ethylene glycol); polyorthoesters such as polymers based on 3,9-diethylidene-2,4,8,10-tetraoxaspiro[5.5]undecane (DETOSU); polyanhydrides such as poly(anhydride) polymers based on relatively hydrophilic monomers such as sebacic acid; polyanhydride imides, such as polyanhydride polymers based on sebacic acid-derived monomers incorporating amino acids (i.e., linked to sebacic acid by imide bonds through the amino-terminal nitrogen) such as glycine or alanine; polyanhydride esters; polyphosphazenes, especially poly(phosphazenes) which contain hydrolysis-sensitive ester groups which can catalyze degradation of the polymer backbone through generation of carboxylic acid groups (Schacht et al., (1996) *Biotechnol. Bioeng.* 1996:102); and polyamides such as poly(lactic acid-co-lysine).

A wide variety of nonbiodegradable materials suitable for manufacturing microcarriers are also known, including, but not limited to polystyrene, polypropylene, polyethylene, polyacrylamide, latex, dextran, and inorganic materials including inorganic crystalline materials such as silica, hydroxyapatite, alum, and calcium phosphate, as well as ceramics, gold, and ferromagnetic or paramagnetic materials. Certain embodiments exclude gold, latex, and/or magnetic beads. In certain embodiments, the microcarriers may be made of a first material (e.g., a magnetic material) encapsulated with a second material (e.g., polystyrene).

Solid phase microspheres are prepared using techniques known in the art. For example, they can be prepared by emulsion-solvent extraction/evaporation technique. Generally, in this technique, biodegradable polymers such as polyanhydrates and poly(α-hydroxy esters), for example, poly(lactic acid), poly(glycolic acid), poly(D,L-lactic-co-glycolic acid) and poly(caprolactone), are dissolved in a suitable organic solvent, such as methylene chloride, to constitute the dispersed phase (DP) of the emulsion. The DP is emulsified by high-speed homogenization into an excess volume of aqueous continuous phase (CP) that contains a dissolved surfactant, for example, polyvinylalcohol (PVA) or polyvinylpyrrolidone (PVP). Surfactant in the CP is to ensure the formation of discrete and suitably-sized emulsion droplet. The organic solvent is then extracted into the CP and subsequently evaporated by raising the system temperature. The solid microparticles are then separated by centrifugation or filtration, and dried, for example, by lyophilization or application of vacuum, before storing at 4° C. Production of sub-micrometer-sized microcarriers (e.g., nanocarriers) from, for example, poly(alkyl-α-cyanoacrylates), is preferably carried out by the micellar polymerization of an alkyl-cyano-acrylate as described in U.S. Pat. No. 4,489,055.

Physico-chemical characteristics such as mean size, size distribution and surface charge of dried microspheres may be determined. Size characteristics are determined, for example, by a dynamic light scattering technique (preferably used for microcarriers of less than about 1-2 µm in nominal size) or an obscuration technique (preferably used for microcarriers of greater than about 1 µm in nominal size). Surface charge is preferably determined by measuring the zeta potential.

Liquid phase microcarriers include liposomes, micelles, oil droplets and other lipid or oil-based particles which incorporate biodegradable polymers or oils. In certain embodiments, the biodegradable polymer is a surfactant. In other embodiments, the liquid phase microcarriers are biodegradable due to the inclusion of a biodegradable oil such as squalene or a vegetable oil. One preferred liquid phase microcarrier is oil droplets within an oil-in-water emulsion. Preferably, oil-in-water emulsions used as microcarriers comprise biodegradable substituents such as squalene.

Antigen

IMO/MC complexes and encapsulates may be prepared which comprise antigen or which are antigen-free, i.e., IMO/MC complexes or encapsulates not linked to an antigen. Any antigen may be used in the preparation of IMO/MC complexes or encapsulates comprising antigen.

In some embodiments, the antigen is an allergen. Examples of recombinant allergens are provided in Table 1. Preparation of many allergens is well-known in the art, including, but not limited to, preparation of ragweed pollen allergen Antigen E (Amb aI) (Rafnar et al. (1991) *J. Biol. Chem.* 266:1229-1236), major dust mite allergens Der pI and Der PII (Chua et al. (1988) *J. Exp. Med.* 167:175-182; Chua et al. (1990) *Int. Arch. Allergy Appl. Immunol.* 91:124-129), white birch pollen Bet vl (Breiteneder et al. (1989) *EMBO J.* 8:1935-1938), domestic cat allergen Fel d I (Rogers et al. (1993) *Mol. Immunol.* 30:559-568), and protein antigens from tree pollen (Elsayed et al. (1991) *Scand. J. Clin. Lab. Invest. Suppl.* 204:17-31). As indicated, allergens from trees are known, including allergens from birch, juniper and Japanese cedar. Preparation of protein antigens from grass pollen for in vivo administration has been reported. Malley (1989) *J. Reprod. Immunol.* 16:173-186. As Table 1 indicates, in some embodiments, the allergen is a food allergen such as peanut allergen, for example Ara h I, and in some embodiments, the allergen is a grass allergen such as a rye allergen, for example Lol p 1. Table 1 shows a list of allergens that may be used.

TABLE 1

| RECOMBINANT ALLERGENS | | |
|---|---|---|
| Group | Allergen | Reference |
| ANIMALS: CRUSTACEA | | |
| Shrimp/lobster | tropomyosin | Leung et al. (1996) J. Allergy Clin. Immunol. 98: 954-961 |
| | Pan s I | Leung et al. (1998) Mol. Mar. Biol. Biotechnol. 7: 12-20 |

TABLE 1-continued

| | RECOMBINANT ALLERGENS | |
|---|---|---|
| Group | Allergen | Reference |
| INSECTS | | |
| Ant | Sol i 2 (venom) | Schmidt et al. J Allergy Clin Immunol., 1996, 98: 82-8 |
| Bee | Phospholipase A2 (PLA) | Muller et al. J Allergy Clin Immunol, 1995, 96: 395-402 |
| | | Forster et al. J Allergy Clin Immunol, 1995, 95: 1229-35 |
| | | Muller et al. Clin Exp Allergy, 1997, 27: 915-20 |
| | Hyaluronidase (Hya) | Soldatova et al. J Allergy Clin Immunol, 1998, 101: 691-8 |
| Cockroach | Bla g Bd9OK | Helm et al. J Allergy Clin Immunol, 1996, 98: 172-180 |
| | Bla g 4 (a calycin) | Vailes et al. J Allergy Clin Immunol, 1998, 101: 274-280 |
| | Glutathione S-transferase | Arruda et al. J Biol Chem, 1997, 272: 20907-12 |
| | Per a 3 | Wu et al. Mol Immunol, 1997, 34: 1-8 |
| Dust mite | Der p 2 (major allergen) | Lynch et al. J Allergy Clin Immunol, 1998, 101: 562-4 |
| | | Hakkaart et al. Clin Exp Allergy, 1998, 28: 169-74 |
| | | Hakkaart et al. Clin Exp Allergy, 1998, 28: 45-52 |
| | | Hakkaart et al. Int Arch Allergy Immunol, 1998, 115 (2): 150-6 |
| | | Mueller et al. J Biol Chem, 1997, 272: 26893-8 |
| | Der p2 variant | Smith et al. J Allergy Clin Immunol, 1998, 101: 423-5 |
| | Der f2 | Yasue et al. Clin Exp Immunol, 1998, 113: 1-9 |
| | | Yasue et al. Cell Immunol, 1997, 181: 30-7 |
| | Der p10 | Asturias et al. Biochim Biophys Acta, 1998, 1397: 27-30 |
| | Tyr p 2 | Eriksson et al. Eur J Biochem, 1998 |
| Hornet | Antigen 5 aka Dol m V (venom) | Tomalski et al. Arch Insect Biochem Physiol, 1993, 22: 303-13 |
| Mosquito | Aed a I (salivary apyrase) | Xu et al. Int Arch Allergy Immunol, 1998, 115: 245-51 |
| Yellow jacket | antigen 5, hyaluronidase and phospholipase (venom) | King et al. J Allergy Clin Immunol, 1996, 98: 588-600 |
| MAMMALS | | |
| Cat | Fel d I | Slunt et al. J Allergy Clin Immunol, 1995, 95: 1221-8 |
| | | Hoffmann et al. (1997) J Allergy Clin Immunol 99: 227-32 |
| | | Hedlin Curr Opin Pediatr, 1995, 7: 676-82 |
| Cow | Bos d 2 (dander; a lipocalin) | Zeiler et al. J Allergy Clin Immunol, 1997, 100: 721-7 |
| | | Rautiainen et al. Biochem Bioph. Res Comm., 1998, 247: 746-50 |
| | β-lactoglobulin (BLG, major cow milk allergen) | Chatel et al. Mol Immunol, 1996, 33: 1113-8 |
| | | Lehrer et al. Crit Rev Food Sci Nutr, 1996, 36: 553-64 |
| Dog | Can f I and Can f 2, salivary lipocalins | Konieczny et al. Immunology, 1997, 92: 577-86 |
| | | Spitzauer et al. J Allergy Clin Immunol, 1994, 93: 614-27 |
| | | Vrtala et al. J Immunol, 1998, 160: 6137-44 |
| Horse | Equ c1 (major allergen, a lipocalin) | Gregoire et al. J Biol Chem, 1996, 271: 32951-9 |
| Mouse | mouse urinary protein (MUP) | Konieczny et al. Immunology, 1997, 92: 577-86 |
| OTHER MAMMALIAN ALLERGENS | | |
| Insulin | | Ganz et al. J Allergy Clin Immunol, 1990, 86: 45-51 |
| | | Grammer et al. J Lab Clin Med, 1987, 109: 141-6 |
| | | Gonzalo et al. Allergy, 1998, 53: 106-7 |
| Interferons | interferon alpha 2c | Detmar et al. Contact Dermatis, 1989, 20: 149-50 |
| MOLLUSCS | topomyosin | Leung et al. J Allergy Clin Immunol, 1996, 98: 954-61 |
| PLANT ALLERGENS: | | |
| Barley | Hor v 9 | Astwood et al. Adv Exp Med Biol, 1996, 409: 269-77 |
| Birch | pollen allergen, Bet v 4 | Twardosz et al. Biochem Bioph. Res Comm., 1997, 23 9: 197 |
| | rBet v 1 Bet v 2: (profilin) | Pauli et al. J Allergy Clin Immunol, 1996, 97: 1100-9 |
| | | van Neerven et al. Clin Exp Allergy, 1998, 28: 423-33 |
| | | Jahn-Schmid et al. Immunotechnology, 1996, 2: 103-13 |
| | | Breitwieser et al. Biotechniques, 1996, 21: 918-25 |
| | | Fuchs et al. J Allergy Clin Immunol, 1997, 100: 356-64 |
| Brazil nut | globulin | Bartolome et al. Allergol Immunopathol, 1997, 25: 135-44 |
| Cherry | Pru a I (major allergen) | Scheurer et al. Mol Immunol, 1997, 34: 619-29 |
| Corn | Zml3 (pollen) | Heiss et al. FEBS Lett, 1996, 381: 217-21 |
| | | Lehrer et al. Int Arch Allergy Immunol, 1997, 113: 122-4 |
| Grass | Phl p 1, Phl p 2, Phl p 5 (timothy grass pollen) | Bufe et al. Am J Respir Crit Care Med, 1998, 157: 1269-76 |
| | | Vrtala et al. J Immunol Jun. 15, 1998, 160: 6137-44 |
| | | Niederberger et al. J Allergy Clin Immun., 1998, 101: 258-64 |
| | Hol 1 5 velvet grass pollen | Schramm et al. Eur J Biochem, 1998, 252: 200-6 |

TABLE 1-continued

RECOMBINANT ALLERGENS

| Group | Allergen | Reference |
|---|---|---|
| | Bluegrass allergen | Zhang et al. J Immunol, 1993, 151: 791-9 |
| | Cyn d 7 Bermuda grass | Smith et al. Int Arch Allergy Immunol, 1997, 114: 265-71 |
| | Cyn d 12 (a profilin) | Asturias et al. Clin Exp Allergy, 1997, 27: 1307-13 |
| | | Fuchs et al. J Allergy Clin Immunol, 1997, 100: 356-64 |
| Japanese Cedar | Jun a 2 (*Juniperus ashei*) | Yokoyama et al. Biochem. Biophys. Res. Commun., 2000, 275: 195-202 |
| | Cry j 1, Cry j 2 (*Cryptomeria japonica*) | Kingetsu et al. Immunology, 2000, 99: 625-629 |
| Juniper | Jun o 2 (pollen) | Tinghino et al. J Allergy Clin Immunol, 1998, 101: 772-7 |
| Latex | Hev b 7 | Sowka et al. Eur J Biochem, 1998, 255: 213-9 |
| | | Fuchs et al. J Allergy Clin Immunol, 1997, 100: 356-64 |
| *Mercurialis* | Mer a I (profilin) | Vallverdu et al. J Allergy Clin Immunol, 1998, 101: 363-70 |
| Mustard (Yellow) | Sin a I (seed) | Gonzalez de la Pena et al. Biochem Bioph. Res Comm., 1993, 190: 648-53 |
| Oilseed rape | Bra r I pollen allergen | Smith et al. Int Arch Allergy Immunol, 1997, 114: 265-71 |
| Peanut | Ara h I | Stanley et al. Adv Exp Med Biol, 1996, 409: 213-6 |
| | | Burks et al. J Clin Invest, 1995, 96: 1715-21 |
| | | Burks et al. Int Arch Allergy Immunol, 1995, 107: 248-50 |
| Poa pratensis | Poa p9 | Parronchi et al. Eur J Immunol, 1996, 26: 697-703 |
| | | Astwood et al. Adv Exp Med Biol, 1996, 409: 269-77 |
| Ragweed | Amb a I | Sun et al. Biotechnology Aug, 1995, 13: 779-86 |
| | | Hirschwehr et al. J Allergy Clin Immunol, 1998, 101: 196-206 |
| | | Casale et al. J Allergy Clin Immunol, 1997, 100: 110-21 |
| Rye | Lol p I | Tamborini et al. Eur J Biochem, 1997, 249: 886-94 |
| Walnut | Jug r I | Teuber et al. J Allergy Clin Immun., 1998, 101: 807-14 |
| Wheat | allergen | Fuchs et al. J Allergy Clin Immunol, 1997, 100: 356-64 |
| | | Donovan et al. Electrophoresis, 1993, 14: 917-22 |
| FUNGI: | | |
| *Aspergillus* | Asp f 1, Asp f 2, Asp f3, Asp f 4, rAsp f 6 | Crameri et al. Mycoses, 1998, 41 Suppl 1: 56-60 |
| | | Hemmann et al. Eur J Immunol, 1998, 28: 1155-60 |
| | | Banerjee et al. J Allergy Clin Immunol, 1997, 99: 821-7 |
| | | Crameri Int Arch Allergy Immunol, 1998, 115: 99-114 |
| | | Crameri et al. Adv Exp Med Biol, 1996, 409: 111-6 |
| | | Moser et al. J Allergy Clin Immunol, 1994, 93: 1-11 |
| | Manganese superoxide dismutase (MNSOD) | Mayer et al. Int Arch Allergy Immunol, 1997, 113: 213-5 |
| *Blomia* | allergen | Caraballo et al. Adv Exp Med Biol, 1996, 409: 81-3 |
| *Penicillinium* | allergen | Shen et al. Clin Exp Allergy, 1997, 27: 682-90 |
| *Psilocybe* | Psi c 2 | Horner et al. Int Arch Allergy Immunol, 1995, 107: 298-300 |

In some embodiments, the antigen is from an infectious agent, including protozoan, bacterial, fungal (including unicellular and multicellular), and viral infectious agents. Examples of suitable viral antigens are described herein and are known in the art. Bacteria include *Hemophilus influenza*, *Mycobacterium tuberculosis* and *Bordetella pertussis*. Protozoan infectious agents include malarial plasmodia, *Leishmania* species, *Trypanosoma* species and *Schistosoma* species. Fungi include *Candida albicans*.

In some embodiments, the antigen is a viral antigen. Viral polypeptide antigens include, but are not limited to, HIV proteins such as HIV gag proteins (including, but not limited to, membrane anchoring (MA) protein, core capsid (CA) protein and nucleocapsid (NC) protein), HIV polymerase, influenza virus matrix (M) protein and influenza virus nucleocapsid (NP) protein, hepatitis B surface antigen (HBsAg), hepatitis B core protein (HBcAg), hepatitis e protein (HBeAg), hepatitis B DNA polymerase, hepatitis C antigens, and the like. References discussing influenza vaccination include Scherle and Gerhard (1988) *Proc. Natl. Acad. Sci. USA* 85:4446-4450; Scherle and Gerhard (1986) *J. Exp. Med.* 164:1114-1128; Granoff et al. (1993) *Vaccine* 11:S46-51; Kodihalli et al. (1997) *J. Virol.* 71:3391-3396; Ahmeida et al. (1993) *Vaccine* 11:1302-1309; Chen et al. (1999) *Vaccine* 17:653-659; Govorkova and Smirnov (1997) *Acta Virol.* (1997) 41:251-257; Koide et al. (1995) *Vaccine* 13:3-5; Mbawuike et al. (1994) *Vaccine* 12:1340-1348; Tamura et al. (1994) *Vaccine* 12:310-316; Tamura et al. (1992) *Eur. J. Immunol.* 22:477-481; Hirabayashi et al. (1990) *Vaccine* 8:595-599. Other examples of antigen polypeptides are group- or sub-group specific antigens, which are known for a number of infectious agents, including, but not limited to, adenovirus, herpes simplex virus, papilloma virus, respiratory syncytial virus and poxviruses.

Many antigenic peptides and proteins are known, and available in the art; others can be identified using conventional techniques. For immunization against tumor formation or treatment of existing tumors, immunomodulatory peptides can include tumor cells (live or irradiated), tumor cell extracts, or protein subunits of tumor antigens such as Her-2/neu, Mart1, carcinoembryonic antigen (CEA), gangliosides, human milk fat globule (HMFG), mucin (MUC1), MAGE antigens, BAGE antigens, GAGE antigens, gp100, prostate specific antigen (PSA), and tyrosinase. Vaccines for immuno-based contraception can be formed by including sperm proteins administered with an IMO/MC complex or encapsulate of the invention. Lea et al. (1996) *Biochim. Biophys. Acta* 1307:263.

Attenuated and inactivated viruses are suitable for use herein as the antigen. Preparation of these viruses is well-known in the art and many are commercially available (see, e.g., Physicians' Desk Reference (1998) 52nd edition, Medical Economics Company, Inc.). For example, polio virus is available as IPOL® (Pasteur Merieux Connaught) and ORIMUNE® (Lederle Laboratories), hepatitis A virus as VAQTA® (Merck), measles virus as ATTENUVAX® (Merck), mumps virus as MUMPSVAX® (Merck) and rubella virus as MERUVAX®II (Merck). Additionally, attenuated and inactivated viruses such as HIV-1, HIV-2, herpes simplex virus, hepatitis B virus, rotavirus, human and non-human papillomavirus and slow brain viruses can provide peptide antigens.

In some embodiments, the antigen comprises a viral vector, such as vaccinia, adenovirus, and canary pox.

Antigens may be isolated from their source using purification techniques known in the art or, more conveniently, may be produced using recombinant methods.

Antigenic peptides can include purified native peptides, synthetic peptides, recombinant proteins, crude protein extracts, attenuated or inactivated viruses, cells, micro-organisms, or fragments of such peptides. Immunomodulatory peptides can be native or synthesized chemically or enzymatically. Any method of chemical synthesis known in the art is suitable. Solution phase peptide synthesis can be used to construct peptides of moderate size or, for the chemical construction of peptides, solid phase synthesis can be employed. Atherton et al. (1981) *Hoppe Seylers Z. Physiol. Chem.* 362: 833-839. Proteolytic enzymes can also be utilized to couple amino acids to produce peptides. Kullmann (1987) Enzymatic Peptide Synthesis, CRC Press, Inc. Alternatively, the peptide can be obtained by using the biochemical machinery of a cell, or by isolation from a biological source. Recombinant DNA techniques can be employed for the production of peptides. Hames et al. (1987) Transcription and Translation: A Practical Approach, IRL Press. Peptides can also be isolated using standard techniques such as affinity chromatography.

Preferably the antigens are peptides, lipids (e.g., sterols excluding cholesterol, fatty acids, and phospholipids), polysaccharides such as those used in *H. influenza* vaccines, gangliosides and glycoproteins. These can be obtained through several methods known in the art, including isolation and synthesis using chemical and enzymatic methods. In certain cases, such as for many sterols, fatty acids and phospholipids, the antigenic portions of the molecules are commercially available.

Examples of viral antigens useful in the subject compositions and methods using the compositions include, but are not limited to, HIV antigens. Such antigens include, but are not limited to, those antigens derived from HIV envelope glycoproteins including, but not limited to, gp160, gp120 and gp41. Numerous sequences for HIV genes and antigens are known. For example, the Los Alamos National Laboratory HIV Sequence Database collects, curates and annotates HIV nucleotide and amino acid sequences. This database is accessible via the internet, at http://hiv-web.lanl.gov/, and in a yearly publication, see Human Retroviruses and AIDS Compendium (for example, 1998 edition).

Antigens derived from infectious agents may be obtained using methods known in the art, for example, from native viral or bacterial extracts, from cells infected with the infectious agent, from purified polypeptides, from recombinantly produced polypeptides and/or as synthetic peptides.

IMO/MC complex or encapsulate formulations may be prepared with other immunotherapeutic agents including, but not limited to, cytokine, adjuvants and antibodies, such as anti-tumor antibodies and derivatives thereof. These IMO/MC complex or encapsulate formulations may be prepared with or without antigen.

IMO/MC Complexes

IMO/MC complexes comprise an IMO bound to the surface of a microcarrier (i.e., the IMO is not encapsulated in the MC), and preferably comprise multiple molecules of IMO bound to each microcarrier. Most commonly, the IMO is linked to (and not embedded in) the surface of the MC, although in certain embodiments the IMO (or a moiety of the IMO) may be embedded in the surface of the MC. In certain embodiments, a mixture of different IMOs may be complexed a microcarrier, such that the microcarrier is bound to more than one IMO species. The bond between the IMO and MC may be covalent or non-covalent. As will be understood by one of skill in the art, the IMO may be modified or derivatized and the composition of the microcarrier may be selected and/or modified to accommodate the desired type of binding desired for IMO/MC complex formation.

The instant invention provides methods of making IMO/MC complexes, as well as the products of such methods. IMO/MC complexes are made by combining an IMO and an MC to form a complex. The specific process for combining the IMO and MC to form a complex will, of course, depend on the type and features of the MC as well as the mode of conjugation of the IMO and MC. When the MC is a solid phase MC, the IMO/MC complex is preferably made by contacting the IMO and the MC under conditions which promote complex formation (which will depend on the type of linkage used in the complex). When the MC is liquid phase, the IMO may be combined with a preformed MC under conditions which promote complex formation or be combined with the components of the MC prior to formation of the MC. In the situation where the IMO is combined with the components of a liquid phase MC, the process of making the MC may incorporate the IMO, thus resulting in the simultaneous creation of IMO/MC complexes, or when it does not, the process will involve an additional step under conditions which promote complex formation.

IMO/MC complexes in accordance with the invention are insoluble in pure water, and IMO/MC complex compositions are preferably free of acetonitrile, dichloroethane, toluene, and methylene chloride (dichlormethane).

Covalently bonded IMO/MC complexes may be linked using any covalent crosslinking technology known in the art. Typically, the IMO portion will be modified, either to incorporate an additional moiety (e.g., a free amine, carboxyl or sulfhydryl group) or incorporate modified (e.g., phosphorothioate) nucleotide bases to provide a site at which the IMP portion may be linked to the microcarrier. The link between the IMO and MC portions of the complex can be made at the 3' or 5' end of the IMO, or at a suitably modified base at an internal position in the IMO. The microcarrier is generally also modified to incorporate moieties through which a covalent link may be formed, although functional groups normally present on the microcarrier may also be utilized. The IMO/MC is formed by incubating the IMO with a microcarrier under conditions which permit the formation of a covalent complex (e.g., in the presence of a crosslinking agent or by use of an activated microcarrier comprising an activated moiety which will form a covalent bond with the IMO).

A wide variety of crosslinking technologies are known in the art, and include crosslinkers reactive with amino, carboxyl and sulfhydryl groups. As will be apparent to one of skill in the art, the selection of a crosslinking agent and crosslinking protocol will depend on the configuration of the IMO and the microcarrier as well as the desired final configuration of the IMO/MC complex. The crosslinker may be either homobifunctional or heterobifunctional. When a homobifunctional crosslinker is used, the crosslinker exploits the same moiety on the IMO and MC (e.g., an aldehyde crosslinker may be used to covalently link an IMO and MC where both the IMO and MC comprise one or more free amines). Heterobifunctional crosslinkers utilize different moieties on the IMO and MC, (e.g., a maleimido-N-hydroxysuccinimide ester may be used to covalently link a free sulfhydryl on the IMO and a free amine on the MC), and are preferred to minimize formation of inter-microcarrier bonds. In most cases, it is preferable to crosslink through a first crosslinking moiety on the microcarrier and a second crosslinking moiety on the IMO, where the second crosslinking moiety is not present on the microcarrier. One preferred method of producing the IMO/MC complex is by 'activating' the microcarrier by incubating with a heterobifunctional crosslinking agent, then forming the IMO/MC complex by incubating the IMO and activated MC under conditions appropriate for reaction. The crosslinker may incorporate a "spacer" arm between the reactive moieties, or the two reactive moieties in the crosslinker may be directly linked.

In one preferred embodiment, the IMO portion comprises at least one free sulfhydryl (e.g., provided by a 5'-thiol modified base or linker) for crosslinking to the microcarrier, while the microcarrier comprises free amine groups. A heterobifunctional crosslinker reactive with these two groups (e.g., a crosslinker comprising a maleimide group and a NHS-ester), such as succinimidyl 4-(N-maleimidomethyl)cyclohexane-1-carboxylate is used to activate the MC, then covalently crosslink the IMO to form the IMO/MC complex.

Non-covalent IMO/MC complexes may be linked by any non-covalent binding or interaction, including ionic (electrostatic) bonds, hydrophobic interactions, hydrogen bonds, van der Waals attractions, or a combination of two or more different interactions, as is normally the case when a binding pair is to link the IMO and MC. As will be understood by those of skill in the art, non-covalent IMO/MC complexes may be made by adsorption of the IMO to the MC.

Non-covalent IMO/MC complexes are typically complexed by hydrophobic or electrostatic (ionic) interactions, or a combination thereof. Due to the hydrophilic nature of the backbone of polynucleotides, IMO/MC complexes which rely on hydrophobic interactions to form the complex generally require modification of the IMO portion of the complex to incorporate a highly hydrophobic moiety. Preferably, the hydrophobic moiety is biocompatible, nonimmunogenic, and is naturally occurring in the individual for whom the composition is intended (e.g., is found in mammals, particularly humans). Examples of hydrophobic moieties include lipids, steroids, sterols such as cholesterol, and terpenes. The method of linking the hydrophobic moiety to the IMO will, of course, depend on the configuration of the IMO and the identity of the hydrophobic moiety. The hydrophobic moiety may be added at any convenient site in the IMO, preferably at either the 5' or 3' end; in the case of addition of a cholesterol moiety to an IMO, the cholesterol moiety is preferably added to the 5' end of the IMO, using conventional chemical reactions (see, for example, Godard et al. (1995) *Eur. J. Biochem.* 232:404-410). Preferably, microcarriers for use in IMO/MC complexes linked by hydrophobic bonding are made from hydrophobic materials, such as oil droplets or hydrophobic polymers, although hydrophilic materials modified to incorporate hydrophobic moieties may be utilized as well. When the microcarrier is a liposome or other liquid phase microcarrier comprising a lumen, the IMO/MC complex is formed by mixing the IMO and the MC after preparation of the MC, in order to avoid encapsulation of the IMO during the MC preparation process.

Non-covalent IMO/MC complexes bound by electrostatic binding typically exploit the highly negative charge of the polynucleotide backbone. Accordingly, microcarriers for use in non-covalently bound IMO/MC complexes are generally positively charged (e.g., cationic) at physiological pH (e.g., about pH 6.8-7.4). The microcarrier may intrinsically possess a positive charge, but microcarriers made from compounds not normally possessing a positive charge may be derivatized or otherwise modified to become positively charged (e.g., cationic). For example, the polymer used to make the microcarrier may be derivatized to add positively charged groups, such as primary amines. Alternately, positively charged compounds may be incorporated in the formulation of the microcarrier during manufacture (e.g., positively charged surfactants may be used during the manufacture of poly(lactic acid)/poly(glycolic acid) copolymers to confer a positive charge on the resulting microcarrier particles, as described, for example, in Example 2). Thus, microcarriers may comprise a positively charged moiety.

Generally, to prepare cationic microspheres, cationic lipids or polymers, for example, 1,2-dioleoyl-3-trimethylammoniumpropane (DOTAP), cetyltrimethylammonium bromide (CTAB) or polylysine, are added either to the DP or the CP, as per their solubility in these phases.

Generally, IMO/MC complexes can be preformed by adsorption onto cationic microspheres by incubation of IMO and the particles, preferably in an aqueous admixture. Such incubation may be carried out under any desired conditions, including ambient (room) temperature (e.g., approximately 20° C.) or under refrigeration (e.g., 4° C.). Because cationic microspheres and IMOs associate relatively quickly, the incubation may be for any convenient time period, such as 5, 10, 15 minutes or more, including overnight and longer incubations. However, because cationic microspheres and oligonucleotides spontaneously associate, the IMO/MC complex can be formed by simple co-administration of the IMO and the MC. Microspheres may be characterized for size and surface charge before and after IMO association. Selected batches may then be evaluated for activity against suitable controls in, for example, established human peripheral blood mononuclear cell (PBMC) and mouse splenocyte assays, as described herein. The formulations may also be evaluated in suitable animal models.

In other embodiments, a binding pair may be used to link the IMO and MC in an IMO/MC complex. The binding pair may be a receptor and ligand, an antibody and antigen (or epitope), or any other binding pair which binds at high affinity (e.g., $K_d$ less than about $10^{-8}$). One type of preferred binding pair is biotin and streptavidin or biotin and avidin, which form very tight complexes. When using a binding pair to mediate IMO/MC complex binding, the IMO is derivatized, typically by a covalent linkage, with one member of the binding pair, and the MC is derivatized with the other member of the binding pair. Mixture of the two derivatized compounds results in IMO/MC complex formation.

Many IMO/MC complex embodiments do not include an antigen, and certain embodiments exclude antigen(s) associated with the disease or disorder which is the object of the IMO/MC complex therapy. In further embodiments, the IMO is also bound to one or more antigen molecules. Antigen may be coupled with the IMO portion of an IMO/MC complex in a variety of ways, including covalent and/or non-covalent interactions, as described, for example, in WO 98/16247. Alternately, the antigen may be linked to the microcarrier (either directly or indirectly). Linkage of the antigen to the IMO can be accomplished by any of a large number of methods known in the art, including, but not limited to, direct covalent linkage, covalent conjugation via a crosslinker moiety (which may include a spacer arm), noncovalent conjugation via a specific binding pair (e.g., biotin and avidin), and noncovalent conjugation via electrostatic or hydrophobic bonding.

The link between the antigen and the IMO in IMO/MC complexes comprising an antigen bound to the IMO can be made at the 3' or 5' end of the IMO, or at a suitably modified base at an internal position in the IMO. If the antigen is a peptide and contains a suitable reactive group (e.g., an N-hydroxysuccinimide ester) it can be reacted directly with the $N^4$ amino group of cytosine residues. Depending on the number and location of cytosine residues in the IMO, specific coupling at one or more residues can be achieved.

Alternatively, modified nucleosides or nucleotides, such as are known in the art, can be incorporated at either terminus, or at internal positions in the IMO. These can contain blocked functional groups which, when deblocked, are reactive with a variety of functional groups which can be present on, or attached to, the antigen of interest.

Where the antigen is a peptide, this portion of the conjugate can be attached to the 3'-end of the IMO through solid support chemistry. For example, the IMO portion can be added to a polypeptide portion that has been pre-synthesized on a support. Haralambidis et al. (1990a) Nucleic Acids Res. 18:493-499; and Haralambidis et al. (1990b) Nucleic Acids Res. 18:501-505. Alternatively, the IMO can be synthesized such that it is connected to a solid support through a cleavable linker extending from the 3'-end. Upon chemical cleavage of the IMO from the support, a terminal thiol group is left at the 3'-end of the oligonucleotide (Zuckermann et al. (1987) Nucleic Acids Res. 15:5305-5321; and Corey et al. (1987) Science 238:1401-1403) or a terminal amino group is left at the 3'-end of the oligonucleotide (Nelson et al. (1989) Nucleic Acids Res. 17:1781-1794). Conjugation of the amino-modified IMO to amino groups of the peptide can be performed as described in Benoit et al. (1987) Neuromethods 6:43-72. Conjugation of the thiol-modified IMO to carboxyl groups of the peptide can be performed as described in Sinha et al. (1991), pp. 185-210, Oligonucleotide Analogues: A Practical Approach, IRL Press. Coupling of an oligonucleotide carrying an appended maleimide to the thiol side chain of a cysteine residue of a peptide has also been described. Tung et al. (1991) Bioconjug. Chem. 2:464-465.

The peptide portion of the conjugate can be attached to the 5'-end of the IMO through an amine, thiol, or carboxyl group that has been incorporated into the oligonucleotide during its synthesis. Preferably, while the oligonucleotide is fixed to the solid support, a linking group comprising a protected amine, thiol, or carboxyl at one end, and a phosphoramidite at the other, is covalently attached to the 5'-hydroxyl. Agrawal et al. (1986) Nucleic Acids Res. 14:6227-6245; Connolly (1985) Nucleic Acids Res. 13:4485-4502; Kremsky et al. (1987) Nucleic Acids Res. 15:2891-2909; Connolly (1987) Nucleic Acids Res. 15:3131-3139; Bischoff et al. (1987) Anal. Biochem. 164:336-344; Blanks et al. (1988) Nucleic Acids Res. 16:10283-10299; and U.S. Pat. Nos. 4,849,513, 5,015,733, 5,118,800, and 5,118,802. Subsequent to deprotection, the amine, thiol, and carboxyl functionalities can be used to covalently attach the oligonucleotide to a peptide. Benoit et al. (1987); and Sinha et al. (1991).

An IMO-antigen conjugate can also be formed through non-covalent interactions, such as ionic bonds, hydrophobic interactions, hydrogen bonds and/or van der Waals attractions.

Non-covalently linked conjugates can include a non-covalent interaction such as a biotin-streptavidin complex. A biotinyl group can be attached, for example, to a modified base of an IMO. Roget et al. (1989) Nucleic Acids Res. 17:7643-7651. Incorporation of a streptavidin moiety into the peptide portion allows formation of a non-covalently bound complex of the streptavidin conjugated peptide and the biotinylated oligonucleotide.

Non-covalent associations can also occur through ionic interactions involving an IMO and residues within the antigen, such as charged amino acids, or through the use of a linker portion comprising charged residues that can interact with both the oligonucleotide and the antigen. For example, non-covalent conjugation can occur between a generally negatively-charged IMO and positively-charged amino acid residues of a peptide, e.g., polylysine, polyarginine and polyhistidine residues.

Non-covalent conjugation between IMO and antigens can occur through DNA binding motifs of molecules that interact with DNA as their natural ligands. For example, such DNA binding motifs can be found in transcription factors and anti-DNA antibodies.

The linkage of the IMO to a lipid can be formed using standard methods. These methods include, but are not limited to, the synthesis of oligonucleotide-phospholipid conjugates (Yanagawa et al. (1988) Nucleic Acids Symp. Ser. 19:189-192), oligonucleotide-fatty acid conjugates (Grabarek et al. (1990) Anal. Biochem. 185:131-135; and Staros et al. (1986) Anal. Biochem. 156:220-222), and oligonucleotide-sterol conjugates. Boujrad et al. (1993) Proc. Natl. Acad. Sci. USA 90:5728-5731.

The linkage of the IMO to an oligosaccharide can be formed using standard known methods. These methods include, but are not limited to, the synthesis of oligonucleotide-oligosaccharide conjugates, wherein the oligosaccharide is a moiety of an immunoglobulin. O'Shannessy et al. (1985) J. Applied Biochem. 7:347-355.

Additional methods for the attachment of peptides and other molecules to oligonucleotides can be found in U.S. Pat. No. 5,391,723; Kessler (1992) "Nonradioactive labeling methods for nucleic acids" in Kricka (ed.) Nonisotopic DNA Probe Techniques, Academic Press; and Geoghegan et al. (1992) Bioconjug. Chem. 3:138-146.

IMO Encapsulated within MC

In another aspect of the invention, an IMO is encapsulated within a microcarrier ("IMO/MC encapsulate"), and preferably multiple molecules of IMO are encapsulated within each microcarrier. In certain embodiments, a mixture of different IMOs may be encapsulated with a microcarrier, such that the microcarrier encapsulates more than one IMO species. In certain of embodiments where the IMO is a encapsulated within the MC, the IMO is a 3mer, 4mer or 5mer (3-5mer). In certain embodiments where the IMO is encapsulated within the MC, the IMO may be any 6-mer described herein excluding the sequences 5'-TTCGAA-3',5'-GACGTT-3', and/or 5'-GAGCTT-3', for example, the 6-mer IMO has the sequence 5'-$X_1$TCG$X_2$-3' or 5'-$X_1$UCG$X_2$-3', where $X_1$ is zero or one nucleotide, and $X_2$ is zero to three nucleotides. Additional examples of IMOs which may be utilized in IMO/MC encapsulates are described above.

Methods of encapsulating oligonucleotides in microcarriers are well known in the art, and described, for example, International application WO98/55495. Colloidal dispersion systems, such as microspheres, beads, macromolecular complexes, nanocapsules and lipid-based system, such as oil-in-water emulsions, micelles, mixed micelles and liposomes can provide effective encapsulation of IMO within MC compositions. The encapsulation composition may further comprise any of a wide variety of components. These include, but are not limited to, alum, lipids, phospholipids, lipid membrane structures (LMS), polyethylene glycol (PEG) and other polymers, such as polypeptides, glycopeptides, and polysaccharides.

Methods of the Invention

The invention provides methods of modulating an immune response in an individual, preferably a mammal, more preferably a human, comprising administering to the individual an IMO/MC complex or encapsulate (typically in a composition comprising the complex or encapsulate and a pharmaceutically acceptable excipient) such that the desired modulation of the immune response is achieved. Immunomodulation may include stimulating a Th1-type immune response and/or inhibiting or reducing a Th2-type immune response.

In some embodiments, the immune modulation comprises stimulating a (i.e., one or more) Th1-associated cytokine, such as IFN-γ, IL-12 and/or IFN-α. In some embodiments, the immune modulation comprises suppressing production of a (i.e., one or more) Th2-associated cytokine, such as IL-4 and/or IL-5. Measuring these parameters uses methods standard in the art and has been discussed herein.

As described herein, administration of IMO/MC may further comprise administration of one or more additional immunotherapeutic agents (i.e., an agent which acts via the immune system and/or is derived from the immune system) including, but not limited to, cytokine, adjuvants and antibodies. Examples of therapeutic antibodies include those used in the cancer context (e.g., anti-tumor antibodies). Administration of such additional immunotherapeutic agents applies to all the methods described herein. In the cancer context, administration of IMO/MC complex or encapsulate may further comprise administration of one or more additional therapeutic agents such as, for example, anti-tumor antibodies, chemotherapy regimens and/or radiation treatments. Anti-tumor antibodies, including, but not limited to anti-tumor antibody fragments and/or derivatives thereof, and monoclonal anti-tumor antibodies, fragments and/or derivatives thereof, are known in the art and as is administration of such antibody reagents in cancer therapy (e.g., Rituximab; Herceptin). Administration of one or more additional therapeutic agents may occur before, after and/or concurrent with administration of the IMO/MC complexes or encapsulates.

In certain embodiments, the individual suffers from a disorder associated with a Th2-type immune response, such as allergies or allergy-induced asthma. Administration of an IMO/MC complex or encapsulate results in immunomodulation, increasing levels of one or more Th1-type response associated cytokines, which may result in a reduction of the Th2-type response features associated with the individual's response to the allergen. Immunomodulation of individuals with Th2-type response associated disorders results in a reduction or improvement in one or more of the symptoms of the disorder. Where the disorder is allergy or allergy-induced asthma, improvement in one or more of the symptoms includes a reduction one or more of the following: rhinitis, allergic conjunctivitis, circulating levels of IgE, circulating levels of histamine and/or requirement for 'rescue' inhaler therapy (e.g., inhaled albuterol administered by metered dose inhaler or nebulizer). It should be noted that the methods of the invention relating to the treatment of asthma are believed to be a treatment of the underlying causes which results in amelioration of one or more symptoms of asthma. Accordingly, an individual that suffers from asthma is an individual who has been diagnosed with asthma, and need not be suffering acute asthma at or near the time of treatment.

In further embodiments, the individual subject to the immunomodulatory therapy of the invention is an individual receiving a vaccine. The vaccine may be a prophylactic vaccine or a therapeutic vaccine. A prophylactic vaccine comprises one or more epitopes associated with a disorder for which the individual may be at risk (e.g., *M. tuberculosis* antigens as a vaccine for prevention of tuberculosis, allergens as a vaccine for prevention of allergies, tumor associated antigens for prevention of cancer). Therapeutic vaccines comprise one or more epitopes associated with a particular disorder affecting the individual, such as *M. tuberculosis* or *M. Bovis* surface antigens in tuberculosis patients, antigens to which the individual is allergic (i.e., allergy desensitization therapy) in individuals subject to allergies, tumor cells from an individual with cancer (e.g., as described in U.S. Pat. No. 5,484,596), or tumor associated antigens in cancer patients. The IMO/MC complex or encapsulate may be given in conjunction with the vaccine (e.g., in the same injection or a contemporaneous, but separate, injection) or the IMO/MC complex or encapsulate may be administered separately (e.g., at least 12 hours before or after administration of the vaccine). In certain embodiments, the antigen(s) of the vaccine is part of the IMO/MC complex or encapsulate, by either covalent or non-covalent linkage to the IMO/MC complex or encapsulate. Administration of IMO/MC complex or encapsulate therapy to an individual receiving a vaccine results in an immune response to the vaccine that is shifted towards a Th1-type response as compared to individuals which receive vaccine without IMO/MC complex or encapsulate. Shifting towards a Th1-type response may be recognized by a delayed-type hypersensitivity (DTH) response to the antigen(s) in the vaccine, increased IFN-γ and other Th1-type response associated cytokines, increased IFN-α, production of CTLs specific for the antigen(s) of the vaccine, low or reduced levels of IgE specific for the antigen(s) of the vaccine, a reduction in Th2-associated antibodies specific for the antigen(s) of the vaccine, and/or an increase in Th1-associated antibodies specific for the antigen(s) of the vaccine. In the case of therapeutic vaccines, administration of IMO/MC complex or encapsulate and vaccine also results in amelioration of the symptoms of the disorder which the vaccine is intended to treat. As will be apparent to one of skill in the art, the exact symptoms and manner of their improvement will depend on the disorder sought to be treated. For example, where the therapeutic vaccine is for tuberculosis, IMO/MC complex or encapsulate treatment with vaccine results in reduced coughing, pleural or chest wall pain, fever, and/or other symptoms known in the art. Where the vaccine is an allergen used in allergy desensitization therapy, the treatment results in a reduction in one or more symptoms of allergy (e.g., reduction in rhinitis, allergic conjunctivitis, circulating levels of IgE, and/or circulating levels of histamine).

Other embodiments of the invention relate to immunomodulatory therapy of individuals having a pre-existing disease or disorder, such as cancer or an infectious disease. Cancer is an attractive target for immunomodulation because most cancers express tumor-associated and/or tumor specific antigens which are not found on other cells in the body. Stimulation of a Th1-type response against tumor cells results in direct and/or bystander killing of tumor cells by the immune system, leading to a reduction in cancer cells and a reduction in symptoms. Administration of an IMO/MC complex or encapsulate to an individual having cancer results in stimulation of a Th1-type immune response against the tumor cells. Such an immune response can kill tumor cells, either by direct action of cellular immune system cells (e.g., CTLs) or components of the humoral immune system, or by bystander effects on cells proximal to cells targeted by the immune system.

Immunomodulatory therapy in accordance with the invention is also useful for individuals with infectious diseases, particularly infectious diseases which are resistant to humoral immune responses (e.g., diseases caused by mycobacterial infections and intracellular pathogens). Immunomodulatory therapy may be used for the treatment of infectious diseases caused by cellular pathogens (e.g., bacteria or protozoans) or by subcellular pathogens (e.g., viruses). IMO/MC complex or encapsulate therapy may be administered to individuals suffering from mycobacterial diseases such as tuberculosis (e.g., *M. tuberculosis* and/or *M. Bovis* infections), leprosy (i.e., *M. leprae* infections), or *M. marinum* or *M. ulcerans* infections. IMO/MC complex or encapsulate therapy is also useful for the treatment of viral infections, including infections by influenza virus, respiratory syncytial virus (RSV), hepatitis virus B, hepatitis virus C, herpes viruses, particularly herpes simplex viruses (including HSV2), and papilloma viruses. Diseases caused by intracellular parasites such as malaria (e.g., infection by *Plasmodium vivax, P. ovale, P. falciparum* and/or *P. malariae*), leishmaniasis (e.g., infection by *Leishmania donovani, L. tropica, L. mexicana, L. braziliensis, L. peruviana, L. infantum, L. chagasi*, and/or *L. aethiopica*), and toxoplasmosis (i.e., infection by *Toxoplasmosis gondii*) also benefit from IMO/MC complex encapsulate therapy. IMO/MC therapy is also useful for treatment of parasitic diseases such as schistosomiasis (i.e., infection by blood flukes of the genus *Schistosoma* such as *S. haematobium, S. mansoni, S. japonicum*, and *S. mekongi*) and clonorchiasis (i.e., infection by *Clonorchis sinensis*). Administration of an IMO/MC complex or encapsulate to an individual suffering from an infectious disease results in an amelioration of one or more symptoms of the infectious disease.

The invention further provides methods of increasing at least one Th1-associated cytokine in an individual, including IL-2, IL-12, TNF-β, and IFN-γ. In certain embodiments, the invention provides methods of increasing IFN-γ in an individual, particularly in an individual in need of increased IFN-γ levels, by administering an effective amount of an IMO/MC complex or encapsulate to the individual. Individuals in need of increased IFN-γ are those having disorders which respond to the administration of IFN-γ. Such disorders include a number of inflammatory disorders including, but not limited to, ulcerative colitis. Such disorders also include a number of fibrotic disorders, including, but not limited to, idiopathic pulmonary fibrosis (IPF), scleroderma, cutaneous radiation-induced fibrosis, hepatic fibrosis including schistosomiasis-induced hepatic fibrosis, renal fibrosis as well as other conditions which may be improved by administration of IFN-γ. Administration of IMO/MC complex or encapsulate in accordance with the invention results in an increase in IFN-γ levels, and results in amelioration of one or more symptoms, stabilization of one or more symptoms, or prevention of progression (e.g., reduction or elimination of additional lesions or symptoms) of the disorder which responds to IFN-γ. The methods of the invention may be practiced in combination with other therapies which make up the standard of care for the disorder, such as administration of anti-inflammatory agents such as systemic corticosteroid therapy (e.g., cortisone) in IPF.

In certain embodiments, the invention provides methods of increasing IFN-α in an individual, particularly in an individual in need of increased IFN-α levels, by administering an effective amount of an IMO/MC complex or encapsulate to the individual such that IFN-α levels are increased. Individuals in need of increased IFN-α are those having disorders which respond to the administration of IFN-α, including recombinant IFN-α, including, but not limited to, viral infections and cancer.

Administration of an IMO/MC complex or encapsulate in accordance with the invention results in an increase in IFN-α levels, and results in amelioration of one or more symptoms, stabilization of one or more symptoms, or prevention of progression (e.g., reduction or elimination of additional lesions or symptoms) of the disorder which responds to IFN-α. The methods of the invention may be practiced in combination with other therapies which make up the standard of care for the disorder, such as administration of anti-viral agents for viral infections.

Also provided are methods of reducing levels, particularly serum levels, of IgE in an individual having an IgE-related disorder by administering an effective amount of an IMO/MC complex or encapsulate to the individual such that levels of IgE are reduced. Reduction in IgE results in an amelioration of symptoms of the IgE-related disorder. Such symptoms include allergy symptoms such as rhinitis, conjunctivitis, in decreased sensitivity to allergens, a reduction in the symptoms of allergy in an individual with allergies, or a reduction in severity of a allergic response.

As will be apparent to one of skill in the art, the methods of the invention may be practiced in combination with other therapies for the particular indication for which the IMO/MC complex or encapsulate is administered. For example, IMO/MC complex or encapsulate therapy may be administered in conjunction with anti-malarial drugs such as chloroquine for malaria patients, in conjunction with leishmanicidal drugs such as pentamidine and/or allopurinol for leishmaniasis patients, in conjunction with anti-mycobacterial drugs such as isoniazid, rifampin and/or ethambutol in tuberculosis patients, or in conjunction with allergen desensitization therapy for atopic (allergy) patients.

Administration and Assessment of the Immune Response

The IMO/MC complex or encapsulate can be administered in combination with other pharmaceutical and/or immunogenic and/or immunostimulatory agents and can be combined with a physiologically acceptable carrier thereof.

Accordingly, the IMO/MC complex or encapsulate can be administered in conjunction with other immunotherapeutic agents including, but not limited to, cytokine, adjuvants and antibodies.

The IMO/MC complex or encapsulate may comprise any combination of the IMOs and MCs described above, so long as the IMO/MC is active. Generally, in some embodiments, an IMO/MC complex or encapsulate will be considered active if it has an activity (i.e., affects a measurable immune response as measured in vitro, in vivo and/or ex vivo) of at least two times, preferably at least three times, more preferably at least five times, even more preferably ten times the activity of a negative control in at least one assay of activity. Methods of assessing a measurable immune response are well known in the art, and include the human PBMC assay disclosed herein.

As with all immunogenic compositions, the immunologically effective amounts and method of administration of the particular IMO/MC complex or encapsulate formulation can vary based on the individual, what condition is to be treated and other factors evident to one skilled in the art. Factors to be considered include the antigenicity, whether or not the IMO/MC complex or encapsulate will be administered with or covalently attached to an adjuvant or delivery molecule, route of administration and the number of immunizing doses to be administered. Such factors are known in the art and it is well within the skill of those in the art to make such determinations without undue experimentation. A suitable dosage range is one that provides the desired modulation of immune response to the antigen. Generally, dosage is determined by the amount of IMO administered to the patient, rather than the overall quantity of IMO/MC complex or encapsulate. Useful dosage ranges of the IMO/MC complex or encapsulate, given in amounts of IMO administered, may be, for example, from about any of the following: 0.1 to 100 µg/kg, 0.1 to 50 µg/kg, 0.1 to 25 µg/kg, 0.1 to 10 µg/kg, 1 to 500 µg/kg, 100 to 400 µg/kg, 200 to 300 µg/kg, 1 to 100 µg/kg, 100 to 200 µg/kg, 300 to 400 µg/kg, 400 to 500 µg/kg. Alternatively, the doses can be about any of the following: 0.1 µg, 0.25 µg, 0.5 µg, 1.0 µg, 2.0 µg, 5.0 µg, 10 µg, 25 µg, 50 µg, 75 µg, 100 µg. Accordingly, dose ranges can be those with a lower limit about any of the following: 0.1 µg, 0.25 µg, 0.5 µg and 1.0 µg; and with an upper limit of about any of the following: 25 µg, 50 µg and 100 µg. The absolute amount given to each patient depends on pharmacological properties such as bioavailability, clearance rate and route of administration.

The effective amount and method of administration of the particular IMO/MC complex or encapsulate formulation can vary based on the individual patient and the stage of the disease and other factors evident to one skilled in the art. The route(s) of administration useful in a particular application are apparent to one of skill in the art. Routes of administration include but are not limited to topical, dermal, transdermal, transmucosal, epidermal, parenteral, gastrointestinal, and naso-pharyngeal and pulmonary, including transbronchial and transalveolar. A suitable dosage range is one that provides sufficient IMO/MC complex or encapsulate to attain a tissue concentration of about 1-10 µM as measured by blood levels. The absolute amount given to each patient depends on pharmacological properties such as bioavailability, clearance rate and route of administration.

As described herein, APCs and tissues with high concentration of APCs are preferred targets for the IMO/MC complexes or encapsulates. Thus, administration of IMO/MC complex or encapsulate to mammalian skin and/or mucosa, where APCs are present in relatively high concentration, is preferred.

The present invention provides IMO/MC complex or encapsulate formulations suitable for topical application including, but not limited to, physiologically acceptable implants, ointments, creams, rinses and gels. Topical administration is, for instance, by a dressing or bandage having dispersed therein a delivery system, by direct administration of a delivery system into incisions or open wounds, or by transdermal administration device directed at a site of interest. Creams, rinses, gels or ointments having dispersed therein an IMO/MC complex encapsulate are suitable for use as topical ointments or wound filling agents.

Preferred routes of dermal administration are those which are least invasive. Preferred among these means are transdermal transmission, epidermal administration and subcutaneous injection. Of these means, epidermal administration is preferred for the greater concentrations of APCs expected to be in intradermal tissue.

Transdermal administration is accomplished by application of a cream, rinse, gel, etc. capable of allowing the IMO/MC complex or encapsulate to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference.

For transdermal transmission, iontophoresis is a suitable method. Iontophoretic transmission can be accomplished using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

An exemplary patch product for use in this method is the LECTRO PATCH trademarked product of General Medical Company of Los Angeles, Calif. This product electronically maintains reservoir electrodes at neutral pH and can be adapted to provide dosages of differing concentrations, to dose continuously and/or periodically. Preparation and use of the patch should be performed according to the manufacturer's printed instructions which accompany the LECTRO PATCH product; those instructions are incorporated herein by this reference. Other occlusive patch systems are also suitable.

For transdermal transmission, low-frequency ultrasonic delivery is also a suitable method. Mitragotri et al. (1995) *Science* 269:850-853. Application of low-frequency ultrasonic frequencies (about 1 MHz) allows the general controlled delivery of therapeutic compositions, including those of high molecular weight.

Epidermal administration essentially involves mechanically or chemically irritating the outermost layer of the epidermis sufficiently to provoke an immune response to the irritant. Specifically, the irritation should be sufficient to attract APCs to the site of irritation.

An exemplary mechanical irritant means employs a multiplicity of very narrow diameter, short tines which can be used to irritate the skin and attract APCs to the site of irritation, to take up IMO/MC complex or encapsulate transferred from the end of the tines. For example, the MONO-VACC old tuberculin test manufactured by Pasteur Merieux of Lyon, France contains a device suitable for introduction of IMO/MC complex- or encapsulate-containing compositions.

The device (which is distributed in the U.S. by Connaught Laboratories, Inc. of Swiftwater, Pa.) consists of a plastic container having a syringe plunger at one end and a tine disk at the other. The tine disk supports a multiplicity of narrow diameter tines of a length which will just scratch the outermost layer of epidermal cells. Each of the tines in the MONO-VACC kit is coated with old tuberculin; in the present invention, each needle is coated with a pharmaceutical composition of IMO/MC complex or encapsulate formulation. Use of the device is preferably according to the manufacturer's written instructions included with the device product. Similar devices which can also be used in this embodiment are those which are currently used to perform allergy tests.

Another suitable approach to epidermal administration of IMO/MC complex or encapsulate is by use of a chemical which irritates the outermost cells of the epidermis, thus provoking a sufficient immune response to attract APCs to the area. An example is a keratinolytic agent, such as the salicylic acid used in the commercially available topical depilatory creme sold by Noxema Corporation under the trademark NAIR®. This approach can also be used to achieve epithelial administration in the mucosa. The chemical irritant can also be applied in conjunction with the mechanical irritant (as, for example, would occur if the MONO-VACC type tine were also coated with the chemical irritant). The IMO/MC complex or encapsulate can be suspended in a carrier which also contains the chemical irritant or coadministered therewith.

Parenteral routes of administration include but are not limited to electrical (iontophoresis) or direct injection such as direct injection into a central venous line, intravenous, intramuscular, intraperitoneal, intradermal, or subcutaneous injection. IMO/MC formulations suitable for parenteral administration are generally formulated in USP water or water for injection and may further comprise pH buffers, salts bulking agents, preservatives, and other pharmaceutically acceptable excipients. IMO/MC complexes or encapsulates for parenteral injection may be formulated in pharmaceutically acceptable sterile isotonic solutions such as saline and phosphate buffered saline for injection.

Gastrointestinal routes of administration include, but are not limited to, ingestion and rectal. The invention includes IMO/MC complex or encapsulate formulations suitable for gastrointestinal administration including, but not limited to, pharmaceutically acceptable powders, pills or liquids for ingestion and suppositories for rectal administration. As will be apparent to one of skill in the art, pills or suppositories will further comprise pharmaceutically acceptable solids, such as starch, to provide bulk for the composition.

Naso-pharyngeal and pulmonary administration include are accomplished by inhalation, and include delivery routes such as intranasal, transbronchial and transalveolar routes. The invention includes IMO/MC complex or encapsulate formulations suitable for administration by inhalation including, but not limited to, liquid suspensions for forming aerosols as well as powder forms for dry powder inhalation delivery systems. Devices suitable for administration by inhalation of IMO/MC complex or encapsulate formulations include, but are not limited to, atomizers, vaporizers, nebulizers, and dry powder inhalation delivery devices.

The choice of delivery routes can be used to modulate the immune response elicited. For example, IgG titers and CTL activities were identical when an influenza virus vector was administered via intramuscular or epidermal (gene gun) routes; however, the muscular inoculation yielded primarily IgG2a, while the epidermal route yielded mostly IgG1. Pertmer et al. (1996) *J. Virol.* 70:6119-6125. Thus, one skilled in the art can take advantage of slight differences in immunogenicity elicited by different routes of administering the immunomodulatory oligonucleotides of the present invention.

The above-mentioned compositions and methods of administration are meant to describe but not limit the methods of administering the IMO/MC complex or encapsulate formulations of the invention. The methods of producing the various compositions and devices are within the ability of one skilled in the art and are not described in detail here.

Analysis (both qualitative and quantitative) of the activity of IMO/MC complex or encapsulate formulations can be by any method known in the art, including, but not limited to, measuring antigen-specific antibody production (including measuring specific antibody subclasses), activation of specific populations of lymphocytes such as CD4+ T cells or NK cells, production of cytokines such as IFN-γ, IFN-α, IL-2, IL-4, IL-5, IL-10 or IL-12 and/or release of histamine. Methods for measuring specific antibody responses include enzyme-linked immunosorbent assay (ELISA) and are well known in the art. Measurement of numbers of specific types of lymphocytes such as CD4+ T cells can be achieved, for example, with fluorescence-activated cell sorting (FACS). Cytotoxicity assays can be performed for instance as described in Raz et al. (1994) *Proc. Natl. Acad. Sci. USA* 91:9519-9523. Cytokine concentrations can be measured, for example, by ELISA. These and other assays to evaluate the immune response to an immunogen are well known in the art. See, for example, Selected Methods in Cellular Immunology (1980) Mishell and Shiigi, eds., W.H. Freeman and Co. One preferred method of measuring the activity of an IMO/MC complex or encapsulate is an assay which measures the response of peripheral blood mononuclear cells (PBMCs, preferably human PBMCs) to the IMO/MC complex or encapsulate, such as that described below in the Examples.

Preferably, a Th1-type response is stimulated, i.e., elicited and/or enhanced. With reference to the invention, stimulating a Th1-type immune response can be determined in vitro or ex vivo by measuring cytokine production from cells treated with IMO/MC complex or encapsulate as compared to those treated without IMO/MC complex or encapsulate. Methods to determine the cytokine production of cells include those methods described herein and any known in the art. The type of cytokines produced in response to IMO/MC complex or encapsulate treatment indicate a Th1-type or a Th2-type biased immune response by the cells. As used herein, the term "Th1-type biased" cytokine production refers to the measurable increased production of cytokines associated with a Th1-type immune response in the presence of a stimulator as compared to production of such cytokines in the absence of stimulation. Examples of such Th1-type biased cytokines include, but are not limited to, IL-2, IL-12, and IFN-γ. In contrast, "Th2-type biased cytokines" refers to those associated with a Th2-type immune response, and include, but are not limited to, IL-4, IL-5, and IL-13. Cells useful for the determination of IMO/MC complex or encapsulate activity include cells of the immune system, primary cells isolated from a host and/or cell lines, preferably APCs and lymphocytes, even more preferably macrophages and T cells.

Stimulating a Th1-type immune response can also be measured in a host treated with an IMO/MC complex or encapsulate formulation can be determined by any method known in the art including, but not limited to: (1) a reduction in levels of IL-4 or IL-5 measured before and after antigen-challenge; or detection of lower (or even absent) levels of IL-4 or IL-5 in an IMO/MC complex or encapsulate treated host as compared to an antigen-primed, or primed and challenged, control treated without IMO; (2) an increase in levels of IL-12, IL-18 and/or IFN (α, β or γ) before and after antigen challenge; or detection of higher levels of IL-12, IL-18 and/or IFN (α, β or γ) in an IMO/MC complex or encapsulate treated host as compared to an antigen-primed or, primed and challenged, control treated without IMO; (3) "Th1-type biased" antibody production in an IMO/MC complex or encapsulate treated host as compared to a control treated without IMO; and/or (4) a reduction in levels of antigen-specific IgE as measured before and after antigen challenge; or detection of lower (or even absent) levels of antigen-specific IgE in an IMO/MC complex or encapsulate treated host as compared to an antigen-primed, or primed and challenged, control treated without IMO. A variety of these determinations can be made by measuring cytokines made by APCs and/or lymphocytes, preferably macrophages and/or T cells, in vitro or ex vivo using methods described herein or any known in the art. Some of these determinations can be made by measuring the class and/or subclass of antigen-specific antibodies using methods described herein or any known in the art.

The class and/or subclass of antigen-specific antibodies produced in response to IMO/MC complex or encapsulate treatment indicate a Th1-type or a Th2-type biased immune response by the cells. As used herein, the term "Th1-type biased" antibody production refers to the measurable increased production of antibodies associated with a Th1- type immune response (i.e., Th1-associated antibodies). One or more Th1 associated antibodies may be measured. Examples of such Th1-type biased antibodies include, but are not limited to, human IgG1 and/or IgG3 (see, e.g., Widhe et al. (1998) *Scand. J. Immunol.* 47:575-581 and de Martino et al. (1999) *Ann. Allergy Asthma Immunol.* 83:160-164) and murine IgG2a. In contrast, "Th2-type biased antibodies" refers to those associated with a Th2-type immune response, and include, but are not limited to, human IgG2, IgG4 and/or IgE (see, e.g., Widhe et al. (1998) and de Martino et al. (1999)) and murine IgG1 and/or IgE.

The Th1-type biased cytokine induction which occurs as a result of IMO/MC complex or encapsulate administration produces enhanced cellular immune responses, such as those performed by NK cells, cytotoxic killer cells, Th1 helper and memory cells. These responses are particularly beneficial for use in protective or therapeutic vaccination against viruses, fungi, protozoan parasites, bacteria, allergic diseases and asthma, as well as tumors.

In some embodiments, a Th2 response is suppressed. Suppression of a Th2 response may be determined by, for example, reduction in levels of Th2-associated cytokines, such as IL-4 and IL-5, as well as IgE reduction and reduction in histamine release in response to allergen.

Kits of the Invention

The invention provides kits for use in the methods of the invention. In certain embodiments, the kits of the invention comprise one or more containers comprising an IMO/MC complex or encapsulate and, optionally, a set of instructions, generally written instructions, relating to the use of the IMO/MC complex or encapsulate for the intended treatment (e.g., immunomodulation, ameliorating one or more symptoms of an infectious disease, increasing IFN-γ levels, increasing IFN-α levels, or ameliorating an IgE-related disorder). In further embodiments, the kits of the invention comprise containers of materials for producing IMO/MC, instructions for producing IMO/MC complex or encapsulate, and, optionally, instructions relating to the use of the IMO/MC complex or encapsulate for the intended treatment.

Kits which comprise preformed IMO/MC complex or encapsulate comprise IMO/MC complex or encapsulate packaged in any convenient, appropriate packaging. For example, if the IMO/MC complex or encapsulate is a dry formulation (e.g., freeze dried or a dry powder), a vial with a resilient stopper is normally used, so that the IMO/MC complex or encapsulate may be easily resuspended by injecting fluid through the resilient stopper. Ampoules with non-resilient, removable closures (e.g., sealed glass) or resilient stoppers are most conveniently used for liquid formulations of IMO/MC complex or encapsulate. Also contemplated are packages for use in combination with a specific device, such as an inhaler, nasal administration device (e.g., an atomizer) or an infusion device such as a minipump.

Kits which comprise materials for production of IMO/MC complex or encapsulate generally include separate containers of IMO and MC, although in certain embodiments materials for producing the MC (particularly for IMO/MC encapsulates) are supplied rather than preformed MC. The IMO and MC are preferably supplied in a form which allows formation of IMO/MC complex or encapsulate upon mixing of the supplied IMO and MC. This configuration is preferred when the IMO/MC complex is linked by non-covalent bonding or when an IMO/MC encapsulate is desired. This configuration is also preferred when the IMO and MC are to be crosslinked via a heterobifunctional crosslinker; either IMO or the MC is supplied in an "activated" form (e.g., linked to the heterobifunctional crosslinker such that a moiety reactive with the IMO is available).

Kits for IMO/MC complexes or encapsulates comprising a liquid phase MC preferably comprise one or more containers including materials for producing liquid phase MC. For example, an IMO/MC kit for oil-in-water emulsion MC may comprise one or more containers containing an oil phase and an aqueous phase. The contents of the container are emulsified to produce the MC, which may be then mixed with the IMO, preferably an IMO which has been modified to incorporate a hydrophobic moiety. Alternately, the IMO and the material for preparation of the MC may be first combined, then emulsified to produce IMO encapsulated in the newly formed MC. Such materials include oil and water, for production of oil-in-water emulsions, or containers of lyophilized liposome components (e.g., a mixture of phospholipid, cholesterol and a surfactant) plus one or more containers of an aqueous phase (e.g., a pharmaceutically-acceptable aqueous buffer).

The instructions relating to the use of IMO/MC complex for the intended treatment generally include information as to dosage, dosing schedule, and route of administration for the intended treatment. The containers of IMO/MC (or separate containers of IMO and MC for local production of IMO/MC complex) may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The following Examples are provided to illustrate, but not limit, the invention.

EXAMPLES

Example 1

Synthesis of Immunomodulatory Oligonucleotides

Oligonucleotides containing phosphorothiate linkages were synthesized on a Perseptive Biosystems Expedite 8909 automated DNA synthesizer. The manufacturer's protocol for 15 µmol phosphorothioate DNA was used with the following changes: 1.6 ml of 3% dichloroacetic acid in dichloromethane over 2.5 min was used for the detritylation step; and 3.0 ml of 0.02 M 3-amino-1,2,4-dithiazole-5-thione (ADTT) in 9:1 acetonitrile:pyridine over 1.1 min followed by a 1.0 ml delivery over 1.0 min was used for the sulfurization step. The nucleoside phosphoramidite monomers were dissolved in anhydrous acetonitrile to a concentration of 0.1 M. The instrument was programmed to add the nucleotide monomers in the desired order, with the synthesis occurring in the 3' to 5' direction. The synthesis cycle consisted of a detritylation step, a coupling step (phosphoramidite monomer plus 1H-tetrazole), a capping step, a sulfurization step, and a final capping step.

Oligonucleotides containing phosphodiester linkages (e.g., 6-12) were synthesized on a Perseptive Biosystems Expedite 8909 automated DNA synthesizer. The manufacturer's protocol for 15 umol phosphodiester DNA was used with the following changes: 1.6 ml of 3% dichloroacetic acid in dichloromethane over 2.5 min was used for the detritylation step; and 3.0 ml of oxidation reagent over 1.1 min followed by a 1.0 ml delivery over 1.0 min was used for the oxidation step. The nucleoside phosphoramidite monomers were dissolved in anhydrous acetonitrile to a concentration of 0.1 M. The instrument was programmed to add the nucleotide monomers in the desired order, with the synthesis occurring in the 3' to 5' direction. The synthesis cycle consisted of a detritylation step, a coupling step (phosphoramidite monomer plus 1H-tetrazole), a capping step, an oxidation step, and a final capping step.

IMOs were purified by RP-HPLC on a Polymer Labs PLRP-S column using an increasing gradient of acetonitrile in 0.1 M triethylammonium acetate. The purified IMOs were concentrated to dryness, the 4,4'-dimethoxytrityl group was removed with 80% aqueous acetic acid, and then the compound was precipitated two times from 0.6 M aqueous sodium acetate/pH 5.0 with 3 volumes of isopropanol. The IMOs were dissolved in Milli Q water and the yield was determined from the absorbance at 260 nm. Finally, the IMOs were lyophilized to a powder.

The IMOs were characterized by capillary gel electrophoresis, electrospray mass spectrometry, and RP-HPLC to confirm composition and purity. An endotoxin content assay (LAL assay, Bio Whittaker) was also conducted, showing endotoxin levels were <5 EU/mg IMO.

Table 2 lists names of various oligonucleotides and their sequences. The core trimer is underlined in those oligonucleotides having a core 5'-TCG-3' or 5'-UCG-3' trimer. Oligonucleotides listed in this table have phosphorothioate-linked backbones unless otherwise noted.

TABLE 2

| Name | Sequence | Comments |
|---|---|---|
| 6-1 | 5'-TCGTCG-3' | |
| 6-2 | 5'-TCGTTT-3' | |
| 6-3 | 5'-TTCGTT-3' | |
| 6-4 | 5'-TTTCGT-3' | |
| 6-5 | 5'-TTTTCG-3' | |
| 6-6 | 5'-TCGAGA-3' | |
| 6-7 | 5'-ATCGAT-3' | |
| 6-8 | 5'-GTCGAC-3' | |
| 6-9 | 5'-GTCGTT-3' | |
| 6-10 | 5'-TCGCGA-3' | |
| 6-11 | 5'-CGATCG-3' | |
| 6-12 | 5'-TCGTCG-3' | phosphodiester linkages |
| 6-13 | 5'-ACGTTT-3' | |
| 6-14 | 5'-CCGTTT-3' | |
| 6-15 | 5'-GCGTTT-3' | |
| 6-16 | 5'-AACGTT-3' | |
| 6-17 | 5'-GACGTT-3' | |
| 6-18 | 5'-TCCGGA-3' | |
| 6-19 | 5'-GAGCTT-3' | |
| 6-20 | 5'-TCCTTT-3' | |
| 6-21 | 5'-UCGTTT-3' | U = 2'-deoxyuridine |
| 6-22 | 5'-TZ$_1$GTTT-3' | Z$_1$ = 5-bromo-2'-deoxycytidine |
| 6-23 | 5'-TZ$_1$GTTT-3' | Z$_1$ = N4-ethyl-2'-deoxycytidine |
| 6-24 | 5'-TCZ$_1$TTT-3' | Z$_1$ = 7-deaza-2'-deoxyguanidine |
| 6-25 | 5'-AATCGT-3' | |
| 5-1 | 5'-TCGTC-3' | |
| 5-2 | 5'-TCGTT-3' | |
| 5-3 | 5'-TTCGT-3' | |
| 4-1 | 5'-TCGT-3' | |
| 3-1 | 5'-TCG-3' | |

Example 2

Preparation of Biodegradable Microcarriers

Cationic poly(lactic acid, glycolic acid) microspheres (cPLGA) were prepared as follows. 0.875 g of poly (D,L-lactide-co-glycolide) 50:50 polymer with an intrinsic viscosity of 0.41 dl/g (0.1%, chloroform, 25° C.) was dissolved in 7.875 g of methylene chloride at 10% w/w concentration, along with 0.3 g of DOTAP. The clear organic phase was then emulsified into 500 ml of PVA aqueous solution (0.35% w/v) by homogenization at 4000 rpm for 30 minutes at room temperature using a laboratory mixer (Silverson L4R, Silverson Instruments). System temperature was then raised to 40° C. by circulating hot water through the jacket of the mixing vessel. Simultaneously, the stirring rate was reduced to 1500 rpm, and these conditions were maintained for 2 hours to extract and evaporate methylene chloride. The microsphere suspension was allowed to cool down to room temperature with the help of circulating cold water.

Microparticles were separated by centrifugation at 8000 rpm for 10 minutes at room temperature (Beckman Instruments) and resuspended in deionized water by gentle bath sonication. The centrifugal wash was repeated two additional times to remove excess PVA from the particle surface. Final centrifugal pellets of particles were suspended in approximately 10 ml of water, and lyophilized overnight. The dried cationic microsphere powder was characterized for size and surface charge: mean size (number weighted, µ)=1.4; zeta potential (mV)=32.4.

Unmodified poly(lactic acid, glycolic acid) biodegradable microspheres (umPLGA) were synthesized, rinsed and dried as described above, except the 0.3 g of DOTAP was omitted. The dried microsphere powder was characterized for size and surface charge: mean size (number weighted, µ)=1.1; zeta potential (mV)=−18.1.

Example 3

Immunomodulation with Complexes of Hexameric IMO and MC

Hexameric oligonucleotides were tested for immunomodulatory activity alone and complexed with lactic acid/glycolic acid copolymer microcarrier beads using a human peripheral blood mononuclear cells (hPBMC) assay. Peripheral blood was collected from healthy volunteers by venipuncture using heparinized syringes. Blood was layered onto a FICOLL® (Amersham Pharmacia Biotech) cushion and centrifuged. hPBMCs, located at the FICOLL® interface, were collected, then washed twice with cold phosphate buffered saline (PBS). The cells were resuspended and cultured in 48 well plates at 2×10$^6$ cells/mL at 37° C. in RPMI 1640 with 10% heat-inactivated human AB serum plus 50 units/mL penicillin, 50 μg/mL streptomycin, 300 μg/mL glutamine, 1 mM sodium pyruvate, and 1×MEM non-essential amino acids (NEAA).

Oligonucleotides were tested as single agents, or in combination with PLGA microspheres (unmodified or cationic). All oligonucleotides contained 100% phosphorothioate linkages and were tested at 20 μg/ml. The PLGA microcarriers were used at 250 μg/ml. When oligos were tested with PLGA microcarriers, the oligo and the microcarriers were added at the same time to the culture. The cells were cultured in the in the presence of test samples for 24 hours, then cell-free medium was collected from each well and assayed for IFN-γ and IFN-α concentration. Two different oligonucleotides were used as controls: a first oligonucleotide known to have immunostimulatory activity (a 22mer oligonucleotide containing an ISS ("ISS+," 5'-TGACTGTGAACGTTC-GAGATGA-3'(SEQ ID NO:2)) and a second oligonucleotide of similar sequence but lacking immunostimulatory activity ("ISS−," 5'-TGACTGTGAACCTTAGAGATGA-3' (SEQ ID NO:1)). SAC (PANSORBIN® CalBiochem, 1/5000 dilution) and a untreated culture were used as additional positive and negative controls, respectively. SAC contains *Staph. aureus* (Cowan I) cell material. All samples were assayed in duplicate.

IFN-γ and IFN-α were assayed using CYTOSCREEN™ ELISA kits from BioSource International, Inc., according to the manufacturer's instructions.

In the human PBMC assay, background levels of IFN-γ can vary, even significantly, with the donor. Levels of IFN-αc, however, demonstrate a generally stable pattern of activation and routinely exhibit low background levels under unstimulated conditions.

Three hexameric oligonucleotides were tested: 6-1 (5'-TCGTCG-3'), 6-16 (5'-AACGTT-3'), and 6-7 (5'-ATCGAT-3'). Table 3 shows the assay results. Results are shown as picograms per milliliter (pg/mL) of interferon-gamma (IFN-γ) or interferon-alpha (IFN-α). Because of variability between assays using PBMC from different human donors, results are shown for assays using different donor cells (donors 28033 and 28034) and as a mean.

As shown in Table 3, neither PLGA (cationic or unmodified) nor any of hexameric oligonucleotides had significant activity alone. However, hexameric oligonucleotides 6-1 and 6-7 were active when used in combination with cationic PLGA. Cationic PLGA will adsorb oligonucleotides by electrostatic bonding, creating an oligonucleotide/microcarrier complex, while unmodified PGLA will not. 6-1 and 6-7 have a common motif of 5'-X$_1$TCGX$_2$-3', where the oligonucleotide is a hexamer and X$_1$ is 0 or 1 nucleotide and X$_2$ is 2-3 nucleotides. Interestingly, contrary to the teaching of Liang et al. (*J. Clin. Invest.* 98(5):119-29, 1996) that (TCG)$_3$ is a minimal stimulatory element, 6-1, (TCG)$_2$, exhibited significant immunomodulatory activity when administered in the form of a complex with a microcarrier.

6-16, which contains a CG but no TCG, was found to induce IFN-α in one of the two donors in this experiment when used in combination with cationic PLGA. IMOs with less optimal motifs show more variability among donors.

TABLE 3

| | IFN-γ (pg/ml) | | | IFN-α (pg/ml) | | |
|---|---|---|---|---|---|---|
| Sample | 28033 | 28034 | Mean | 28033 | 28034 | Mean |
| SAC | 1179 | 2000 | 1589 | 50 | 969 | 510 |
| untreated | 0 | 3 | 2 | 0 | 18 | 9 |
| ISS+ | 99 | 223 | 161 | 28 | 106 | 67 |
| ISS− | 3 | 8 | 5 | 0 | 31 | 15 |
| 6-1 | 0 | 4 | 2 | 0 | 40 | 20 |
| 6-16 | 0 | 3 | 2 | 3 | 48 | 26 |
| 6-7 | 0 | 3 | 2 | 8 | 22 | 15 |
| cPLGA | 13 | 6 | 10 | 6 | 50 | 28 |
| ISS+/cPLGA | 399 | 387 | 398 | 2000 | 1496 | 1748 |
| ISS−/cPLGA | 9 | 10 | 9 | 0 | 21 | 11 |
| 6-1/cPLGA | 332 | 544 | 438 | 1074 | 2000 | 1537 |
| 6-16/cPLGA | 18 | 30 | 24 | 15 | 1875 | 945 |
| 6-7/cPLGA | 205 | 245 | 225 | 950 | 2000 | 1475 |
| umPLGA | 4 | 10 | 7 | 0 | 308 | 154 |
| ISS+/umPLGA | 38 | 143 | 90 | 31 | 199 | 115 |
| ISS−/umPLGA | 18 | 13 | 15 | 0 | 32 | 16 |
| 6-1/umPLGA | 7 | 17 | 12 | 0 | 39 | 20 |
| 6-16/umPLGA | 5 | 12 | 9 | 0 | 53 | 26 |
| 6-7/umPLGA | 4 | 7 | 6 | 0 | 49 | 24 |

Example 4

Immunomodulation with Complexes of MC and Hexameric or Pentameric IMO

Additional hexameric and pentameric oligonucleotides were tested for immunomodulatory activity in the PBMC assay. Oligonucleotides 6-6 (5'-TCGAGA-3'), 6-8 (5'-GTC-GAC-3'), 6-9 (5'-GTCGTT-3'), 6-2 (5'-TCGTTT-3'), 6-3 (5'-TTCGTT-3'), 6-4 (5'-TTTCGT-3'), 5-1 (5'-TCGTC-3'), and 5-2 (5'-TCGTT-3') were tested alone or in combination with cationic PLGA as described in Example 3 except that the oligos and PLGA were premixed for 15 minutes room temperature before addition to the cultures. The test articles were assayed using PBMC isolated from donors 28044 and 28045.

As shown in Table 4, oligonucleotides shorter than seven nucleotides had no activity when given alone. However, when co-administered with cPLGA to form oligonucleotide/MC complexes, oligonucleotides fitting the consensus sequence 5'-X$_1$TCGX$_2$-3', where X$_1$ is zero or one nucleotides, X$_2$ is zero to three nucleotides, and the oligo is a pentamer or a hexamer, had immunomodulatory activity.

TABLE 4

| | IFN-γ (pg/ml) | | | IFN-α (pg/ml) | | |
|---|---|---|---|---|---|---|
| Sample | 28044 | 28045 | Mean | 28044 | 28045 | Mean |
| untreated | 8 | 0 | 4 | 0 | 0 | 0 |
| ISS+ | 2180 | 669 | 1425 | 401 | 39 | 220 |
| ISS− | 410 | 51 | 231 | 0 | 0 | 0 |
| SAC | 2040 | 1136 | 1588 | 393 | 43 | 218 |
| 6-6 | 0 | 0 | 0 | 0 | 0 | 0 |
| 6-8 | 6 | 0 | 3 | 0 | 0 | 0 |
| 6-9 | 6 | 0 | 3 | 0 | 0 | 0 |
| 6-2 | 30 | 0 | 15 | 0 | 0 | 0 |
| 6-4 | 13 | 0 | 6 | 0 | 0 | 0 |
| 6-3 | 6 | 0 | 3 | 0 | 0 | 0 |
| 5-1 | 6 | 7 | 6 | 0 | 0 | 0 |
| 5-2 | 4 | 0 | 2 | 0 | 0 | 0 |
| cPLGA | 46 | 148 | 97 | 2 | 0 | 1 |
| ISS+/cPLGA | 3382 | 468 | 1925 | 587 | 171 | 379 |
| ISS−/cPLGA | 147 | 115 | 131 | 0 | 0 | 0 |
| 6-6/cPLGA | 606 | 128 | 367 | 2501 | 35 | 1268 |
| 6-8/cPLGA | 679 | 371 | 525 | 2455 | 97 | 1276 |
| 6-9/cPLGA | 2492 | 1669 | 2080 | 3347 | 455 | 1901 |
| 6-2/cPLGA | 3438 | 1848 | 2643 | 4978 | 837 | 2908 |
| 6-4/cPLGA | 136 | 49 | 93 | 48 | 0 | 24 |
| 6-3/cPLGA | 2057 | 1388 | 1722 | 2073 | 276 | 1175 |
| 5-1/cPLGA | 1294 | 864 | 1079 | 3668 | 180 | 1924 |
| 5-2/cPLGA | 2040 | 1136 | 1588 | 393 | 43 | 218 |

Example 5

Immunomodulation with Complexes of MC and Hexameric or Pentameric IMO

The immunomodulatory activity of the oligonucleotides used in Examples 3 and 4 was confirmed with the human PBMC assay using PBMCs from an additional four donors (donors 28051-28054). Oligonucleotides were tested alone or in combination with cationic PLGA as described in Example 3, except that 96 well plates were used instead of 48 well plates and the oligonucleotides were premixed with the cationic microspheres at room temperature for 15 minutes before they were added to the culture, rather than being added simultaneously to the culture. Results are shown in Table 5.

Consistent with the results of Examples 3 and 4, oligonucleotides that contain the consensus sequence, 5'-$X_1$TCG$X_2$-3', where the oligonucleotide is a hexamer or pentamer and $X_1$ is 0-1 nucleotides and $X_2$ is 2-3 nucleotides, were highly active when delivered as IMO/MC complexes, while they were inactive when delivered alone (6-6, 6-1, 6-7, 6-8, 6-9, 6-2, 6-3, 5-1, and 5-2). Oligonucleotides 6-16 and 6-4 do not fit this consensus sequence, and exhibited variable activity in the assay.

Example 6

Immunomodulation with Complexes of MC and Trimeric, Quatrameric, Pentameric and Hexameric Oligonucleotides Additional oligonucleotides were tested for immunomodulatory activity in the human PBMC assay. Oligonucleotides were tested alone or in combination with cPLGA as described in Example 5.

As shown in Table 6, oligonucleotides shorter than seven nucleotides did not have significant activity when given alone. Oligonucleotides conforming to the consensus sequence, 5'-$X_1$TCG$X_2$-3', where the oligonucleotide is a hexamer and $X_1$ is 0 and $X_2$ is 3 nucleotides, were highly active when delivered as IMO/MC complexes (6-2, 6-12). 6-12, a phosphodiester IMO with the sequence 5'-TCGTCG-3', had significant activity when delivered as an IMO/MC complex, demonstrating that the IMO can contain either phosphodiester or phosphorothioate linkages. Oligonucleotides 6-13, 6-14, and 6-15, which contain a CG but not a TCG, were inactive in the PBMC assay when delivered alone or as an oligonucleotide/MC complex. 4-1, a quadramer with the sequence 5'-TCGT-3', and 3-1, a trimer with the sequence 5'-TCG-3', were active in two out of four donors, suggesting that hexamers and pentamers with the consensus sequence are more optimal IMOs.

TABLE 5

| Sample | IFN-γ (pg/ml) | | | | | IFN-α (pg/ml) | | | | |
| --- | --- | --- | --- | --- | --- | --- | --- | --- | --- | --- |
| | 28051 | 28052 | 28053 | 28054 | Mean | 28051 | 28052 | 28053 | 28054 | Mean |
| Untreated | 17 | 1 | 1 | 10 | 7 | 4 | 2 | 2 | 15 | 6 |
| SAC | 380 | 688 | 159 | 73 | 325 | 2246 | 364 | 1129 | 1029 | 1192 |
| ISS+ | 66 | 20 | 72 | 23 | 45 | 12 | 28 | 12 | 12 | 16 |
| ISS− | 5 | 2 | 3 | 2 | 3 | 0 | 3 | 1 | 5 | 2 |
| 6-6 | 2 | 2 | 1 | 2 | 2 | 1 | 4 | 0 | 10 | 4 |
| 6-1 | 2 | 3 | 1 | 2 | 2 | 0 | 2 | 1 | 4 | 2 |
| 6-16 | 1 | 2 | 2 | 8 | 3 | 2 | 1 | 1 | 2 | 2 |
| 6-7 | 1 | 1 | 2 | 2 | 1 | 1 | 0 | 4 | 1 | 2 |
| 6-8 | 0 | 0 | 1 | 2 | 1 | 1 | 0 | 6 | 0 | 2 |
| 6-9 | 1 | 0 | 2 | 1 | 1 | 0 | 0 | 6 | 0 | 2 |
| 6-2 | 1 | 0 | 3 | 1 | 1 | 0 | 2 | 10 | 0 | 3 |
| 6-4 | 3 | 0 | 2 | 0 | 1 | 0 | 2 | 11 | 0 | 3 |
| 6-3 | 1 | 0 | 5 | 0 | 2 | 0 | 5 | 5 | 0 | 3 |
| 5-1 | 1 | 0 | 1 | 0 | 1 | 0 | 3 | 1 | 1 | 1 |
| 5-2 | 1 | 0 | 0 | 1 | 0 | 1 | 5 | 0 | 2 | 2 |
| cPLGA | 59 | 59 | 3 | 211 | 83 | 22 | 5 | 1 | 1111 | 285 |
| ISS+/cPLGA | 2187 | 414 | 181 | 206 | 747 | 1127 | 419 | 305 | 515 | 591 |
| ISS−/cPLGA | 47 | 42 | 30 | 17 | 34 | 1 | 3 | 1 | 2 | 2 |
| 6-6/cPLGA | 182 | 196 | 92 | 908 | 345 | 1480 | 35 | 336 | 1034 | 721 |
| 6-1/cPLGA | 619 | 334 | 274 | 315 | 386 | 2352 | 887 | 991 | 2174 | 1601 |
| 6-16/cPLGA | 284 | 95 | 30 | 135 | 136 | 643 | 7 | 16 | 4 | 168 |
| 6-7/cPLGA | 2000 | 278 | 284 | 600 | 790 | 2711 | 425 | 728 | 1972 | 1459 |
| 6-8/cPLGA | 1168 | 208 | 229 | 308 | 478 | 1936 | 138 | 522 | 966 | 891 |
| 6-9/cPLGA | 2307 | 317 | 212 | 629 | 866 | 1805 | 386 | 844 | 1761 | 1199 |
| 6-2/cPLGA | 984 | 179 | 138 | 327 | 407 | 2255 | 536 | 1186 | 2541 | 1629 |
| 6-4/cPLGA | 318 | 41 | 13 | 72 | 111 | 580 | 6 | 11 | 37 | 158 |
| 6-3/cPLGA | 1448 | 162 | 114 | 655 | 595 | 2066 | 165 | 586 | 1130 | 987 |
| 5-1/cPLGA | 1609 | 146 | 122 | 273 | 538 | 1833 | 121 | 552 | 887 | 848 |
| 5-2/cPLGA | 1500 | 365 | 165 | 2000 | 1008 | 1585 | 174 | 1285 | 1133 | 1044 |

TABLE 6

| Sample | IFN-γ (pg/ml) | | | | | IFN-α (pg/ml) | | | | |
|---|---|---|---|---|---|---|---|---|---|---|
| | 28075 | 28076 | 28077 | 28078 | Mean | 28075 | 28076 | 28077 | 28078 | Mean |
| Untreated | 8 | 14 | 11 | 13 | 12 | 12 | 41 | 256 | 38 | 87 |
| SAC | 1118 | 386 | 71 | 1607 | 796 | 200 | 2017 | 113 | 498 | 707 |
| ISS+ | 48 | 76 | 15 | 72 | 53 | 0 | 73 | 54 | 94 | 55 |
| ISS− | 15 | 15 | 12 | 16 | 15 | 41 | 23 | 54 | 27 | 36 |
| 6-12 | 8 | 13 | 13 | 18 | 13 | 5 | 3 | 187 | 181 | 94 |
| 6-2 | 8 | 18 | 5 | 14 | 11 | 36 | 6 | 66 | 101 | 53 |
| 6-13 | 8 | 225 | 18 | 15 | 67 | 10 | 39 | 28 | 34 | 28 |
| 6-14 | 11 | 12 | 14 | 11 | 12 | 15 | 51 | 9 | 230 | 76 |
| 6-15 | 11 | 12 | 15 | 11 | 13 | 36 | 9 | 35 | 36 | 29 |
| 4-1 | 9 | 12 | 14 | 14 | 12 | 0 | 3 | 0 | 10 | 3 |
| 3-1 | 7 | 11 | 12 | 15 | 11 | 0 | 0 | 4 | 11 | 4 |
| cPLGA | 16 | 22 | 16 | 14 | 17 | 0 | 2 | 2 | 9 | 4 |
| ISS+/cPLGA | 389 | 732 | 80 | 73 | 318 | 30 | 274 | 48 | 66 | 104 |
| ISS−/cPLGA | 18 | 13 | 12 | 18 | 15 | 21 | 6 | 8 | 17 | 13 |
| 6-12/cPLGA | 159 | 1047 | 46 | 40 | 323 | 119 | 1149 | 123 | 555 | 486 |
| 6-2/cPLGA | 731 | 1079 | 484 | 93 | 597 | 525 | 1417 | 687 | 1020 | 912 |
| 6-13/cPLGA | 12 | 15 | 12 | 15 | 14 | 83 | 17 | 16 | 11 | 32 |
| 6-14/cPLGA | 11 | 21 | 23 | 19 | 19 | 42 | 13 | 3 | 36 | 24 |
| 6-15/cPLGA | 11 | 15 | 13 | 17 | 14 | 26 | 7 | 20 | 2 | 14 |
| 4-1/cPLGA | 14 | 159 | 17 | 19 | 52 | 30 | 135 | 15 | 196 | 94 |
| 3-1/cPLGA | 14 | 26 | 14 | 27 | 20 | 21 | 51 | 5 | 193 | 67 |

Additional oligonucleotides were tested using hPBMCs from volunteers 154-157 using the same assay. Results, which are shown in Table 7, confirm the activity of oligonucleotides fitting the formula 5'-$X_1$TCG$X_2$-3', where the oligonucleotide is a 3-6mer, $X_1$ is zero or one nucleotide and $X_2$ is zero to three nucleotides. Interestingly, oligonucleotides 6-17 and 6-18 were largely inactive in this assay, in contrast to the teachings of International Patent Application No. 98/52962.

TABLE 7

| Sample | IFN-γ (pg/ml) | | | | | IFN-α (pg/ml) | | | | |
|---|---|---|---|---|---|---|---|---|---|---|
| | 154 | 155 | 156 | 157 | Mean | 154 | 155 | 156 | 157 | Mean |
| Untreated | 0 | 0 | 14 | 0 | 4 | 0 | 0 | 0 | 0 | 0 |
| SAC | 2689 | 117 | 914 | 4000 | 1930 | 155 | 19 | 261 | 119 | 139 |
| ISS+ | 211 | 131 | 86 | 840 | 317 | 31 | 0 | 15 | 0 | 12 |
| ISS− | 0 | 17 | 58 | 98 | 43 | 0 | 0 | 0 | 0 | 0 |
| 6-1 | 0 | 0 | 11 | 0 | 3 | 0 | 0 | 0 | 0 | 0 |
| 6-5 | 0 | 0 | 11 | 0 | 3 | 0 | 0 | 0 | 0 | 0 |
| 6-17 | 0 | 0 | 16 | 0 | 4 | 0 | 0 | 0 | 0 | 0 |
| 6-18 | 0 | 0 | 15 | 0 | 4 | 0 | 0 | 0 | 0 | 0 |
| 6-20 | 0 | 0 | 13 | 0 | 3 | 0 | 0 | 0 | 0 | 0 |
| 6-10 | 0 | 0 | 15 | 0 | 4 | 0 | 0 | 0 | 0 | 0 |
| 6-11 | 0 | 0 | 10 | 0 | 3 | 0 | 0 | 0 | 0 | 0 |
| cPLGA | 14 | 0 | 18 | 111 | 36 | 0 | 0 | 0 | 0 | 0 |
| ISS+/cPLGA | 662 | 534 | 689 | 4000 | 1471 | 151 | 62 | 240 | 137 | 148 |
| ISS−/cPLGA | 21 | 22 | 36 | 97 | 44 | 0 | 0 | 25 | 0 | 6 |
| 6-1/cPLGA | 1253 | 883 | 487 | 0 | 656 | 513 | 513 | 754 | 467 | 562 |
| 6-5/cPLGA | 28 | 25 | 38 | 31 | 31 | 0 | 0 | 0 | 0 | 0 |
| 6-17/cPLGA | 86 | 42 | 34 | 175 | 84 | 58 | 21 | 0 | 0 | 20 |
| 6-18/cPLGA | 43 | 32 | 24 | 182 | 70 | 0 | 0 | 0 | 0 | 0 |
| 6-20/cPLGA | 0 | 0 | 19 | 46 | 16 | 0 | 0 | 0 | 0 | 0 |
| 6-10/cPLGA | 824 | 400 | 199 | 4000 | 1356 | 340 | 638 | 1099 | 450 | 632 |
| 6-11/cPLGA | 94 | 14 | 0 | 382 | 123 | 23 | 0 | 0 | 22 | 11 |

Example 7

Immunomodulation with Complexes of MC and Pentameric and Hexameric Oligonucleotides Additional oligonucleotides, some incorporating modified bases, were tested for immunomodulatory activity in the human PBMC assay. Oligonucleotides were tested alone or in combination with cPLGA as described in Example 5. The oligonucleotides were premixed with the cationic PLGA microspheres for 15 minutes at room temperature at concentrations of 20 μg/ml and 100 μg/ml, respectively.

As shown in Table 8, hexameric phosphorothioate oligonucleotides containing modified bases were tested, along with 6-2 (5'-TCGTTT-3', positive hexamer) and 6-20 (5'-TCCTTT-3', negative hexamer control). When combined with cPLGA, 6-21 and 6-24 were active. In addition, 6-25, a hexamer fitting the consensus motife $X_1$TCG$X_2$, where $X_1$ is two nucleotides and $X_2$ is one nucleotide, was also active in combination with cPLGA.

Table 8 also shows that pentameric oligonucleotides fitting the consensus sequence $X_1$TCG$X_2$, where $X_1$ is zero or one nucleotide and $X_2$ is one to two nucleotides, are active in combination with cPLGA. Oligonucleotides 5-2 and 5-3 were each active in two of four donors when combined with cPLGA.

TABLE 8

| Sample | IFN-γ (pg/ml) | | | | | IFN-α (pg/ml) | | | | |
|---|---|---|---|---|---|---|---|---|---|---|
| | 28115 | 28116 | 28117 | 28118 | Mean | 28115 | 28116 | 28117 | 28118 | Mean |
| Untreated | 3 | 8 | 43 | 2 | 14 | 4 | 0 | 0 | 0 | 1 |
| SAC | 440 | 827 | 3494 | 2912 | 1918 | 0 | 11 | 353 | 78 | 111 |
| ISS+ | 156 | 125 | 497 | 46 | 206 | 54 | 29 | 17 | 0 | 25 |
| ISS− | 20 | 22 | 334 | 14 | 98 | 0 | 0 | 0 | 0 | 0 |
| 6-2 | 3 | 0 | 5 | 0 | 2 | 0 | 0 | 0 | 0 | 0 |
| 6-20 | 6 | 3 | 9 | 0 | 5 | 0 | 0 | 0 | 0 | 0 |
| 6-21 | 27 | 0 | 7 | 0 | 8 | 0 | 0 | 0 | 0 | 0 |
| 6-22 | 7 | 0 | 17 | 0 | 6 | 0 | 0 | 0 | 0 | 0 |
| 6-24 | 3 | 0 | 16 | 0 | 5 | 0 | 0 | 0 | 0 | 0 |
| 6-25 | 2 | 15 | 11 | 0 | 7 | 7 | 0 | 0 | 0 | 2 |
| 5-2 | 8 | 4 | 8 | 0 | 5 | 0 | 0 | 0 | 0 | 0 |
| 5-3 | 26 | 4 | 17 | 0 | 12 | 10 | 0 | 0 | 0 | 3 |
| cPLGA | 66 | 14 | 99 | 12 | 48 | 85 | 11 | 158 | 75 | 82 |
| ISS+/cPLGA | 2191 | 351 | 692 | 40 | 819 | 404 | 89 | 170 | 64 | 182 |
| ISS−/cPLGA | 62 | 90 | 698 | 25 | 219 | 0 | 0 | 0 | 0 | 0 |
| 6-2/cPLGA | 2538 | 153 | 924 | 75 | 923 | 2153 | 243 | 4000 | 593 | 1747 |
| 6-20/cPLGA | 64 | 23 | 32 | 19 | 35 | 272 | 25 | 39 | 76 | 103 |
| 6-21/cPLGA | 1488 | 25 | 711 | 60 | 571 | 1554 | 56 | 650 | 303 | 641 |
| 6-22/cPLGA | 162 | 14 | 187 | 38 | 100 | 199 | 41 | 79 | 93 | 103 |
| 6-24/cPLGA | 2503 | 153 | 664 | 85 | 851 | 4000 | 453 | 4000 | 896 | 2337 |
| 6-25/cPLGA | 2357 | 143 | 1013 | 55 | 892 | 2160 | 132 | 516 | 190 | 750 |
| 5-2/cPLGA | 1376 | 40 | 320 | 25 | 440 | 892 | 64 | 296 | 429 | 420 |
| 5-3/cPLGA | 687 | 6 | 139 | 20 | 213 | 274 | 0 | 86 | 97 | 114 |

Although the foregoing invention has been described in some detail by way of illustration and example for purposes of clarity and understanding, it will be apparent to those skilled in the art that certain changes and modifications may be practiced. Therefore, descriptions and examples should not be construed as limiting the scope of the invention, which is delineated by the appended claims.

We claim:

1. A composition comprising a complex of an oligonucleotide three to six nucleotides in length bound to the surface of a solid phase microcarrier (MC), wherein said oligonucleotide consists of a sequence according to the formula 5'-$X_1$TCG$X_2$-3' or 5'-$X_1$UCG$X_2$-3', where $X_1$ is zero or one nucleotide and $X_2$ is zero to three nucleotides, and wherein the oligonucleotide alone induces interferon-α secretion at a level of no more than 20% of the complex.

2. The composition of claim 1, wherein said oligonucleotide consists of a sequence according to the formula 5'-$X_1$TCG$X_2$-3'.

3. The composition according to claim 1, wherein said oligonucleotide consists of a sequence according to the formula 5'-$X_1$UCG$X_2$-3'.

4. The composition of claim 1, wherein said oligonucleotide is six nucleotides in length.

5. The composition of claim 1, wherein said oligonucleotide is five nucleotides in length.

6. The composition of claim 1, wherein said oligonucleotide is four nucleotides in length.

7. The composition of claim 1, wherein said oligonucleotide is three nucleotides in length.

8. The composition of claim 1, wherein said oligonucleotide comprises at least one phosphorothioate linkage.

9. The composition of claim 1, wherein said oligonucleotide comprises at least one modified cytosine.

10. The composition of claim 1, wherein the microcarrier is a biodegradable polymeric particle.

11. The composition of claim 10, wherein the biodegradable polymeric particle is a biodegradable polyester particle.

12. The composition of claim 11, wherein the biodegradable polyester particle comprises a polymer selected from the group consisting of poly(lactic acid), poly(glycolic acid), poly(lactic-co-glycolic acid), poly(caprolactone), and polymethylidene malonate.

13. The composition of claim 1, wherein said microcarrier comprises a cationic moiety.

14. The composition of claim 1, wherein said microcarrier comprises an inorganic particle.

15. The composition of claim 14, wherein said inorganic particle comprises an inorganic crystalline material.

16. The composition of claim 15, wherein said inorganic crystalline material is selected from the group consisting of hydroxyapatite and calcium phosphate.

17. The composition of claim 1, wherein said microcarrier is 10 nm to 10 μm in size.

18. The composition of claim 1, wherein said microcarrier is 25 nm to 5 μm in size.

19. The composition of claim 1, further comprising an antigen.

20. The composition of claim 19, wherein said antigen is linked to said complex.

21. The composition of claim 20, wherein said antigen is non-covalently linked to said complex.

22. The composition of claim 20, wherein said antigen is covalently linked to said complex.

23. The composition of claim 22, wherein said antigen is covalently linked to the MC of the complex.

24. The composition of claim 22, wherein said antigen is covalently linked to the oligonucleotide of the complex.

25. The composition of claim 19, wherein said antigen is not linked to said complex.

26. The composition of claim 1, wherein said composition does not comprise an antigen.

27. The composition of claim 1, wherein said complex does not comprise a further oligonucleotide greater than 6 nucleotides in length.

28. A pharmaceutical composition, comprising:
a complex of an oligonucleotide three to six nucleotides in length bound to the surface of a solid phase microcarrier (MC), wherein said has oligonucleotide consists of a sequence according to the formula 5'-$X_1$TCG$X_2$-3' or 5'-$X_1$UCG$X_2$-3', where $X_1$ is zero or one nucleotide and $X_2$ is zero to three nucleotides, and wherein the oligonucleotide alone induces interferon-α secretion at a level of no more than 20% of the complex; and a pharmaceutically acceptable excipient.

29. A method of modulating an immune response in an individual, comprising administering to said individual an amount of a complex of effective to modulate an immune response in said individual, wherein the complex comprises an oligonucleotide three to six nucleotides in length bound to the surface of a solid phase microcarrier (MC), wherein said oligonucleotide consists of a sequence according to the formula 5'-$X_1$TCG$X_2$-3' or 5'-$X_1$UCG$X_2$-3', where $X_1$ is zero or one nucleotide and $X_2$ is zero to three nucleotides, and wherein the oligonucleotide alone induces interferon-α secretion at a level of no more than 20% of the complex.

30. The composition of claim 1, wherein the oligonucleotide is covalently bound to the surface of the MC.

31. The composition of claim 1, wherein the oligonucleotide is non-covalently bound to the surface of the MC.

32. The composition of claim 1, wherein said oligonucleotide does not comprise a palindromic sequence.

33. The method of claim 29, wherein said oligonucleotide consists of a sequence according to the formula 5'-X TCG$X_2$-3'.

34. The method of claim 29, wherein said oligonucleotide consists of a sequence according to the formula 5'-$X_1$UCG$X_2$-3'.

35. The method of claim 29, wherein said oligonucleotide comprises at least one phosphorothioate linkage.

36. The method of claim 29, wherein said oligonucleotide does not comprise a palindromic sequence.

37. A method of increasing interferon-alpha (IFN-α) in an individual, comprising administering to said individual an amount of a complex effective to increase IFN-α in said individual, wherein the complex comprises an oligonucleotide three to six nucleotides in length bound to the surface of a solid phase microcarrier (MC), wherein said oligonucleotide consists of a sequence according to the formula 5'-$X_1$TCG$X_2$-3' or 5'-$X_1$UCG$X_2$-3', where $X_1$ is zero or one nucleotide and $X_2$ is zero to three nucleotides, and wherein the oligonucleotide alone induces interferon-α secretion at a level of no more than 20% of the complex.

* * * * *

UNITED STATES PATENT AND TRADEMARK OFFICE
CERTIFICATE OF CORRECTION

PATENT NO. : 8,586,555 B2
APPLICATION NO. : 12/396348
DATED : November 19, 2013
INVENTOR(S) : Karen L. Fearon et al.

It is certified that error appears in the above-identified patent and that said Letters Patent is hereby corrected as shown below:

On Title page 2, under "Other Publications", in column 1, line 2, Delete "oligodeoxynulcleotides" and insert -- oligodeoxynucleotides --, therefor.

On Title page 2, under "Other Publications", in column 2, line 43, Delete "Requiements" and insert -- Requirements --, therefor.

On Title page 2, under "Other Publications", in column 2, line 63, Delete "Vacine" and insert -- Vaccine --, therefor.

On Title page 3, under "Other Publications", in column 1, line 31, Delete "Calll" and insert -- Cell --, therefor.

On Title page 3, under "Other Publications", in column 1, line 34, Delete "Coversion" and insert -- Conversion --, therefor.

On Title page 3, under "Other Publications", in column 2, line 30, Delete "(2001)." and insert -- (2000). --, therefor.

On Title page 4, under "Other Publications", in column 2, line 24, Delete "N-Hydroxysulfosucciniminde" and insert -- N-Hydroxysulfosuccinimide --, therefor.

On Title page 4, under "Other Publications", in column 2, line 55, Delete "Oligodeoxymucleotides,"" and insert -- Oligodeoxynucleotides," --, therefor.

In the Specification

In column 2, line 67, Delete "5'-GACGTT-3',5'-GAGCTT-3'," and insert -- 5'-GACGTT-3', 5'-GAGCTT-3', --, therefor.

Signed and Sealed this
Eighteenth Day of February, 2014

Michelle K. Lee
*Deputy Director of the United States Patent and Trademark Office*

CERTIFICATE OF CORRECTION (continued)
U.S. Pat. No. 8,586,555 B2

In column 6, line 4, Delete "immomodulatory" and insert -- immunomodulatory --, therefor.

In column 6, line 11, Delete "5'-GACGTT-3',5'-TCCGGA-3'," and
insert -- 5'-GACGTT-3', 5'- TCCGGA-3', --, therefor.

In column 10, lines 34-35, Delete "*Hemophilus*" and insert -- *Haemophilus* --, therefor.

In column 13, line 49, Delete "5'-GACGTT-3',5'-TCCGGA-3'," and
insert -- 5'-GACGTT-3', 5'- TCCGGA-3', --, therefor.

In column 14, lines 2-3, Delete "5'-$X_1$TCG-3',5'-TCG$X_2$-3',5'-$X_1$UCG-3'" and
insert -- 5'-$X_1$TCG-3', 5'-TCG$X_2$-3', 5'-$X_1$UCG-3' --, therefor.

In column 15, line 50, Delete "know" and insert -- known --, therefor.

In columns 21-22, "TABLE 1", line 55, Delete "topomyosin" and insert -- tropomyosin --, therefor.

In column 23-24, "TABLE 1", line 40, Delete "*Penicillinium*" and insert -- *Penicillium* --, therefor.

In column 23, line 44, Delete "*Hemophilus*" and insert -- *Haemophilus* --, therefor.

In column 26, line 40, Delete "(dichlormethane)." and insert -- (dichloromethane). --, therefor.

In column 30, line 53, Delete "5'-TTCGAA-3',5'-GACGTT-3'," and
insert -- 5'-TTCGAA-3', 5'-GACGTT-3', --, therefor.

In column 32, line 14, Delete "*M. Bovis*" and insert -- *M. bovis* --, therefor.

In column 33, line 15, Delete "*M. Bovis*" and insert -- *M. bovis* --, therefor.

In column 36, line 62, Delete "Noxema" and insert -- Noxzema --, therefor.

In column 40, line 41, Delete "phosphorothiate" and insert -- phosphorothioate --, therefor.

In column 40, line 61, Delete "umol" and insert -- μmol --, therefor.

In column 43, line 56, Delete "PGLA" and insert -- PLGA --, therefor.

In column 48, line 59, Delete "motife" and insert -- motif --, therefor.

In the Claims

In column 52, line 4, In Claim 28, Delete "said has" and insert -- said --, therefor.

In column 52, lines 29-30, In Claim 33, Delete "5'X TCG$X_2$-3'." and
insert -- 5'$X_1$TCG$X_2$-3'. --, therefor.